United States Patent
Punnonen et al.

(10) Patent No.: US 10,501,542 B2
(45) Date of Patent: Dec. 10, 2019

(54) CTLA4 BINDERS

(71) Applicant: Merck Sharp & Dohme Corp., Rahway, NJ (US)

(72) Inventors: Juha Punnonen, Belmont, CA (US); Maribel Beaumont, San Mateo, CA (US); Marie-Ange Buyse, Merelbeke (BE); Carlo Boutton, Wielsbeke (BE); Bruno Dombrecht, Heusden (BE); Bjorn Victor, Zwijndrecht (BE); Robert A. Kastelein, Portola Valley, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 270 days.

(21) Appl. No.: 15/353,886

(22) Filed: Nov. 17, 2016

(65) Prior Publication Data

US 2017/0137521 A1    May 18, 2017

Related U.S. Application Data

(60) Provisional application No. 62/257,001, filed on Nov. 18, 2015.

(51) Int. Cl.
    *C07K 16/28*      (2006.01)
    *A61K 39/395*      (2006.01)
    *C07K 14/765*      (2006.01)
    *C07K 16/18*      (2006.01)
    *A61K 39/00*      (2006.01)

(52) U.S. Cl.
CPC ...... *C07K 16/2818* (2013.01); *A61K 39/3955* (2013.01); *A61K 39/39558* (2013.01); *C07K 14/765* (2013.01); *C07K 16/18* (2013.01); *A61K 2039/505* (2013.01); *A61K 2039/54* (2013.01); *A61K 2039/545* (2013.01); *C07K 2317/22* (2013.01); *C07K 2317/24* (2013.01); *C07K 2317/31* (2013.01); *C07K 2317/32* (2013.01); *C07K 2317/33* (2013.01); *C07K 2317/34* (2013.01); *C07K 2317/35* (2013.01); *C07K 2317/565* (2013.01); *C07K 2317/569* (2013.01); *C07K 2317/62* (2013.01); *C07K 2317/76* (2013.01); *C07K 2317/92* (2013.01); *C07K 2319/31* (2013.01)

(58) Field of Classification Search
None
See application file for complete search history.

(56) References Cited

U.S. PATENT DOCUMENTS

| | | | |
|---|---|---|---|
| 5,665,862 A | 9/1997 | Fischbach et al. | |
| 5,869,050 A | 2/1999 | de Boer et al. | |
| 6,632,927 B2 | 10/2003 | Adair et al. | |
| 6,824,779 B1 | 11/2004 | Freeman et al. | |
| 7,807,162 B2 * | 10/2010 | Silence | A61K 38/36 424/133.1 |
| 8,907,065 B2 * | 12/2014 | Hermans | C07K 16/2818 530/387.1 |
| 2002/0006403 A1 | 1/2002 | Yu et al. | |
| 2015/0266958 A1 | 9/2015 | Hermans et al. | |
| 2017/0121399 A1 | 5/2017 | Buyse et al. | |
| 2017/0137517 A1 | 5/2017 | Bowman et al. | |
| 2017/0137520 A1 | 5/2017 | Punnonen et al. | |

FOREIGN PATENT DOCUMENTS

| | | |
|---|---|---|
| WO | 199404678 | 3/1994 |
| WO | WO2002051871 | 7/2002 |
| WO | WO2003042402 | 5/2003 |
| WO | 200441865 | 5/2004 |
| WO | WO2006040153 A2 | 4/2006 |
| WO | 2006122787 | 11/2006 |
| WO | 2008071447 | 6/2008 |
| WO | 2008096158 | 8/2008 |
| WO | 2010007376 | 1/2010 |
| WO | 201106915 | 1/2011 |
| WO | 2012175400 | 12/2012 |
| WO | 2013024059 | 2/2013 |
| WO | 2014043509 | 3/2014 |
| WO | 2014111550 | 7/2014 |
| WO | 2015044386 | 2/2015 |
| WO | 2015173325 | 11/2015 |

OTHER PUBLICATIONS

Vincke et al. (Journal of Biological Chemistry, vol. 284, p. 3273-3284).*
Cordy et al., Specificity of human anti variable heavy VH chain autoantibodies and impact on a VH domain antibody antagonist of tumour necrosis factor-alpha receptor 1, Clinical and Experimental Immunology, 2015, No. 2, pp. 139-148, 182.
Vincke et al., General Strategy to Humanize a Camelid Single-domain antibody and Identification of a universal humanized nanobody scaffold, Journal of Biological Chemistry, 2008, vol. 284, No. 5, pp. 3273-3284.
Adorini et al., Therapeutic Aspects of Apoptosis, Idrugs, 2000, pp. 496-498, vol. 3.
Alegre et al., T-Cell Regulation by CD28 and CTLA-4, Nat. Rev. Immunol., 2001, pp. 220-228, vol. 1.
Butte et al., Programmed Death-1 Ligand 1 Interacts Specifically with the B7-1 Costimulatory Molecule to Inhibit T Cell Responses, Immunity, 2007, pp. 111-122, vol. 27.
Chambers et al., CTLA-4-Mediated Inhibition in Regulation of T Cell Responses: Mechanisms and Manipulation in Tumor Immunotherapy, Annu. Rev. Immunol., 2001, pp. 565-594, vol. 19.

(Continued)

*Primary Examiner* — Agnieszka Boesen
(74) *Attorney, Agent, or Firm* — Nichole M. Valeyko; Laura M. Ginkel

(57) ABSTRACT

The present invention provides molecules, such as ISVDs and Nanobodies, that bind to CTLA4 or human serum albumin. These molecules have been engineered so as to reduce the incidence of binding by pre-existing antibodies in the bodies of a subject administered such a molecule. Methods for increasing immune response, treating cancer and/or treating an infectious disease with such molecules are provided.

15 Claims, 32 Drawing Sheets

Specification includes a Sequence Listing.

(56) References Cited

OTHER PUBLICATIONS

Choi et al., Activation of Naive CD4T Cells In Vivo by a Self-Peptide Mimic: Mechanism of Tolerance Maintenance and Preservation of Immunity, J. Immunol., 2004, pp. 7399-7407, vol. 172.
Collins et al., The Interaction Properties of Costimulatory Molecules Revisited, Immunity, 2002, pp. 201-210, vol. 17.
Conrath et al., Camel Single-domain Antibodies as Modular Building Units in Bispecific and Bivalent Antibody Constructs, The Journal of Biological Chemistry, 2001, pp. 7346-7350, vol. 276(10).
Coyle et al., The expanding B7 superfamily: Increasing complexity in costimulatory signals regulating T cell function, Nature Immunology, 2001, pp. 203-209, vol. 2/3.
Coyle et al., The role of ICOS and other costimulatory molecules in allergy and asthma, Immune, 2004, pp. 349-359, vol. 25.
Curran et al., PD1 and CTLA4 combination blockade expands infiltrating T cells and reduces regulatory T and myeloid cells within B16 melanoma tumors, PNAS, 2010, pp. 4275-4280, vol. 107.
Database WPI, Thomson XP002766907, Oct. 21, 2015—Abstract.
Dincq et al., Expression and Purification of Monospecific and Bispecific Recombinant Antibody Fragments Derived from Antibodies That Block the CD80,CD86-CD28 Costimulatory Pathway, Protein Expression and Purification, 2001, pp. 11-24, vol. 22.
Duraiswamy et al., Dual Blockade of PD-1 and CTLA-4 Combined with Tumor Vaccine Effective Restores T-Cell Rejection Function in Tumors, Cancer Research, 2013, pp. 3591-3603, vol. 73.
Friedberg et al., Updated Results from a Phase II Study of Galiximab (anti-CD80) in Combination with Rituximab for Relapsed or Refractory, Follicular NHL, Blood, 2005, p. 2435, vol. 106.
Furukawa et al., Association of B7-1 Co-Stimulation with the Development of Graft Arterial Disease Studies Using Mice Lacking B7-1, B7-2, or B7-1,B7-2, Am. J. of Pathology, 2000, pp. 473-484, vol. 157.
Gottlieb et al., Abstracts for the 61st Annual Meeting of the Society for Investigative Dermatology, J. Invest. Dermatol., 2001, p. 840, vol. 114.
Howard et al., Therapeutic Blockade of TCR Signal Transduction and Co-Stimulation in Autoimmune Disease, Current Drug Targets, 2005, pp. 85-94, vol. 4.
Hufton et al., Development and application of cytotoxic T lymphocyte-associated antigen 4 as a protein scaiold for the generation of novel binding ligands, FEBS Lett., 2000, pp. 225-231, vol. 475.
Kang et al., The Synthetic Peptide Trp-Lys-Tyr-Met-Val-D-Met Inhibits Human Monocyte-Derived Dendritic Cell Maturation via Formyl Peptide Receptor and Formyl Peptide Receptor-Like, J. Immunol., 2005, pp. 685-692, vol. 175.
Karandikar et al., Targeting the B7,CD28:CTLA-4 costimulatory system in CNS autoimmune disease, J. of Neuroimmunology, 1998, pp. 10-18, vol. 89.
Keler et al., Activity and Safety of CTLA-4 Blockade Combined with Vaccines in Cynomolgus Macaques, J. Immunol., 2003, pp. 6251-6259, vol. 171.
Kopf et al., Inducible Costimulator Protein (ICOS) Controls T Helper Cell Subset Polarization after Virus and Parasite Infection, J. Exp. Med., 2000, pp. 53-61, vol. 192.
Larkin et al., Combined Nivolumab and Ipilmumab or Monotherapy in Untreated Melanoma, The New England Journal of Medicine, Jul. 2, 2015, pp. 23-34, vol. 373.
Larsen et al., Rational Development of LEA29Y (belatacept), a High-Affinity Variant of CTLA4-Ig with Potent Immunosuppressive Properties, Am. J. Transplant, 2005, pp. 443-453, vol. 5.
Oosterwegel et al., CTLA-4 and T cell activation, Current Opinion in Immunology, 1999, pp. 294-300, vol. 11.
Ozkaynak et al., Importance of ICOS-B7RP-1 costimulation in acute and chronic allograft rejection, Nature Immunology, 2001, pp. 591-596, vol. 2.
Panka et al., Variable region framework differences result in decreased or increased affinity of variant anti-digoxin antibodies, Proc. Natl. Acad. Sci., USA, 1988, pp. 3080-3084, vol. 85.
Park et al., Targeting and Blocking B7 Costimulatory Molecules on Antigen-Presenting Cells Using CTLA4Ig-Conjugated Liposomes: In Vitro Characterization and in Vivo Factors Affecting Biodistribution, Pharmaceutical Research, 2003, pp. 1239-1248, vol. 20.
Polojil et al., CD4 T Cell Expressed CD80 Regulates Central Nervous System Effector Function and Survival during Experimental Autoimmune Encephalomyelitis, J. of Immunology, 2006, pp. 2948-2958, vol. 177.
Polojil et al., CD86 and beta 2-adrenergic receptor stimulation regulate B-cell activity cooperatively, Trends in Immunology, 2005, pp. 180-185, vol. 26.
Rao et al., Novel cyclic and linear oligopeptides that bind to integrin beta 1 chain and either inhibit or costimulate T lymphocytes, Int. Immunopharmacol., 2003, pp. 435-443, vol. 3.
Rottman et al., The costimulatory molecule ICOS plays an important role in the immunopathogenesis of EAE, Nature Immunology, 2001, pp. 605-611, vol. 2.
Rudikoff, Single amino acid substitution altering antigen-binding specificity, PNAS, 1982, pp. 1979-1983, vol. 79.
S. Muyldermans, Single domain camel antibodies: current status, Molecular Biology, 2001, pp. 277-302, vol. 74.
Salama et al., Challenges to achieving clinical transplantation tolerance, J. of Clinical Investigation, 2001, pp. 943-948, vol. 108.
Shin et al., The evolution of checkpoint blockade as a cancer therapy: what's here, what is next, Current Opinion in Immunology, 2015, pp. 23-35, vol. 33.
Stuart et al., Targeting T Cell Costimulation in Autoimmune Disease, Anti-inflammatory, 2002, Issue No. 3, pp. 275-289, vol. 6.
Van Den Beucken et al., Building Novel Binding Ligands to B7.1 and B7.2 Based on Human Antibody Single Variable Light Chain Domains, J. Mol. Biology, 2001, pp. 591-601, vol. 310.
Waldmann et al., Effective Cancer Therapy Through Immunomodulation, Annu. Rev. Med., 2006, pp. 65-81, vol. 57(1).
Webb et al., Prevention and amelioration of collagen-inducedarthritis by blockade of the CD28 co-stimulatory pathway: requirement for both B7-1 and B7-2, Eur. J. Immunol., 1996, pp. 2320-2328, vol. 26.
Wolchok et al., Nivolumab plus Ipilimumab in Advanced Melanoma, The New England Journal of Medicine, 2013, pp. 122-133, vol. 369(2).
Yamada et al., The Role of Novel T Cell Costimulatory Pathways in Autoimmunity and Transplantation, J. Am. Soc. Nephrol., 2002, pp. 559-575, vol. 13.
Zhang et al., Crystal structure of the receptor-binding domain of human B7-2: Insights into organization and signaling, PNAS, 2003, pp. 2586-2591, vol. 100.
Abrams et al., Blockade of T Lymphocyte Costimulation with Cytotoxic T Lymphocyte—associated Antigen 4-Immunoglobulin (CTLA4Ig) Reverses the Cellular Pathology of Psoriatic Plaques, Including the Activation of Keratinocytes, Dendritic Cells, and Endothelial Cells, J. Exp. Med., 2000, pp. 681-693, vol. 192.
International Search Report, dated Feb. 24, 2017, pp. 1-7.

\* cited by examiner

| Numbering according to Kabat (VH) | Numbering according to Chotia (VH) | Aho numbering | IMGT |
|---|---|---|---|
| 11 | 11 | 12 | 12 |
| 14 | 14 | 15 | 15 |
| 41 | 41 | 48 | 46 |
| 42 | 42 | 49 | 47 |
| 87 | 87 | 101 | 99 |
| 89 | 89 | 103 | 101 |
| 108 | 108 | 144 | --- |
| 110 | 110 | 146 | --- |
| 112 | 112 | 148 | --- |

Source: http://www.bioc.uzh.ch/plueckthun/antibody/Numbering/NumFrame.html

FIG.1

| SEQ ID NO | Description | Sequence |
|---|---|---|
| 1 | Reference A WO 2008/071447, SEQ ID NO:1306 (11F01) | EVQLVESGGGLVQAGGSLRLSCAASGGTFSFYGMGWFRQAPGKEQEFVADIRTSAGRTYYADSVKGRFTISRDNAKNTVYLQMNSLKPEDTAVYYCAAEMSGISGWDYWGQGTQVTVSS |
| 2 | CDR1 (Kabat) | FYGMG |
| 3 | CDR2 (Kabat) | DIRTSAGRTYYADSVKG |
| 4 | CDR3 (Kabat/Abm) | EMSGISGWDY |
| 5 | CDR1 (Abm) | GGTFSFYGMG |
| 6 | CDR2 (Abm) | DIRTSAGRTY |
| 7 | CDR3 (Kabat/Abm) | EMSGISGWDY |
| 8 | Reference A (89T) | EVQLVESGGGLVQAGGSLRLSCAASGGTFSFYGMGWFRQAPGKEQEFVADIRTSAGRTYYADSVKGRFTISRDNAKNTVYLQMNSLKPEDTATYYCAAEMSGISGWDYWGQGTQVTVSS |
| 9 | Reference A (11V + 110K) | EVQLVESGGGVVQAGGSLRLSCAASGGTFSFYGMGWFRQAPGKEQEFVADIRTSAGRTYYADSVKGRFTISRDNAKNTVYLQMNSLKPEDTAVYYCAAEMSGISGWDYWGQGTQVKVSS |
| 10 | Reference A (11V + 110Q) | EVQLVESGGGVVQAGGSLRLSCAASGGTFSFYGMGWFRQAPGKEQEFVADIRTSAGRTYYADSVKGRFTISRDNAKNTVYLQMNSLKPEDTAVYYCAAEMSGISGWDYWGQGTQVQVSS |
| 11 | Reference A (11V + 112K) | EVQLVESGGGVVQAGGSLRLSCAASGGTFSFYGMGWFRQAPGKEQEFVADIRTSAGRTYYADSVKGRFTISRDNAKNTVYLQMNSLKPEDTAVYYCAAEMSGISGWDYWGQGTQVTVKS |
| 12 | Reference A (11V + 112Q) | EVQLVESGGGVVQAGGSLRLSCAASGGTFSFYGMGWFRQAPGKEQEFVADIRTSAGRTYYADSVKGRFTISRDNAKNTVYLQMNSLKPEDTAVYYCAAEMSGISGWDYWGQGTQVTVQS |
| 13 | Reference A (89L + 110K) | EVQLVESGGGLVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTQVKVSS |

FIG.2-1

| SEQ ID NO | Description | Sequence |
|---|---|---|
| 14 | Reference A (89L + 110Q) | EVQLVESGGGLVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTQVQVSS |
| 15 | Reference A (89L + 112K) | EVQLVESGGGLVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTQVTVKS |
| 16 | Reference A (89L + 112Q) | EVQLVESGGGLVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTQVTVQS |
| 17 | Reference A (11V + 89L) | EVQLVESGGGVVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTQVTVSS |
| 18 | Reference A (11V + 89L + 110K) | EVQLVESGGGVVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTQVKVSS |
| 19 | Reference A (11V + 89L + 110Q) | EVQLVESGGGVVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTQVQVSS |
| 20 | Reference A (11V + 89L + 112K) | EVQLVESGGGVVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTQVTVKS |
| 21 | Reference A (11V + 89L + 112Q) | EVQLVESGGGVVQAGGSLRLSCAASGGTFSFYGMGWFRQAPGKEQEFVADIRTSAGRTYYADSVKGRFTISRDNAKNTVYLQMNSLKPEDTALYYCAAEMSGISGWDYWGQGTQVTVQS |
| 22 | CTLA4 binding moiety/binder | EVQLVESGGGVVQPGGSLRLSCAASGGTFSFYGMGWFRQAPGKEQEFVADIRTSAGRTYYADSVKGRFTISRDNSKNTVYLQMNSLRPEDTALYYCAAEMSGISGWDYWGQGTLVTVSS |
| 23 | CTLA4 binding moiety/binder | EVQLVESGGGVVQPGGSLRLSCAASGGTFSFYGMGWFRQAPGKEREFVADIRTSAGRTYYADSVKGRFTISRDNSKNTVYLQMNSLRPEDTALYYCAAEMSGISGWDYWGQGTLVTVSS |

FIG.2-2

| SEQ ID NO | Description | Sequence |
|---|---|---|
| 24 | CTLA4 binding moiety/binder | DVQLVESGGGVVQPGGSLRLSCAASGGTFSFYGMGWFRQAP GKEQEFVADIRTSAGRTYYADSVKGRFTISRDNSKNTVYLQM NSLRPEDTALYYCAAEMSGISGWDYWGQGTLVTVSS |
| 25 | CTLA4 binding moiety/binder | DVQLVESGGGVVQPGGSLRLSCAASGGTFSFYGMGWFRQAP GKEREFVADIRTSAGRTYYADSVKGRFTISRDNSKNTVYLQM NSLRPEDTALYYCAAEMSGISGWDYWGQGTLVTVSS |
| 26 | Reference A (89T)+ A | EVQLVESGGGLVQAGGSLRLSCAASGGTFSFYGMGWFRQAP GKEQEFVADIRTSAGRTYYADSVKGRFTISRDNAKNTVYLQ MNSLKPEDTATYYCAAEMSGISGWDYWGQGTQVTVSSA |
| 27 | Reference A (11V + 110K)+ A | EVQLVESGGGVVQAGGSLRLSCAASGGTFSFYGMGWFRQAP GKEQEFVADIRTSAGRTYYADSVKGRFTISRDNAKNTVYLQ MNSLKPEDTAVYYCAAEMSGISGWDYWGQGTQVKVSSA |
| 28 | Reference A (11V + 110Q)+ A | EVQLVESGGGVVQAGGSLRLSCAASGGTFSFYGMGWFRQAP GKEQEFVADIRTSAGRTYYADSVKGRFTISRDNAKNTVYLQ MNSLKPEDTAVYYCAAEMSGISGWDYWGQGTQVQVSSA |
| 29 | Reference A (11V + 112K)+ A | EVQLVESGGGVVQAGGSLRLSCAASGGTFSFYGMGWFRQAP GKEQEFVADIRTSAGRTYYADSVKGRFTISRDNAKNTVYLQ MNSLKPEDTAVYYCAAEMSGISGWDYWGQGTQVTVKSA |
| 30 | Reference A (11V + 112Q)+ A | EVQLVESGGGVVQAGGSLRLSCAASGGTFSFYGMGWFRQAP GKEQEFVADIRTSAGRTYYADSVKGRFTISRDNAKNTVYLQ MNSLKPEDTAVYYCAAEMSGISGWDYWGQGTQVTVQSA |
| 31 | Reference A (89L + 110K)+ A | EVQLVESGGGLVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTQVKVSSA |
| 32 | Reference A (89L + 110Q)+ A | EVQLVESGGGLVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTQVQVSSA |
| 33 | Reference A (89L + 112K)+A | EVQLVESGGGLVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTQVTVKSA |

FIG.2-3

| SEQ ID NO | Description | Sequence |
|---|---|---|
| 34 | Reference A (89L + 112Q)+A | EVQLVESGGGLVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTQVTVQSA |
| 35 | Reference A (11V + 89L)+ A | EVQLVESGGGVVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTQVTVSSA |
| 36 | Reference A (11V + 89L + 110K)+ A | EVQLVESGGGVVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTQVKVSSA |
| 37 | Reference A (11V + 89L + 110Q)+ A | EVQLVESGGGVVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTQVQVSSA |
| 38 | Reference A (11V + 89L + 112K)+A | EVQLVESGGGVVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTQVTVKSA |
| 39 | Reference A (11V + 89L + 112Q)+A | EVQLVESGGGVVQAGGSLRLSCAASGGTFSFYGMGWFRQAP GKEQEFVADIRTSAGRTYYADSVKGRFTISRDNAKNTVYLQ MNSLKPEDTALYYCAAEMSGISGWDYWGQGTQVTVQSA |
| 40 | CTLA4 binding moiety/binder | EVQLVESGGGVVQPGGSLRLSCAASGGTFSFYGMGWFRQAP GKEQEFVADIRTSAGRTYYADSVKGRFTISRDNSKNTVYLQM NSLRPEDTALYYCAAEMSGISGWDYWGQGTLVTVSSA |
| 41 | CTLA4 binding moiety/binder | EVQLVESGGGVVQPGGSLRLSCAASGGTFSFYGMGWFRQAP GKEREFVADIRTSAGRTYYADSVKGRFTISRDNSKNTVYLQM NSLRPEDTALYYCAAEMSGISGWDYWGQGTLVTVSSA |
| 42 | CTLA4 binding moiety/binder | DVQLVESGGGVVQPGGSLRLSCAASGGTFSFYGMGWFRQAP GKEQEFVADIRTSAGRTYYADSVKGRFTISRDNSKNTVYLQM NSLRPEDTALYYCAAEMSGISGWDYWGQGTLVTVSSA |
| 43 | CTLA4 binding moiety/binder | DVQLVESGGGVVQPGGSLRLSCAASGGTFSFYGMGWFRQAP GKEREFVADIRTSAGRTYYADSVKGRFTISRDNSKNTVYLQM NSLRPEDTALYYCAAEMSGISGWDYWGQGTLVTVSSA |

FIG.2-4

| SEQ ID NO | Description | Sequence |
|---|---|---|
| 44 | HIS6-FLAG3 tag | HHHHHHGAADYKDHDGDYKDHDIDYKDDDDKGAA |
| 45 | C-terminal end | VTVKS |
| 46 | C-terminal end | VTVQS |
| 47 | C-terminal end | VKVSS |
| 48 | C-terminal end | VQVSS |
| 49 | C-terminal end | VTVKSX(n) |
| 50 | C-terminal end | VTVQSX(n) |
| 51 | C-terminal end | VKVSSX(n) |
| 52 | C-terminal end | VQVSSX(n) |
| 53 | C-terminal end | VTVKSA |
| 54 | C-terminal end | VTVQSA |
| 55 | C-terminal end | VKVSSA |
| 56 | C-terminal end | VQVSSA |
| 57 | C-terminal end | VTVSS |
| 58 | C-terminal end | VTVSSX(n) |
| 59 | C-terminal end | VTVSSA |

FIG.2-5

|  |  | 20 |  | 40 |  | 60 |  |
|---|---|---|---|---|---|---|---|
| SEQIDNO:1 | EVQLVESGGG | LVQAGGSLRL | SCAASGGTFS | FYGMGWFRQA | PGKEQEFVAD | IRTSAGRTYY | 60 |
| SEQIDNO:8 | .......... | .......... | .......... | .......... | .......... | .......... | 60 |
| SEQIDNO:9 | .......... | V......... | .......... | .......... | .......... | .......... | 60 |
| SEQIDNO:10 | .......... | V......... | .......... | .......... | .......... | .......... | 60 |
| SEQIDNO:11 | .......... | V......... | .......... | .......... | .......... | .......... | 60 |
| SEQIDNO:12 | .......... | V......... | .......... | .......... | .......... | .......... | 60 |
| SEQIDNO:13 | .......... | .......... | .......... | .......... | .......... | .......... | 60 |
| SEQIDNO:14 | .......... | .......... | .......... | .......... | .......... | .......... | 60 |
| SEQIDNO:15 | .......... | .......... | .......... | .......... | .......... | .......... | 60 |
| SEQIDNO:16 | .......... | .......... | .......... | .......... | .......... | .......... | 60 |
| SEQIDNO:17 | .......... | V......... | .......... | .......... | .......... | .......... | 60 |
| SEQIDNO:18 | .......... | V......... | .......... | .......... | .......... | .......... | 60 |
| SEQIDNO:19 | .......... | V......... | .......... | .......... | .......... | .......... | 60 |
| SEQIDNO:20 | .......... | V......... | .......... | .......... | .......... | .......... | 60 |
| SEQIDNO:21 | .......... | V......... | .......... | .......... | .......... | .......... | 60 |
| SEQIDNO:22 | .......... | V..P...... | .......... | .......... | .......... | .......... | 60 |
| SEQIDNO:23 | .......... | V..P...... | .......... | .......... | .......R.. | .......... | 60 |
| SEQIDNO:24 | D......... | V..P...... | .......... | .......... | .......... | .......... | 60 |
| SEQIDNO:25 | D......... | V..P...... | .......... | .......... | ....R..... | .......... | 60 |
| SEQIDNO:26 | .......... | .......... | .......... | .......... | .......... | .......... | 60 |
| SEQIDNO:27 | .......... | V......... | .......... | .......... | .......... | .......... | 60 |
| SEQIDNO:28 | .......... | V......... | .......... | .......... | .......... | .......... | 60 |
| SEQIDNO:29 | .......... | V......... | .......... | .......... | .......... | .......... | 60 |
| SEQIDNO:30 | .......... | V......... | .......... | .......... | .......... | .......... | 60 |
| SEQIDNO:31 | .......... | .......... | .......... | .......... | .......... | .......... | 60 |
| SEQIDNO:32 | .......... | .......... | .......... | .......... | .......... | .......... | 60 |
| SEQIDNO:33 | .......... | .......... | .......... | .......... | .......... | .......... | 60 |
| SEQIDNO:34 | .......... | .......... | .......... | .......... | .......... | .......... | 60 |
| SEQIDNO:35 | .......... | V......... | .......... | .......... | .......... | .......... | 60 |
| SEQIDNO:36 | .......... | V......... | .......... | .......... | .......... | .......... | 60 |
| SEQIDNO:37 | .......... | V......... | .......... | .......... | .......... | .......... | 60 |
| SEQIDNO:38 | .......... | V......... | .......... | .......... | .......... | .......... | 60 |
| SEQIDNO:39 | .......... | V......... | .......... | .......... | .......... | .......... | 60 |
| SEQIDNO:40 | .......... | V..P...... | .......... | .......... | .......... | .......... | 60 |
| SEQIDNO:41 | .......... | V..P...... | .......... | .......... | .......R.. | .......... | 60 |
| SEQIDNO:42 | D......... | V..P...... | .......... | .......... | .......... | .......... | 60 |
| SEQIDNO:43 | D......... | V..P...... | .......... | .......... | ....R..... | .......... | 60 |

FIG.3A

```
                      80                 100                120
                       |                  |                  |
SEQIDNO:1  ADSVKGRFTI SRDNAKNTVY LQMNSLKPED TAVYYCAAEM SGISGWDYWG QGTQVTVSS- 119
SEQIDNO:8  .......... .......... .......... ..T....... .......... ..........- 119
SEQIDNO:9  .......... .......... .......... .......... .......... .....K...- 119
SEQIDNO:10 .......... .......... .......... .......... .......... .....Q...- 119
SEQIDNO:11 .......... .......... .......... .......... .......... ........K.- 119
SEQIDNO:12 .......... .......... .......... .......... .......... ........Q.- 119
SEQIDNO:13 .......... .......... .......... ..L....... .......... .....K...- 119
SEQIDNO:14 .......... .......... .......... ..L....... .......... .....Q...- 119
SEQIDNO:15 .......... .......... .......... ..L....... .......... ........K.- 119
SEQIDNO:16 .......... .......... .......... ..L....... .......... ........Q.- 119
SEQIDNO:17 .......... .......... .......... ..L....... .......... ..........- 119
SEQIDNO:18 .......... .......... .......... ..L....... .......... .....K...- 119
SEQIDNO:19 .......... .......... .......... ..L....... .......... .....Q...- 119
SEQIDNO:20 .......... .......... .......... ..L....... .......... ........K.- 119
SEQIDNO:21 .......... .......... .......... ..L....... .......... ........Q.- 119
SEQIDNO:22 .......... ....S..... ......R... ..L....... .......... ...L... .- 119
SEQIDNO:23 .......... ....S..... ......R... ..L....... .......... ...L.....- 119
SEQIDNO:24 .......... ....S..... ......R... ..L....... .......... ...L.....- 119
SEQIDNO:25 .......... ....S..... ......R... ..L....... .......... ...L.....- 119
SEQIDNO:26 .......... .......... .......... ..T....... .......... ..........A 120
SEQIDNO:27 .......... .......... .......... .......... .......... .....K...A 120
SEQIDNO:28 .......... .......... .......... .......... .......... .....Q...A 120
SEQIDNO:29 .......... .......... .......... .......... .......... ........K.A 120
SEQIDNO:30 .......... .......... .......... .......... .......... ........Q.A 120
SEQIDNO:31 .......... .......... .......... ..L....... .......... .....K...A 120
SEQIDNO:32 .......... .......... .......... ..L....... .......... .....Q...A 120
SEQIDNO:33 .......... .......... .......... ..L....... .......... ........K.A 120
SEQIDNO:34 .......... .......... .......... ..L....... .......... ........Q.A 120
SEQIDNO:35 .......... .......... .......... ..L....... .......... ..........A 120
SEQIDNO:36 .......... .......... .......... ..L....... .......... .....K...A 120
SEQIDNO:37 .......... .......... .......... ..L....... .......... .....Q...A 120
SEQIDNO:38 .......... .......... .......... ..L....... .......... ........K.A 120
SEQIDNO:39 .......... .......... .......... ..L....... .......... ........Q.A 120
SEQIDNO:40 .......... ....S..... ......R... ..L....... .......... ...L.....A 120
SEQIDNO:41 .......... ....S..... ......R... ..L....... .......... ...L... .A 120
SEQIDNO:42 .......... ....S..... ......R... ..L....... .......... ...L.....A 120
SEQIDNO:43 .......... ....S..... ......R... ..L....... .......... ...L.....A 120
```

FIG.3B

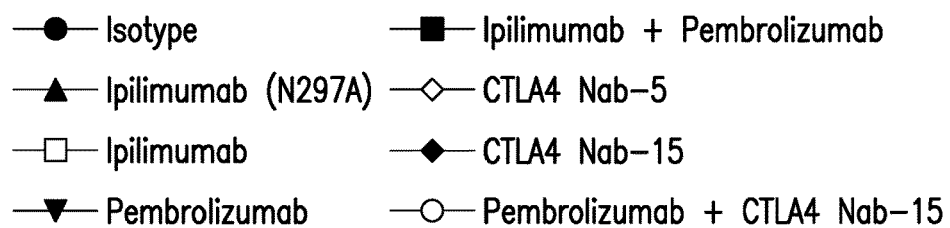
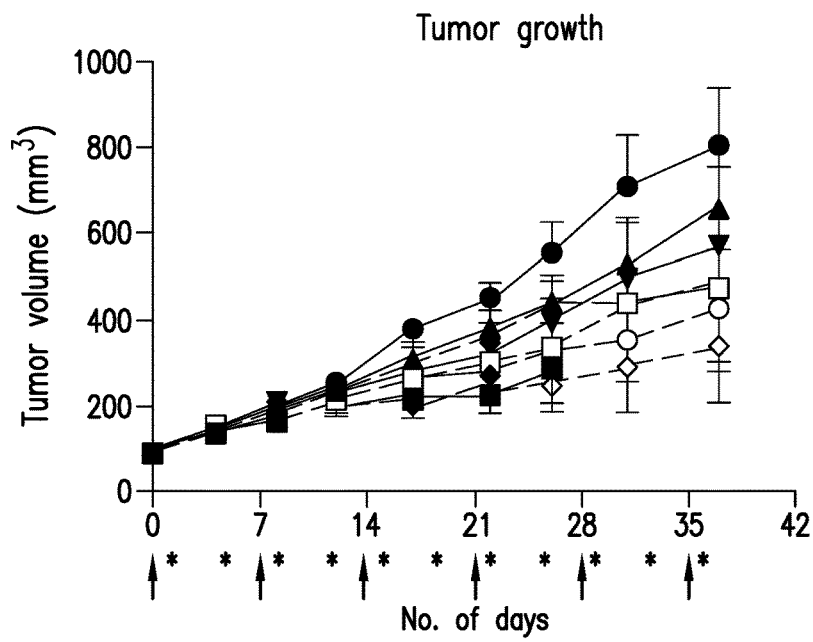
FIG.9A
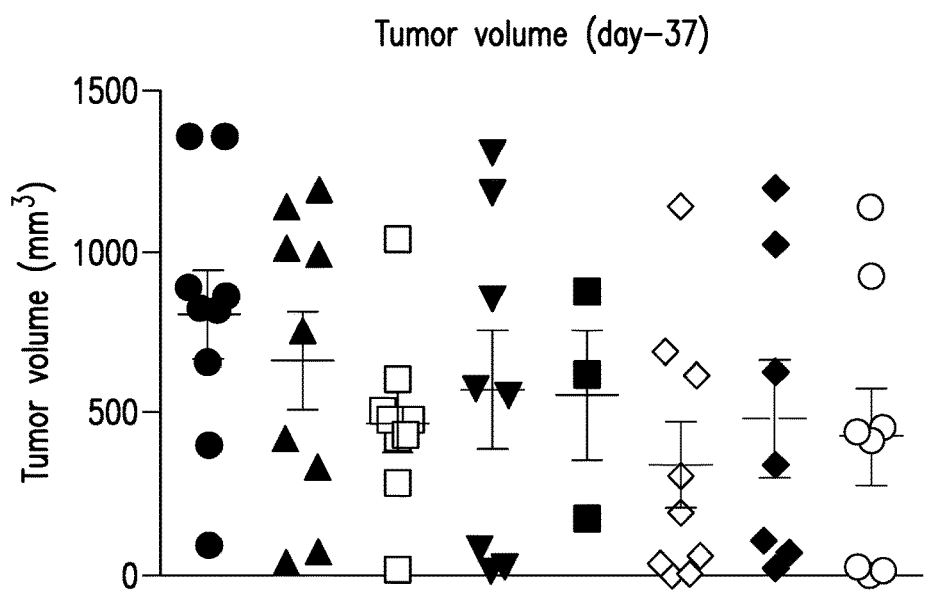
FIG.9B

| NanoBody | Description |
|---|---|
| F023700906 | 4CTLA011F01(L11V,A14P,Q45R,A74S,K83R,V89L,M96P,Q108L)-FLAG3-HIS6 |
| F023700912 | 4CTLA011F01(E1D,L11V,A14P,Q45R,A74S,K83R,V89L,M96P,Q108L)-35GS-4CTLA011F01(L11V,A14P,Q45R,A74S,K83R,V89L,M96P,Q108L)-35GS-ALB11002-A |
| F023700914 | 4CTLA011F01(E1D,L11V,A14P,Q45R,A74S,K83R,V89L,M96P,Q108L)-35GS-ALB11002-A |
| F023701047 | 4CTLA011F01(L11V,A14P,Q45R,N73S,A74S,K83R,V89L,M96P,Q108L)-FLAG3-HIS6 |
| F023701048 | 4CTLA011F01(L11V,A14P,Q45R,N73V,A74S,K83R,V89L,M96P,Q108L)-FLAG3-HIS6 |
| F023701049 | 4CTLA011F01(L11V,A14P,Q45R,N73G,A74S,K83R,V89L,M96P,Q108L)-FLAG3-HIS6 |
| F023701050 | 4CTLA011F01(L11V,A14P,Q45R,N73R,A74S,K83R,V89L,M96P,Q108L)-FLAG3-HIS6 |
| F023701051 | 4CTLA011F01(L11V,A14P,Q45R,N73Q,A74S,K83R,V89L,M96P,Q108L)-FLAG3-HIS6 |
| F023701052 | 4CTLA011F01(L11V,A14P,Q45R,N73M,A74S,K83R,V89L,M96P,Q108L)-FLAG3-HIS6 |
| F023701053 | 4CTLA011F01(L11V,A14P,Q45R,N73H,A74S,K83R,V89L,M96P,Q108L)-FLAG3-HIS6 |
| F023701054 | 4CTLA011F01(L11V,A14P,Q45R,N73T,A74S,K83R,V89L,M96P,Q108L)-FLAG3-HIS6 |
| F023701055 | 4CTLA011F01(L11V,A14P,Q45R,N73D,A74S,K83R,V89L,M96P,Q108L)-FLAG3-HIS6 |
| F023701056 | 4CTLA011F01(L11V,A14P,Q45R,N73E,A74S,K83R,V89L,M96P,Q108L)-FLAG3-HIS6 |
| F023701057 | 4CTLA011F01(L11V,A14P,Q45R,N73W,A74S,K83R,V89L,M96P,Q108L)-FLAG3-HIS6 |
| F023701058 | 4CTLA011F01(L11V,A14P,Q45R,N73F,A74S,K83R,V89L,M96P,Q108L)-FLAG3-HIS6 |
| F023701059 | 4CTLA011F01(L11V,A14P,Q45R,N73K,A74S,K83R,V89L,M96P,Q108L)-FLAG3-HIS6 |
| F023701060 | 4CTLA011F01(L11V,A14P,Q45R,N73A,A74S,K83R,V89L,M96P,Q108L)-FLAG3-HIS6 |
| F023701061 | 4CTLA011F01(L11V,A14P,Q45R,N73Y,A74S,K83R,V89L,M96P,Q108L)-FLAG3-HIS6 |
| F023701062 | 4CTLA011F01(L11V,A14P,Q45R,N73P,A74S,K83R,V89L,M96P,Q108L)-FLAG3-HIS6 |

FIG.11

\>PF023700906.1 4CTLA011F01(L11V,A14P,Q45R,A74S,K83R,V89L,M96P,Q108L)-
FLAG3-HIS6
EVQLVESGGGVVQPGGSLRLSCAASGGTFSFYGMGWFRQAPGKEREFVADIRTSAGRTYYADSVKGRFTISRDNS
KNTVYLQMNSLRPEDTALYYCAAEPSGISGWDYWGQGTLVTVSSAAADYKDHDGDYKDHDIDYKDDDDKGAAHHH
HHH (SEQ ID NO: 93)

\>PF023700912.1 4CTLA011F01(E1D,L11V,A14P,Q45R,A74S,K83R,V89L,M96P,Q108L)-
35GS-4CTLA011F01(L11V,A14P,Q45R,A74S,K83R,V89L,M96P,Q108L)-35GS-ALB11002-A
DVQLVESGGGVVQPGGSLRLSCAASGGTFSFYGMGWFRQAPGKEREFVADIRTSAGRTYYADSVKGRFTISRDNS
KNTVYLQMNSLRPEDTALYYCAAEPSGISGWDYWGQGTLVTVSSGGGGSGGGGSGGGGSGGGGSGGGGSGGGGSG
GGGSEVQLVESGGGVVQPGGSLRLSCAASGGTFSFYGMGWFRQAPGKEREFVADIRTSAGRTYYADSVKGRFTIS
RDNSKNTVYLQMNSLRPEDTALYYCAAEPSGISGWDYWGQGTLVTVSSGGGGSGGGGSGGGGSGGGGSGGGGSGG
GGSGGGGSEVQLVESGGGVVQPGNSLRLSCAASGFTFSSFGMSWVRQAPGKGLEWVSSISGSGSDTLYADSVKGR
FTISRDNAKTTLYLQMNSLRPEDTALYYCTIGGSLSRSSQGTLVTVSSA (SEQ ID NO: 62)

\>F023700914 4CTLA011F01(E1D,L11V,A14P,Q45R,A74S,K83R,V89L,M96P,Q108L)-
35GS-ALB11002-A
DVQLVESGGGVVQPGGSLRLSCAASGGTFSFYGMGWFRQAPGKEREFVADIRTSAGRTYYADSVKGRFTISRDNS
KNTVYLQMNSLRPEDTALYYCAAEPSGISGWDYWGQGTLVTVSSGGGGSGGGGSGGGGSGGGGSGGGGSGGGGSG
GGGSEVQLVESGGGVVQPGNSLRLSCAASGFTFSSFGMSWVRQAPGKGLEWVSSISGSGSDTLYADSVKGRFTIS
RDNAKTTLYLQMNSLRPEDTALYYCTIGGSLSRSSQGTLVTVSSA (SEQ ID NO: 64)

\>PF023701047.1 4CTLA011F01(L11V,A14P,Q45R,N73S,A74S,K83R,V89L,M96P,Q108L)-
FLAG3-HIS6
EVQLVESGGGVVQPGGSLRLSCAASGGTFSFYGMGWFRQAPGKEREFVADIRTSAGRTYYADSVKGRFTISRDSS
KNTVYLQMNSLRPEDTALYYCAAEPSGISGWDYWGQGTLVTVSSAAADYKDHDGDYKDHDIDYKDDDDKGAAHHH
HHH (SEQ ID NO: 94)

\>PF023701048.1 4CTLA011F01(L11V,A14P,Q45R,N73V,A74S,K83R,V89L,M96P,Q108L)-
FLAG3-HIS6
EVQLVESGGGVVQPGGSLRLSCAASGGTFSFYGMGWFRQAPGKEREFVADIRTSAGRTYYADSVKGRFTISRDVS
KNTVYLQMNSLRPEDTALYYCAAEPSGISGWDYWGQGTLVTVSSAAADYKDHDGDYKDHDIDYKDDDDKGAAHHH
HHH (SEQ ID NO: 95)

\>PF023701049.1 4CTLA011F01(L11V,A14P,Q45R,N73G,A74S,K83R,V89L,M96P,Q108L)-
FLAG3-HIS6
EVQLVESGGGVVQPGGSLRLSCAASGGTFSFYGMGWFRQAPGKEREFVADIRTSAGRTYYADSVKGRFTISRDGS
KNTVYLQMNSLRPEDTALYYCAAEPSGISGWDYWGQGTLVTVSSAAADYKDHDGDYKDHDIDYKDDDDKGAAHHH
HHH (SEQ ID NO: 96)

\>PF023701050.1 4CTLA011F01(L11V,A14P,Q45R,N73R,A74S,K83R,V89L,M96P,Q108L)-
FLAG3-HIS6
EVQLVESGGGVVQPGGSLRLSCAASGGTFSFYGMGWFRQAPGKEREFVADIRTSAGRTYYADSVKGRFTISRDRS
KNTVYLQMNSLRPEDTALYYCAAEPSGISGWDYWGQGTLVTVSSAAADYKDHDGDYKDHDIDYKDDDDKGAAHHH
HHH (SEQ ID NO: 97)

FIG.12A

>PF023701051.1 4CTLA011F01(L11V,A14P,Q45R,N73Q,A74S,K83R,V89L,M96P,Q108L)-
FLAG3-HIS6
EVQLVESGGGVVQPGGSLRLSCAASGGTFSFYGMGWFRQAPGKEREFVADIRTSAGRTYYADSVKGRFTISRDQS
KNTVYLQMNSLRPEDTALYYCAAEPSGISGWDYWGQGTLVTVSSAAADYKDHDGDYKDHDIDYKDDDDKGAAHHH
HHH (SEQ ID NO: 98)

>PF023701052.1 4CTLA011F01(L11V,A14P,Q45R,N73M,A74S,K83R,V89L,M96P,Q108L)-
FLAG3-HIS6
EVQLVESGGGVVQPGGSLRLSCAASGGTFSFYGMGWFRQAPGKEREFVADIRTSAGRTYYADSVKGRFTISRDMS
KNTVYLQMNSLRPEDTALYYCAAEPSGISGWDYWGQGTLVTVSSAAADYKDHDGDYKDHDIDYKDDDDKGAAHHH
HHH (SEQ ID NO: 99)

>PF023701053.1 4CTLA011F01(L11V,A14P,Q45R,N73H,A74S,K83R,V89L,M96P,Q108L)-
FLAG3-HIS6
EVQLVESGGGVVQPGGSLRLSCAASGGTFSFYGMGWFRQAPGKEREFVADIRTSAGRTYYADSVKGRFTISRDHS
KNTVYLQMNSLRPEDTALYYCAAEPSGISGWDYWGQGTLVTVSSAAADYKDHDGDYKDHDIDYKDDDDKGAAHHH
HHH (SEQ ID NO: 100)

>PF023701054.1 4CTLA011F01(L11V,A14P,Q45R,N73T,A74S,K83R,V89L,M96P,Q108L)-
FLAG3-HIS6
EVQLVESGGGVVQPGGSLRLSCAASGGTFSFYGMGWFRQAPGKEREFVADIRTSAGRTYYADSVKGRFTISRDTS
KNTVYLQMNSLRPEDTALYYCAAEPSGISGWDYWGQGTLVTVSSAAADYKDHDGDYKDHDIDYKDDDDKGAAHHH
HHH (SEQ ID NO: 101)

>PF023701055.1 4CTLA011F01(L11V,A14P,Q45R,N73D,A74S,K83R,V89L,M96P,Q108L)-
FLAG3-HIS6
EVQLVESGGGVVQPGGSLRLSCAASGGTFSFYGMGWFRQAPGKEREFVADIRTSAGRTYYADSVKGRFTISRDDS
KNTVYLQMNSLRPEDTALYYCAAEPSGISGWDYWGQGTLVTVSSAAADYKDHDGDYKDHDIDYKDDDDKGAAHHH
HHH (SEQ ID NO: 102)

>PF023701056.1 4CTLA011F01(L11V,A14P,Q45R,N73E,A74S,K83R,V89L,M96P,Q108L)-
FLAG3-HIS6
EVQLVESGGGVVQPGGSLRLSCAASGGTFSFYGMGWFRQAPGKEREFVADIRTSAGRTYYADSVKGRFTISRDES
KNTVYLQMNSLRPEDTALYYCAAEPSGISGWDYWGQGTLVTVSSAAADYKDHDGDYKDHDIDYKDDDDKGAAHHH
HHH (SEQ ID NO: 103)

>PF023701057.1 4CTLA011F01(L11V,A14P,Q45R,N73W,A74S,K83R,V89L,M96P,Q108L)-
FLAG3-HIS6
EVQLVESGGGVVQPGGSLRLSCAASGGTFSFYGMGWFRQAPGKEREFVADIRTSAGRTYYADSVKGRFTISRDWS
KNTVYLQMNSLRPEDTALYYCAAEPSGISGWDYWGQGTLVTVSSAAADYKDHDGDYKDHDIDYKDDDDKGAAHHH
HHH (SEQ ID NO: 104)

>PF023701058.1 4CTLA011F01(L11V,A14P,Q45R,N73F,A74S,K83R,V89L,M96P,Q108L)-
FLAG3-HIS6
EVQLVESGGGVVQPGGSLRLSCAASGGTFSFYGMGWFRQAPGKEREFVADIRTSAGRTYYADSVKGRFTISRDFS
KNTVYLQMNSLRPEDTALYYCAAEPSGISGWDYWGQGTLVTVSSAAADYKDHDGDYKDHDIDYKDDDDKGAAHHH
HHH (SEQ ID NO: 105)

FIG. 12B

>PF023701059.1 4CTLA011F01(L11V,A14P,Q45R,N73K,A74S,K83R,V89L,M96P,Q108L)-FLAG3-HIS6
EVQLVESGGGVVQPGGSLRLSCAASGGTFSFYGMGWFRQAPGKEREFVADIRTSAGRTYYADSVKGRFTISRDKS
KNTVYLQMNSLRPEDTALYYCAAEPSGISGWDYWGQGTLVTVSSAAADYKDHDGDYKDHDIDYKDDDDKGAAHHH
HHH (SEQ ID NO: 106)

>PF023701060.1 4CTLA011F01(L11V,A14P,Q45R,N73A,A74S,K83R,V89L,M96P,Q108L)-FLAG3-HIS6
EVQLVESGGGVVQPGGSLRLSCAASGGTFSFYGMGWFRQAPGKEREFVADIRTSAGRTYYADSVKGRFTISRDAS
KNTVYLQMNSLRPEDTALYYCAAEPSGISGWDYWGQGTLVTVSSAAADYKDHDGDYKDHDIDYKDDDDKGAAHHH
HHH (SEQ ID NO: 107)

>PF023701061.1 4CTLA011F01(L11V,A14P,Q45R,N73Y,A74S,K83R,V89L,M96P,Q108L)-FLAG3-HIS6
EVQLVESGGGVVQPGGSLRLSCAASGGTFSFYGMGWFRQAPGKEREFVADIRTSAGRTYYADSVKGRFTISRDYS
KNTVYLQMNSLRPEDTALYYCAAEPSGISGWDYWGQGTLVTVSSAAADYKDHDGDYKDHDIDYKDDDDKGAAHHH
HHH (SEQ ID NO: 108)

>PF023701062.1 4CTLA011F01(L11V,A14P,Q45R,N73P,A74S,K83R,V89L,M96P,Q108L)-FLAG3-HIS6
EVQLVESGGGVVQPGGSLRLSCAASGGTFSFYGMGWFRQAPGKEREFVADIRTSAGRTYYADSVKGRFTISRDPS
KNTVYLQMNSLRPEDTALYYCAAEPSGISGWDYWGQGTLVTVSSAAADYKDHDGDYKDHDIDYKDDDDKGAAHHH
HHH (SEQ ID NO: 109)

FIG.12C

CTLA4 BINDERS

This Application claim the benefit of U.S. Provisional Patent Application No. 62/257,001, filed Nov. 18, 2015; which is herein incorporated by referenced in its entirety.

REFERENCE TO SEQUENCE LISTING SUBMITTED ELECTRONICALLY

The sequence listing of the present application is submitted electronically via EFS-Web as an ASCII formatted sequence listing with a file name "24237 US_NP_SEQTXT_18DECEMBER2018.txt", creation date of Dec. 18, 2018, and a size of 104 Kb. This sequence listing submitted via EFS-Web is part of the specification and is herein incorporated by reference in its entirety.

FIELD OF THE INVENTION

The present invention relates, in part, to amino acid sequences and polypeptides binding to cytotoxic T-lymphocyte-associated protein 4 ("CTLA4"), e.g., human CTLA4. In particular, the present invention relates, in part, to improved heavy-chain immunoglobulin single variable domains (also referred to herein as "ISVs" or "ISVDs") binding to CTLA4, as well as to proteins, polypeptides and other constructs, compounds, molecules or chemical entities that comprise such ISVDs. Other aspects, embodiments, features, uses and advantages of the invention will be clear to the skilled person based on the disclosure herein.

BACKGROUND OF THE INVENTION

Abrogating immune regulatory molecules such as cytotoxic T lymphocyte antigen 4 (CTLA-4) represents a new and promising strategy to induce tumor regression, stabilize disease, and prolong survival by manipulation of the immune system. An anti-CTLA-4 antibody, ipilimumab, is currently being sold for indications including melanoma. Evidence of tumor regression with prolonged time to progression has been seen in patients with melanoma who received CTLA-4 antibodies and durable responses have been observed with ipilimumab in patients with melanoma, ovarian cancer, prostate cancer, and renal cell cancer.

Full T-cell activation requires two signals. The first is initiated by T-cell receptor binding to tumor-associated antigens presented by antigen presenting cells (APCs) via major histocompatibility complexes I and II. The second signal is generated when the principal costimulatory receptor on the T cell, CD28, binds to B7 ligand subtypes CD80 and CD86 on the APC. The resulting dual signaling induces changes including T-cell proliferation and cytokine release, triggering and then amplifying the immune response. In response to T-cell activation, CTLA-4 is upregulated and competes with CD28 for CD80 and CD86 binding on APCs but with significantly higher affinity, therefore downregulating—or deactivating—the T cell (FIG. 1). CTLA-4, therefore, downregulates T-cell responses and APC function, resulting in a decreased immune response to tumor-associated antigens and immune tolerance.

The mechanisms whereby CTLA4 and PD1 exert their inhibitory effects on T-cell activation are multifaceted. CTLA4 functions primarily to limit T-cell activation and clonal expansion, whereas PD1 functions primarily to limit effector T-cell function in the peripheral tissues. Their distinct molecular structures, regulation, signaling pathways, ligand distribution, and function on Tregs and other immune cells suggest that combined therapeutic blockade of CTLA4 and PD1 could synergize to mediate anti-tumor immunity. Intlekofer & Thompson, J. Leuko. Biol. 94(1): 25-39 (2013); Hurwitz et al. Proc. Natl. Acad. Sci. USA 95: 10067-10071 (1998); Parry et al. Mol. Cell. Biol. 25(21): 9543-9553 (2005); Callahan et al. Front. Oncol. Vol 4, Art. 385 (2015).

One method by which to inhibit CTLA4-mediated down-regulation is by interfering with its interaction with its ligands by binding it with a Nanobody. The possibility exists that Nanobodies, originating in llamas, could cause an unwanted anti-drug immune response, e.g., by binding of the Nanobodies by pre-existing antibodies in the patient's serum. Thus, novel methods by which to humanize Nanobodies so as to decrease or eliminate such a response are particularly valuable as are Nanobodies that are created by such methods.

SUMMARY OF THE INVENTION

The present invention provides a multispecific immunoglobulin single variable domain (ISVD) such as a Nanobody that binds to human CTLA4 by contacting human CTLA4 at one or more of the following residues VRVTVL (SEQ ID NO: 118; amino acids 33-38 of SEQ ID NO: 110), ADSQVTEVC (SEQ ID NO: 119; amino acids 41-49 of SEQ ID NO: 110) and CKVELMYPPPYYLG (SEQ ID NO:120; amino acids 93-106 of SEQ ID NO: 110), e.g., all three sites. For example, the binder protects the residues from hydrogen-deuterium exchange in the presence of a deuterium source such as $D_2O$. In an embodiment of the invention, the ISVD binds to human CTLA4 and generates a binding heat map (e.g., as generated in a hydrogen-dueterium exchange assay) essentially as set forth in FIG. 13.

The present invention also provides a CTLA4 binder comprising one or more (e.g., 2) immunoglobulin single variable domains (ISVDs) that bind to human CTLA4 comprising: CDR1 that comprises the amino acid sequence FYGMG (SEQ ID NO: 2; amino acids 6-10 of SEQ ID NO: 5) or GGTFSFYGMG (SEQ ID NO: 5); CDR2 that comprises the amino acid sequence DIRTSAGRTYYADSVKG (SEQ ID NO: 3) or DIRTSAGRTY (SEQ ID NO: 6; amino acids 1-10 of SEQ ID NO: 3); CDR3 that comprises the amino acid sequence EXSGISGWDY (SEQ ID NO: 4; wherein X is M or P); optionally, wherein the ISVD comprises a mutation at residues 11 and 89 (e.g., L11V and/or V89L, for example (E1D, L11V, A14P, Q45R, A74S, K83R, V89L, M96P, Q108L) wherein said residue numbers are Kabat residue numbers.

The present invention provides a CTLA4 binder (e.g., an ISVD, e.g., a Nanobody) comprising CDR1, CDR2 and CDR3 of an immunoglobulin comprising amino acid sequence set forth in SEQ ID NO: 1 wherein said CTLA4 binder comprises at least one mutation with respect to the amino acid sequence set forth in SEQ ID NO: 1 wherein said at least one mutation is at a position selected from the group consisting of 11, 89, 110 and 112, wherein said positions are numbered according to Kabat; and optionally including any number of additional mutations that are set forth herein or otherwise, e.g. up to 10 (e.g., 1, 2, 3, 4, 5, 6, 7, 8, 9 or 10) additional mutations (e.g., point mutations, substitutions, deletions, insertions). For example, in an embodiment of the invention, CDR1 comprises the amino acid sequence: FYGMG (SEQ ID NO: 2) or GGTFSFYGMG (SEQ ID NO: 5); CDR2 comprises the amino acid sequence: DIRTSAGRTYYADSVKG (SEQ ID NO: 3) or DIRTSAGRTY (SEQ ID NO: 6); and CDR3 comprises the amino acid sequence:

EMSGISGWDY (SEQ ID NO: 115). For example, in an embodiment of the invention, the CTLA4 binder has a mutation relative to SEQ ID NO: 1 wherein the amino acid residue at position 11 is chosen from L or V; the amino acid residue at position 89 is suitably chosen from T, V or L; the amino acid residue at position 110 is suitably chosen from T, K or Q; and/or the amino acid residue at position 112 is suitably chosen from S, K or Q; e.g., wherein the mutation is 89T; 89L in combination with 11V; 89L in combination with 110K or 110Q; 89L in combination with 112K or 112Q; 89L in combination with 11V and 110K or 110Q; 89L in combination with 11V and 112K or 112Q; 11V in combination with 110K or 110Q; and/or 11V in combination with 112K or 112Q. In an embodiment of the invention, the mutation at positions 11, 89, 110 and/or 112 is as set forth in Table B. In an embodiment of the invention, the CTLA4 binder further comprises one or more mutations, relative to the SEQ ID NO: 1, at positions 1, 14, 45, 74, 83 and/or 108. In an embodiment of the invention, the CTLA4 binder has a C-terminal extension of 1, 2, 3, 4, 5, 6, 7, 8, 9 or 10 amino acids. For example, in the embodiment of the invention, the C-terminal extension has the formula —X(n), wherein X and n are as follows: (a) n=1 and X=Ala; (b) n=2 and each X=Ala; (c) n=3 and each X=Ala; (d) n=2 and at least one X=Ala (with the remaining amino acid residue(s) X being independently chosen from any naturally occurring amino acid); (e) n=3 and at least one X=Ala (with the remaining amino acid residue(s) X being independently chosen from any naturally occurring amino acid); (f) n=3 and at least two X=Ala (with the remaining amino acid residue(s) X being independently chosen from any naturally occurring amino acid); (g) n=1 and X=Gly; (h) n=2 and each X=Gly; (i) n=3 and each X=Gly; (j) n=2 and at least one X=Gly (with the remaining amino acid residue(s) X being independently chosen from any naturally occurring amino acid); (k) n=3 and at least one X=Gly (with the remaining amino acid residue(s) X being independently chosen from any naturally occurring amino acid); (l) n=3 and at least two X=Gly (with the remaining amino acid residue(s) X being independently chosen from any naturally occurring amino acid); (m) n=2 and each X=Ala or Gly; (n) n=3 and each X=Ala or Gly; (o) n=3 and at least one X=Ala or Gly (with the remaining amino acid residue(s) X being independently chosen from any naturally occurring amino acid); or (p) n=3 and at least two X=Ala or Gly (with the remaining amino acid residue(s) X being independently chosen from any naturally occurring amino acid). For example, in an embodiment of the invention, the C-terminal extension is A, AA, AAA, G, GG, GGG, AG, GA, AAG, AGG, AGA, GGA, GAA or GAG. The present invention includes a CTLA4 binder (e.g., an ISVD such as a Nanobody) which comprises an amino acid sequence having at least 85% (e.g., 85, 86, 87, 88, 89, 90, 91, 92, 93, 94, 95, 96, 97, 98, 99, 99.5, 99.9 or 100%) sequence identity with the amino acid sequence set forth in a member selected from the group consisting of SEQ ID NOs: 8-43 wherein the CTLA4 binder or ISVD comprises CDR1, CDR2 and CDR3 of an immunoglobulin comprising an amino acid sequence set forth in SEQ ID NO: 1 wherein said CTLA4 binder or ISVD comprises at least one mutation with respect to the amino acid sequence set forth in SEQ ID NO: 1 wherein said at least one mutation is at a position selected from the group consisting of 11, 89, 110 and 112, wherein said positions are numbered according to Kabat. The present invention also provides a CTLA4 binder, ISVD, Nanobody or polypeptide comprising the amino acid sequence selected from the group consisting of SEQ ID NOs: 9-40. The present invention also provides a multispecific binder comprising a CTLA4 binding moiety (e.g., an ISVD such as a Nanobody) that binds to CTLA4 which is linked to one or more molecules that bind to an epitope that is not the epitope to which the CTLA4 binding moiety binds (e.g., PD1, CTLA4, LAGS, BTLA and/or CD27).

The present invention also provides any such CTLA4 binder, polypeptide, immunoglobulin single variable domain (ISVD) or multispecific binder which is in association with a further therapeutic agent.

The present invention also provides an injection device (e.g., hypodermic needle and syringe) or vessel that comprises the CTLA4 binder, immunoglobulin single variable domain (ISVD), Nanobody, polypeptide or multispecific binder optionally in association with a further therapeutic agent.

The present invention also provides a polynucleotide encoding the CTLA4 binder, immunoglobulin single variable domain (ISVD), Nanobody, polypeptide or multispecific binder, e.g., which is in a vector. The present invention also provides a host cell (e.g., a CHO cell or *Pichia* cell) comprising the polynucleotide or vector.

The present invention also provides a method for making an CTLA4 binder, immunoglobulin single variable domain (ISVD), Nanobody, polypeptide or multispecific binder comprising introducing a polynucleotide encoding the CTLA4 binder, immunoglobulin single variable domain (ISVD), Nanobody, polypeptide or multispecific binder into a host cell (e.g., a CHO cell or *Pichia* cell) and culturing the host cell in a medium under conditions favorable to expression of said immunoglobulin from said polynucleotide and, optionally, purifying the immunoglobulin from said host cell and/or said medium. Any immunoglobulin single variable domain (ISVD), Nanobody, polypeptide, multispecific binder or CTLA4 binder produced by such a method.

The present invention also provides a method for preventing CTLA4 on a T-cell from binding to CD80 and/or CD86 on an antigen-presenting cell comprising contacting said CTLA4 with an immunoglobulin single variable domain (ISVD), Nanobody, polypeptide, multispecific binder or CTLA4 binder optionally in association with a further therapeutic agent. The present invention also provides a method for enhancing an immune response in the body of a subject comprising administering an effective amount of an immunoglobulin single variable domain (ISVD), Nanobody, polypeptide, multispecific binder or CTLA4 binder to the subject (e.g., mammal such as a human) optionally in association with a further therapeutic agent. The present invention also provides a method for treating or preventing cancer or an infectious disease in the body of a subject comprising administering an effective amount of an immunoglobulin single variable domain (ISVD), Nanobody, polypeptide, multispecific binder or CTLA4 binder optionally in association with a further therapeutic agent to the subject. In an embodiment of the invention, the cancer is metastatic cancer, a solid tumor, a hematologic cancer, leukemia, lymphoma, osteosarcoma, rhabdomyosarcoma, neuroblastoma, kidney cancer, leukemia, renal transitional cell cancer, bladder cancer, Wilm's cancer, ovarian cancer, pancreatic cancer, breast cancer, prostate cancer, bone cancer, lung cancer, non-small cell lung cancer, gastric cancer, colorectal cancer, cervical cancer, synovial sarcoma, head and neck cancer, squamous cell carcinoma, multiple myeloma, renal cell cancer, retinoblastoma, hepatoblastoma, hepatocellular carcinoma, melanoma, rhabdoid tumor of the kidney, Ewing's sarcoma, chondrosarcoma, brain cancer, glioblastoma, meningioma, pituitary adenoma, vestibular schwannoma, a primitive neuroectodermal tumor, medulloblastoma, astrocytoma, anaplastic astrocytoma, oligodendroglioma, ependymoma, choroid plexus papilloma, polycythemia vera, thrombocythemia, idiopathic myelfibrosis, soft tissue sarcoma, thyroid cancer, endometrial cancer, carcinoid cancer or liver cancer, breast cancer or gastric cancer. In an embodiment of the invention, the infectious disease is a bacterial infection, a viral infection or a fungal infection. For example, in an embodiment of the invention, the subject is administered a further therapeutic agent or a therapeutic procedure in association with the immunoglobulin single variable domain (ISVD), Nanobody, polypeptide, multispecific binder or CTLA4 binder.

The present invention proviees a CTLA4 binder (e.g., a multivalent binder) comprising an immunoglobulin single variable domain (ISVD) that binds to human CTLA4 by contacting human CTLA4 at one or more of the following residues: VRVTVL, (SEQ ID NO: 118; amino acids 33-38 of SEQ ID NO: 110), ADSQVTEVC (SEQ ID NO: 119; amino acids 41-49 of SEQ ID NO: 110) and CKVELMYPPPYYLG (SEQ ID NO:120; amino acids 93-106 of SEQ ID NO: 110); wherein the ISVD comprises a mutation at residues 11 (e.g., L11V) and 89 (e.g., V89L) wherein said residue numbers are Kabat residue numbers.

The present invention also provides a CTLA4 binder (e.g., a multivalent binder) comprising an immunoglobulin single variable domain (ISVD) that binds to CTLA4 comprising the amino acid sequence set forth in SEQ ID NO: 1 but comprising one or more mutations at a position selected from the group consisting of E1, L11, A14, Q45, A74, N73, K83, V89, M96 or Q108L (e.g., E1D, L11V, A14P, Q45R, A74S, N73X (wherein X is S, V, G, R, Q, M, H, T, D, E, W, F, K, A, Y or P), K83R, V89L, M96P, Q108L); wherein said residue numbers are Kabat residue numbers; and, optionally, a half-life extender (e.g., ALB11002) and/or a C-terminal extender (e.g., an Alanine). For example, in an embodiment of the invention, the the ISVD comprises the amino acid sequence: XVQLVESGGGVVQPGGSLRLSCAASGGTF-SFYGMGWFRQAPGKEREFVADIRTSAGRTYYADSV-KGRFTISRDNSKNTVYLQMNSLRPEDTALYYCAAE-PSGISGWDYWGQGT LVTVSS, wherein X is D or E (SEQ ID NO: 60); optionally comprising a half-life extender (e.g., ALB11002) and/or a C-terminal extender (e.g., an Alanine). In an embodiment of the invention, the CTLA4 binder comprises an ISVD that includes the amino acid sequence selected from SEQ ID NOs: 93-109; optionally lacking amino acids AAADYKDHDGDYKDHDI-DYKDDDDKGAAHHHHHH thereof. In an embodiment of the invention, the CTLA4 binder comprises an ISVD that binds to CTLA4 comprising the amino acid sequence set forth in SEQ ID NO: 60 wherein X is D or E; a peptide linker (e.g., GGGGSGGGGSGGGGSGGGGSGGGGSGGGGSGGGGS (SEQ ID NO: 65)); an ISVD that binds to CTLA4 comprising the amino acid sequence set forth in SEQ ID NO: 60 wherein X is D or E; a peptide linker; a half-life extender; and, optionally, a C-terminal extension alanine; or wherein the CTLA4 binder comprises an ISVD that binds to CTLA4 comprising the amino acid sequence set forth in SEQ ID NO: 60 wherein X is D or E; a peptide linker; a half-life extender; and, optionally, a C-terminal extension alanine. In an embodiment of the invention, the CTLA4 binder comprises the amino acid sequence:

(SEQ ID NO: 62)
DVQLVESGGGVVQPGGSLRLSCAASGGTFSFYGMG

WFRQAPGKEREFVADIRTSAGRTYYADSVKGRFTISRDNSKNTVYLQMNS

LRPEDTALYYCAAEPSGISGWDYWGQGTLVTVSSGGGGSGGGGSGGGGSG

GGGSGGGGSGGGGSGGGGSEVQLVESGGGVVQPGGSLRLSCAASGGTFSF

YGMGWFRQAPGKEREFVADIRTSAGRTYYADSVKGRFTISRDNSKNTVYL

QMNSLRPEDTALYYCAAEPSGISGWDYWGQGTLVTVSSGGGGSGGGGSGG

GGSGGGGSGGGGSGGGGSGGGGSEVQLVESGGGVVQPGNSLRLSCAASGF

TFSSFGMSWVRQAPGKGLEWVSSISGSGSDTLYADSVKGRFTISRDNAKT

TLYLQMNSLRPEDTALYYCTIGGSLSRSSQGTLVTVSSA;
or (SEQ ID NO: 64)
DVQLVESGGGVVQPGGSLRLSCAASGGTFSFYGMG

WFRQAPGKEREFVADIRTSAGRTYYADSVKGRFTISRDNSKNTVYLQMNS

LRPEDTALYYCAAEPSGISGWDYWGQGTLVTVSSGGGGSGGGGSGGGGSG

GGGSGGGGSGGGGSGGGGSEVQLVESGGGVVQPGNSLRLSCAASGFTFSS

FGMSWVRQAPGKGLEWVSSISGSGSDTLYADSVKGRFTISRDNAKTTLYL

QMNSLRPEDTALYYCTIGGSLSRSSQGTLVTVSSA.

The present invention also provides a binder (e.g., an antibody) that cross-blocks a CTLA4 binder set forth herein from binding to CTLA4.

The present invention also provides an injection device or vessel that comprises any CTLA4 binder set forth herein (e.g., comprising the amino acid sequence set forth in SEQ ID NO: 62 or 64) optionally in association with a further therapeutic agent.

The present invention also provides a polynucleotide (e.g., DNA) encoding any CTLA4 binder set forth herein (e.g., comprising the amino acid sequence set forth in SEQ ID NO: 62 or 64); e.g., comprising the nucleotide sequence of SEQ ID NO: 61 or 63; or a vector comprising such a polynucleotide; or a host cell comprising such a polynucleotide or vector.

The present invention also provides a method for making the CTLA4 binder set forth herein (e.g., comprising the amino acid sequence set forth in SEQ ID NO: 62 or 64) comprising introducing a polynucleotide encoding the CTLA4 binder into a host cell (e.g., a CHO cell or Pichia cell) and culturing the host cell in a medium under conditions favorable to expression of said CTLA4 binder from said polynucleotide and, optionally, purifying the CTLA4 binder from said host cell and/or said medium as well as any CTLA4 binder produced by such a method.

The present invention also provides a method for preventing CTLA4 from binding to CD80 or CD86 (e.g., in the body of a subject) comprising contacting said CTLA4 with the CTLA4 binder (e.g., comprising the amino acid sequence set forth in SEQ ID NO: 62 or 64) optionally in association with a further therapeutic agent; as well as a method for enhancing an immune response in the body of a subject (e.g., a human) comprising administering an effective amount of the CTLA4 binder (e.g., comprising the amino acid sequence set forth in SEQ ID NO: 62 or 64) to the subject optionally in association with a further therapeutic agent (e.g., pembrolizumab). In addition, the present invention provides a method for treating or preventing cancer or an infectious disease in the body of a subject comprising administering an effective amount of CTLA4 binder (e.g., comprising the amino acid sequence set forth in SEQ ID NO: 62 or 64) optionally in association with a further therapeutic agent (e.g., pembrolizumab) to the subject. In an embodiment of the invention, the cancer is metastatic cancer, a solid tumor, a hematologic cancer, leukemia, lymphoma, osteosarcoma, rhabdomyosarcoma, neuroblastoma, kidney cancer, leukemia, renal transitional cell cancer, bladder cancer, Wilm's cancer, ovarian cancer, pancreatic cancer, breast cancer, prostate cancer, bone cancer, lung cancer, non-small cell lung cancer, gastric cancer, colorectal cancer, cervical cancer, synovial sarcoma, head and neck cancer, squamous cell carcinoma, multiple myeloma, renal cell cancer, retinoblastoma, hepatoblastoma, hepatocellular carcinoma, melanoma, rhabdoid tumor of the kidney, Ewing's sarcoma, chondrosarcoma, brain cancer, glioblastoma, meningioma, pituitary adenoma, vestibular schwannoma, a primitive neuroectodermal tumor, medulloblastoma, astrocytoma, anaplastic astrocytoma, oligodendroglioma, ependymoma, choroid plexus papilloma, polycythemia vera, thrombocythemia, idiopathic myelfibrosis, soft tissue sarcoma, thyroid cancer, endometrial cancer, carcinoid cancer or liver cancer, breast cancer or gastric cancer; or wherein the infectious disease is a bacterial infection, a viral infection or a fungal infection. In an embodiment of the invention, the subject is administered a further therapeutic agent (e.g., pembrolizumab) or a therapeutic procedure in association with the CTLA4 binder.

DESCRIPTION OF THE FIGURES

FIG. 1. A table listing some of the amino acid positions that will be specifically referred to herein and their numbering according to some alternative numbering systems (such as Aho and IMGT)

FIG. 2-1-2-5. CTLA4 binder sequences.

FIG. 3 (A-B). Alignment of 11F1 sequence with that of the SEQ ID NOs: 8-43.

FIG. 4. Predominant N-linked glycans for monoclonal antibodies produced in Chinese hamster ovary cells (CHO N-linked glycans) and in engineered yeast cells (engineered yeast N-linked glycans): squares: N-acetylglucosamine (GlcNac); circles: mannose (Man); diamonds: galactose (Gal); triangles: fucose (Fuc).

FIG. 5 (A-B). bFACS analysis of Nanobody F023700912, F023700925 or control nanobody (IRR00051; anti-HER2/ERBB2 (bivalent anti-HER2 with 35GS connected to albumin binder)) binding to (A) Jurkat and (B) CHO-K1 cells expressing hCTLA4.

FIG. 11. CTLA4 binder constructs.

FIG. 12 (A-C). CTLA4 binder sequences.

DETAILED DESCRIPTION OF THE INVENTION

Figure 10A:
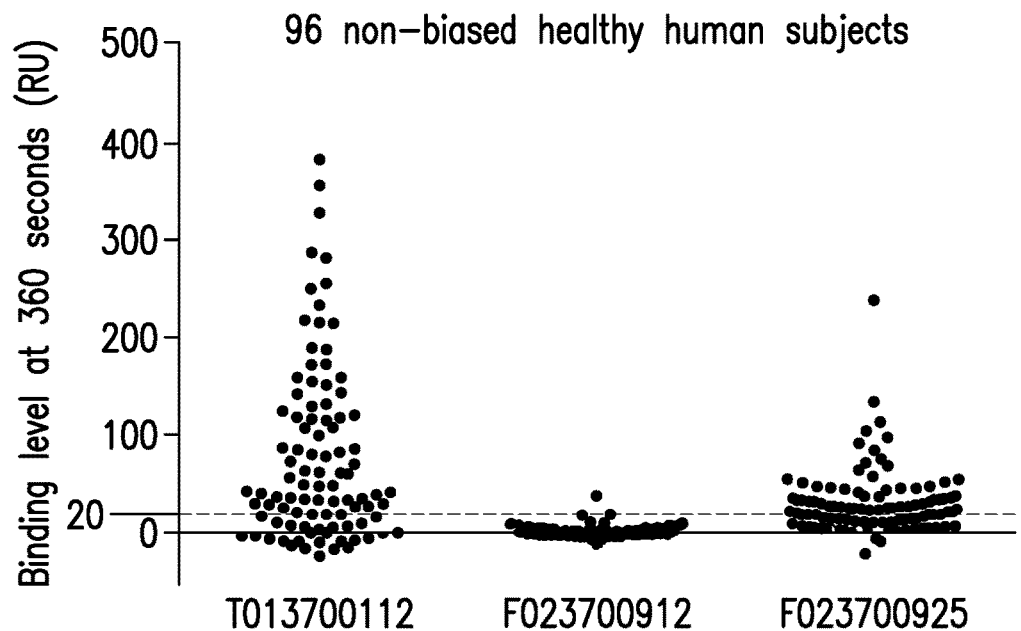
FIG. 10 (A-B). Serum preAb reactivity to F023700912 and F023700925 and a trivalent control Nanobody T013700112 (lacking mutations to reduce pre-existing antibody binding) by (A) healthy human subject sera and (B) cancer patient sera.
Figure 10B:
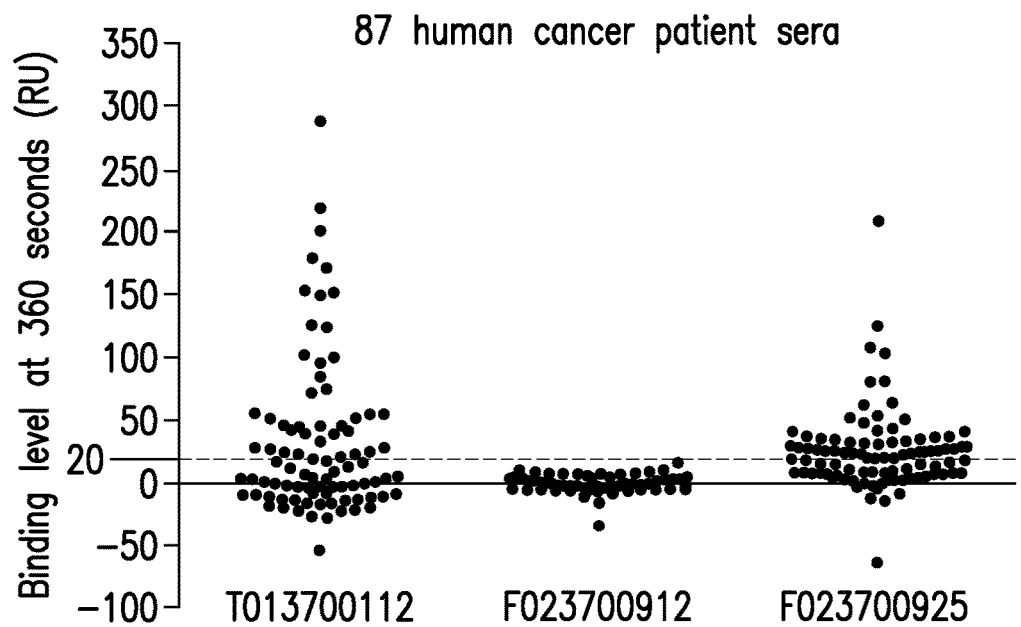

The present invention provides ISVDs that comprise mutations which block reactivity of pre-existing antibodies (pre-antibodies) to neo-epitopes within the ISVDs. Neoepitopes are epitopes within a protein which are revealed when the protein is mutated (e.g., truncated) or its folding is altered. Pre-existing antibodies are antibodies existing in the body of a patient prior to receipt of an ISVD. The ISVDs of the present invention are based, in part, in llama antibodies whose C-terminal constant domains have been removed; thus, exposing the neo-epitopes in the C-terminus of the resulting VHH to pre-antibody binding. It has been discovered that the combination of mutations of residues 11 and 89 (e.g., L11V and I89L or V89L) led to a surprising lack of pre-antibody binding. Mutations in residue 112 have also been shown to remarkably reduce pre-antibody binding. Buyse & Boutton (WO2015/173325) included data showing that the combination of an L11V and V89L mutation provided a remarkable improvement in reducing pre-antibody binding compared to an L11V mutation alone or a V89L mutation alone. For example, Table H of Buyse & Boutton on page 97 showed comparative data for an ISVD with a V89L mutation alone (with or without C-terminal extension) and the same ISVD with a V89L mutation in combination with an L11V mutation (again, with or without a C-terminal extension). Also, although generated in two separate experiments, the data shown in Table H for the L11V/V89L combination as compared to the data given in Table B for an L11V mutation alone (in the same ISVD) showed that the pre-antibody binding reduction that is obtained by the L11v/N89L combination was greater than that for the L11V mutation alone. Since the llama antibody scaffold structure is known to be very highly conserved, the effect of the mutations at positions 11 and 89 is very likely to exist for any ISVD. Indeed, the effect was demonstrated, in FIG. 10, with the instant binders, F023700912 and F023700925, which were shown to exhibit very low levels of pre-antibody binding.

In the present application, the amino acid residues/positions in an immunoglobulin heavy-chain variable domain will be indicated with the numbering according to Kabat. For the sake of convenience, FIG. 1 gives a table listing some of the amino acid positions that will be specifically referred to herein and their numbering according to some alternative numbering systems (such as Aho and IMGT. Note: unless explicitly indicated otherwise, for the present description and claims, Kabat numbering is decisive; other numbering systems are given for reference only).

With regards to the CDRs, as is well-known in the art, there are multiple conventions to define and describe the CDRs of a VH or VHH fragment, such as the Kabat definition (which is based on sequence variability and is the most commonly used) and the Chotia definition (which is based on the location of the structural loop regions). Reference is for example made to the website www.bioinf.org.uk/abs/. For the purposes of the present specification and claims, even though the CDRs according to Kabat may also be mentioned, the CDRs are most preferably defined on the basis of the Abm definition (which is based on Oxford Molecular's AbM antibody modelling software), as this is considered to be an optimal compromise between the Kabat and Chotia definitions. Reference is again made to the website www.bioinf.org.uk/abs/. See Sequences of Proteins of Immunological Interest, Kabat, et al.; National Institutes of Health, Bethesda, Md.; 5th ed.; NIH Publ. No. 91-3242 (1991); Kabat (1978) Adv. Prot. Chem. 32:1-75; Kabat, et al., (1977) J. Biol. Chem. 252:6609-6616; Chothia, et al., (1987) J Mol. Biol. 196:901-917 or Chothia, et al., (1989) Nature 342:878-883; Chothia & Lesk (1987) J. Mol. Biol. 196: 901-917; Elvin A. Kabat, Tai Te Wu, Carl Foeller, Harold M. Perry, Kay S. Gottesman (1991) Sequences of Proteins of Immunological Interest; Protein Sequence and Structure Analysis of Antibody Variable Domains. In: Antibody Engineering Lab Manual (Ed.: Duebel, S. and Kontermann, R., Springer-Verlag, Heidelberg). In an embodiment of the invention, CDR determination is according to Kabat, e.g., wherein FR1 of a VHH comprises the amino acid residues at positions 1-30, CDR1 of a VHH comprises the amino acid residues at positions 31-35, FR2 of a VHH comprises the amino acids at positions 36-49, CDR2 of a VHH comprises the amino acid residues at positions 50-65, FR3 of a VHH comprises the amino acid residues at positions 66-94, CDR3 of a VHH comprises the amino acid residues at positions 95-102, and FR4 of a VHH comprises the amino acid residues at positions 103-113.

In an embodiment of the invention, CDRs are determined according to Kontermann and Dübel (Eds., Antibody Engineering, vol 2, Springer Verlag Heidelberg Berlin, Martin, Chapter 3, pp. 33-51, 2010).

The term "immunoglobulin single variable domain" (also referred to as "ISV" or "ISVD") is generally used to refer to immunoglobulin variable domains (which may be heavy chain or light chain domains, including VH, VHH or VL domains) that can form a functional antigen-binding site without interaction with another variable domain (e.g. without a VH/VL interaction as is required between the VH and VL domains of conventional 4-chain monoclonal antibody). Examples of ISVDs will be clear to the skilled person and for example include Nanobodies (including a VHH, a humanized VHH and/or a camelized VHs such as camelized human VHs), IgNAR, domains, (single domain) antibodies (such as dAbs™) that are VH domains or that are derived from a VH domain and (single domain) antibodies (such as dAbs™) that are VL domains or that are derived from a VL domain. ISVDs that are based on and/or derived from heavy chain variable domains (such as VH or VHH domains) are generally preferred. Most preferably, an ISVD will be a Nanobody. For example, F023700906 is an ISVD.

The term "Nanobody" is generally as defined in WO 2008/020079 or WO 2009/138519, and thus in a specific aspect generally denotes a VHH, a humanized VHH or a camelized VH (such as a camelized human VH) or generally a sequence optimized VHH (such as e.g. optimized for chemical stability and/or solubility, maximum overlap with known human framework regions and maximum expression). It is noted that the terms Nanobody or Nanobodies are registered trademarks of Ablynx N.V. and thus may also be referred to as Nanobody® and/or Nanobodies®).

A multispecific binder is a molecule that comprises a first CTLA4 binding moiety (e.g., an ISVD or a Nanobody) and one or more (e.g., 1, 2, 3, 4, 5) additional binding moieties (e.g., an ISVDs or Nanobodies) that bind to an epitope other than that of the first CTLA4 binding moiety (e.g., a different epitope of CTLA4, or to CD27, LAG3, PD1 or BTLA).

A binding moiety or binding domain or binding unit is a molecule, such as an ISVD or Nanobody (e.g., any of SEQ ID NOs: 8-43 or 60), that binds to an antigen such as CTLA4. A binding moiety or binding domain or binding unit may be part of a larger molecule such as a multivalent or multispecific binder that includes more than one moiety, domain or unit which may comprises another functional element, such as, for example, a half-life extender (HLE), targeting unit and/or a small molecule such a polyethyleneglycol (PEG).

A monovalent CTLA4 binder (e.g., ISVD such as a Nanobody) is a molecule that comprises a single antigen-binding domain. A bivalent CTLA4 binder (e.g., ISVD such as a Nanobody) comprises two antigen-binding domains. A multivalent CTLA4 binder comprises more than one antigen-binding domain (e.g., 1, 2, 3, 4, 5, 6, or 7).

A monospecific CTLA4 binder (e.g., ISVD such as a Nanobody) binds a single antigen (CTLA4); a bispecific CTLA4 binder binds to two different antigens and a multispecific CTLA4 binder binds to more than one antigen.

A biparatopic CTLA4 binder (e.g., ISVD such as a Nanobody) is monospecific but binds to two different epitopes of the same antigen. A multiparatopic CTLA4 binder binds the same antigen but to more than one epitope in the antigen.

The term "half-life" as used herein in relation to a CTLA4 binder (e.g., ISVD such as a Nanobody) or other molecule can generally be defined as described in paragraph o) on page 57 of WO 2008/020079 and as mentioned therein refers to the time taken for the serum concentration of the amino acid sequence, CTLA4 binder, compound or polypeptide to be reduced by 50%, in vivo, for example due to degradation of the sequence or compound and/or clearance or sequestration of the sequence or compound by natural mechanisms. The in vivo half-life of an amino acid sequence, CTLA4 binder, compound or polypeptide of the invention can be determined in any manner known per se, such as by pharmacokinetic analysis. Suitable techniques will be clear to the person skilled in the art, and may for example generally be as described in paragraph o) on page 57 of WO 2008/020079. As also mentioned in paragraph o) on page 57 of WO 2008/020079, the half-life can be expressed using parameters such as the t1/2-alpha, t1/2-beta and the area under the curve (AUC). In this respect it should be noted that the term "half-life" as used herein in particular refers to the t1/2-beta or terminal half-life (in which the t1/2-alpha and/or the AUC or both may be kept out of considerations). Reference is for example made to the Experimental Part below, as well as to the standard handbooks, such as Kenneth, A et al: Chemical Stability of Pharmaceuticals: A Handbook for Pharmacists and Peters et al, Pharmacokinete analysis: A Practical Approach (1996). Reference is also made to "Pharmacokinetics", M Gibaldi & D Perron, published by Marcel Dekker, 2nd Rev. edition (1982). Similarly, the terms "increase in half-life" or "increased half-life" are also as defined in paragraph o) on page 57 of WO 2008/

020079 and in particular refer to an increase in the t1/2-beta, either with or without an increase in the t1/2-alpha and/or the AUC or both.

When a term is not specifically defined herein, it has its usual meaning in the art, which will be clear to the skilled person. Reference is for example made to the standard handbooks, such as Sambrook et al, "Molecular Cloning: A Laboratory Manual" (2nd.Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, Calif. (1981); Roitt et al., "Immunology" (6th. Ed.), Mosby/Elsevier, Edinburgh (2001); Roitt et al., Roitt's Essential Immunology, 10th Ed. Blackwell Publishing, UK (2001); and Janeway et al., "Immunobiology" (6th Ed.), Garland Science Publishing/Churchill Livingstone, New York (2005), as well as to the general background art cited herein.

For a general description of multivalent and multispecific polypeptides containing one or more Nanobodies and their preparation, reference is also made to Conrath et al., J. Biol. Chem., Vol. 276, 10. 7346-7350, 2001; Muyldermans, Reviews in Molecular Biotechnology 74 (2001), 277-302; as well as to for example WO 1996/34103, WO 1999/23221, WO 2004/041862, WO 2006/122786, WO 2008/020079, WO 2008/142164 or WO 2009/068627.

"Isolated" CTLA4 binders (e.g., ISVD such as a Nanobody), polypepetides, polynucleotides and vectors, are at least partially free of other biological molecules from the cells or cell culture from which they are produced. Such biological molecules include nucleic acids, proteins, lipids, carbohydrates, or other material such as cellular debris and growth medium. An "isolated" CTLA4 binder may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the antibodies or fragments.

The phrase "control sequences" refers to polynucleotides necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid or polynucleotide is "operably linked" when it is placed into a functional relationship with another polynucleotide. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, but not always, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Human serum albumin binders" or "HSA binders" of the present invention are any of the molecules described herein that bind to HSA (e.g., an ISVD such as a Nanobody) as well as any antibody or antigen-binding fragment thereof that binds to HSA and includes any of the HSA binding moieties described herein. An individual HSA binder may be referred to has a HSA binding moiety if it is part of a larger molecule, e.g., a multivalent molecule such as F023700912 or F023700914

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989).

Examples of antigen-binding fragments include, but are not limited to, Fab, Fab', F(ab')$_2$, and Fv fragments, and single-chain Fv molecules.

The following properties are associated with the indicated mutations in the CTLA4 binder 11F01:

E1D: Prevent pyroglutamic acid formation in the first amino acid of the construct E1
L11V: Decrease pre-antibody binding
A14P: Humanization
Q45R: Mutated to increase stability
A74S: Humanization
K83R: Humanization
I89L: Decrease pre-antibody binding
M96P,Q or R: Prevent oxidation of M96
Q108L: Humanization In an embodiment of the invention, CTLA4 is human CTLA4. In an embodiment of the invention, human CTLA4 comprises the amino acid sequence:

```
                                        (SEQ ID NO: 111)
MACLGFQRHK AQLNLATRTW PCTLLFFLLF IPVFCKAMHV

AQPAVVLASS RGIASFVCEY ASPGKATEVR VTVLRQADSQ

VTEVCAATYM MGNELTFLDD SICTGTSSGN QVNLTIQGLR

AMDTGLYICK VELMYPPPYY LGIGNGTQIY VIDPEPCPDS

DFLLWILAAV SSGLFFYSFL LTAVSLSKML KKRSPLTTGV

YVKMPPTEPE CEKQFQPYFI PIN
```

CTLA4 Binders

The present invention aims to provide improved CTLA4 binders, in particular improved CTLA4 ISVDs and more in particular improved CTLA4 Nanobodies. CTLA4 binders of the present invention include polypeptides which are variants of polypeptides comprising the amino acid sequence of SEQ ID NO: 1 which is mutated at position such as 1, 11, 14, 45, 74, 83, 89, 96, 108, 110 and/or 112.

A CTLA4 binder or CTLA4 ISVD or CTLA4 Nanobody refers to a binder, ISVD or Nanobody, respectively, that binds to CTLA4.

The improved CTLA4 binders provided by the invention are also referred to herein as the "CTLA4 binders of the invention" or "CTLA4 binders". These terms encompass any molecule comprising a molecule that is set forth herein which binds to CTLA4. For example, the terms include an ISVD that comprises an amino acid sequence set forth in a member selected from the group consisting of SEQ ID NOs: 8-43 and 60 as well as any polypeptide, Nanobody, ISVD, fusion protein, conventional antibody or antigen-binding fragment thereof that includes an amino acid sequence set forth in a member selected from the group consisting of SEQ ID NOs: 8-43 and 60; or any bispecific molecule (e.g., an ISVD) that comprises an amino acid sequence set forth in a member selected from the group consisting of SEQ ID NOs: 8-43 and 60, binds to CTLA4 and also binds to another antigen or another epitope such as CD27, LAG3, PD1, or BTLA. A CTLA4 binder of the present invention is F023700912 or F023700914.

The scope of the present invention includes any CTLA4 binder comprising the arrangement of binding moieties set forth in FIG. 11, optionally lacking the FLAG3 and/or HIS6 tags; as well as any of the amino acid sequences set forth in FIG. 12.

WO 2008/071447 describes Nanobodies that can bind to CTLA4 and uses thereof. SEQ ID NO: 1306 of WO 2008/071447 disclosed a CTLA4 specific Nanobody called 11F01, the sequence of which is given herein as SEQ ID NO: 1. This sequence (also referred to herein as "Reference A") and its CDRs are also given in Table A-1 below.

As further described herein, the CTLA4 binders of the invention which are, in an embodiment of the invention in multivalent and/or multispecific CTLA4 binders of the present invention (e.g., F023700914), preferably have the same combination of CDRs (i.e. CDR1, CDR2 and CDR3) as are present in 11F01 or in a binder comprising the sequence of 11F01 (SEQ ID NO: 1). See Table A-1.

The present invention also includes CTLA4 binders which are variants of 11F01 which comprise an amino acid sequence as set forth below in Table A-2 below. The scope of the present invention includes CTLA4 binders that include CDR1, CDR2 and CDR3 of said varaints set forth below in Table A-2.

In addition, the present invention multispecific and/or multivalent binders (e.g., F023700914) comprising a CTLA4 binding moiety that includes CDR1, CDR2 and CDR3 or the amino acid sequence of 11F01 or of one of its varaints set forth below in Table A-2.

TABLE A-1

CTLA4 Nanobody 11F1 (11F01).

| SEQ ID NO | Description | Sequence |
|---|---|---|
| 1 | Reference A WO 2008/071447 SEQ ID NO: 1306 (11F01 or 4CTLA011F01) | EVQLVESGGGLVQAGGSLRLSCAASGGTFSFY GMGWFRQAPGKEQEFVADIRTSAGRTYYADSV KGRFTISRDNAKNTVYLQMNSLKPEDTAVYYC AAEMSGISGWDYWGQGTQVTVSS |

TABLE A-2

Variant CTLA4 Nanobody 11F1.

| 60 | 11F01 (E1D, L11V, A14P, Q45R, A74S, K83R, V89L, M96P, Q108L) (F023700906) | DVQLVESGGGVVQPGGSLRLSCAASGGTFSFYGMG WFRQAPGKEREFVADIRTSAGRTYYADSVKGRFTI SRDNSKNTVYLQMNSLRPEDTALYYCAAEPSGISG WDYWGQGTLVTVSS |
|---|---|---|
| 2 | CDR1 (Kabat) | FYGMG (amino acids 6-10 of SEQ ID NO: 5) |
| 3 | CDR2 (Kabat) | DIRTSAGRTYYADSVKG |
| 4 | CDR3 (Kabat/Abm) | EXSGISGWDY; wherein X is M or P (e.g., EmSGISGWDY (SEQ ID NO: 115) or EpSGISGWDY (SEQ ID NO: 116)) |
| 5 | CDR1 (Abm) | GGTFSFYGMG |
| 6 | CDR2 (Abm) | DIRTSAGRTY (amino acids 1-10 of SEQ ID NO: 3) |
| 7 | CDR3 (Kabat/Abm) | EXSGISGWDY; wherein X is M or P (e.g., EmSGISGWDY (SEQ ID NO: 115) or EpSGISGWDY (SEQ ID NO: 116)) |

Note:
SEQ ID NO: 4 is identical to SEQ ID NO: 7
*CDRs underscored and/or bold

Residue 1 of SEQ ID NO: 60 can be D or E. If residue 1 is D, the CTLA4 binder may be designated as 1D and if residue 1 is E, the CTLA4 binder may be designated as 1E.

In an embodiment of the invention, a CTLA4 binder of the present invention comprises an N73X mutation wherein X is any amino acid other than N, e.g., S, V, G, R, Q, M, H, T, D, E, W, F, K, A, Y or P (or any amino acid other than N).

The present invention includes CTLA4 binders comprising one, two or three of the CDRs of a CTLA4 binder wherein each comprises 0, 1, 2, 3, 4, 5, 6, 7, 8, 9 or 10 amino acid substitutions, e.g., conservative substitutions, and/or comprises 100, 99, 98, 97, 96 or 95% sequence identity relative to the CDRs that are in the CTLA4 binder sequences set forth of Table A-1 or A-2 (e.g., 11F01 (E1D, L11V, A14P, Q45R, A74S, K83R, V89L, M96P, Q108L) or 11F01), or are set forth in SEQ ID NOs: 2-7, wherein a CTLA4 binder having such CDRs retains the ability to bind to CTLA4.

The Kabat residue numbers for certain residues of the CTLA4 binders (e.g., ISVD such as a Nanobody) that are based on Reference A which are set forth herein are shown in the sequence below:

(SEQ ID NO: 1)
$E_1$VQLVESGGGL$_{11}V_{12}Q_{13}A_{14}$GGSLRLSCAAS$G_{26}G_{27}T_{28}F_{29}S_{30}$F

YGMGW$_{36}F_{37}R_{38}Q_{39}$APGKEQ$_{45}E_{46}F_{47}V_{48}A_{49}$DIRTSAGRTYYADS

VKGR$_{66}F_{67}T_{68}I_{69}S_{70}$RDN$_{73}A_{74}$KNTVYLQMN$_{82a}S_{82b}L_{82c}K_{83}$

P$_{84}$EDT$_{87}A_{88}V_{89}Y_{90}Y_{91}$CAAEM$_{96}$SGISGWDYW$_{103}G_{104}Q_{105}$

G$_{106}$TQ$_{108}V_{109}T_{110}V_{111}S_{112}S_{113}$

The Kabat residue numbers for certain residues of the CTLA4 binder 11F01 (E1D, Lily, A14P, Q45R, A74S, K83R, V89L, M96P, Q108L) which are set forth herein are shown in the sequence below:

(SEQ ID NO: 117)
D$_1$VQLVESGGGV$_{11}$VQP$_{14}$GGSLRLSCAASGGTFSFYGMG

WFRQAPGKER$_{45}$EFVADIRTSAGRTYYADSVKGRFTISRDNS$_{74}$KNTVYL

QMNSLR$_{83}$PEDTAL$_{89}$YYCAAEP$_{96}$SGISGWDYWGQGTL$_{108}$VTVSS

The present invention includes any CTLA4 binder comprising the amino acid sequence of SEQ ID NO: 60 or an amino acid sequence comprising 80% or more (e.g., 85%, 90%, 95%, 96%, 97%, 98% or 99%) amino acid sequence identity wherein the CTLA4 binder retains the ability to bind to CTLA4.

The present invention includes embodiments wherein the CDR3 methionine of a CTLA4 binder, at Kabat position 96, is substituted with any amino acid such as Proline (but not with Cys, Asp or Asn), e.g., with any of the following amino acids: Leu, Ile, Val, Ala, Gly, Tyr, Trp, Phe, Glu, Gln, Ser, Thr, His, Arg, Lys or Pro.

Some preferred, but non-limiting CTLA4 binders (e.g., ISVD such as a Nanobody) of the invention are SEQ ID NO: 60 or are listed in FIG. 2 as SEQ ID NOs: 8-43. FIG. 3 shows an alignment of these sequences with Reference A (SEQ ID NO: 1). Of these CTLA4 binders, the binders of SEQ ID NOs:26-43 are examples of CTLA4 binders of the invention having a C-terminal alanine extension, i.e. an alanine residue at the C-terminal end of the ISVD-sequence (also sometimes referred to as "position 114") compared to the usual C-terminal sequence VTVSS (SEQ ID NO: 57, as present in Reference A). As described in WO 2012/175741 (but also for example in WO 2013/024059 and PCT/EP2015/060643 (WO2015/173325)), this C-terminal alanine extension can prevent the binding of so-called "pre-existing antibodies" (assumed to be IgGs) to a putative epitope that is situated at the C-terminal region of the ISV. This epitope is assumed to include, among other residues, the surface-exposed amino acid residues of the C-terminal sequence VTVSS (SEQ ID NO: 57) as well as the amino acid residue at position 14 (and the amino acid residues next/close to the same in the amino acid sequence, such as positions 11, 13 and 15) and may also comprise the amino acid residue at position 83 (and the amino acid residues next/close to the same in the amino acid sequence, such as positions 82, 82a, 82b and 84) and/or the amino acid residue at position 108 (and the amino acid residues next/close to the same in the amino acid sequence, such as position 107).

However, although the presence of such a C-terminal alanine (or a C-terminal extension generally) can greatly reduce (and in a lot of cases even essentially fully prevent) the binding of the "pre-existing antibodies" that can be found in the sera from a range of subjects (both healthy subjects as well as patients), it has been found that the sera from some subjects (such as the sera from patients with some immune diseases such as SLE) can contain pre-existing antibodies that can bind to the C-terminal region of an ISV (when such region is exposed) even when the ISV contains such a C-terminal alanine (or more generally, such C-terminal extension). Reference is again made to the co-pending non-prepublished PCT application PCT/EP2015/060643 (WO2015/173325) by Ablynx N.V. filed on May 13, 2015 and entitled "Improved immunoglobulin variable domains".

Accordingly, one specific objective of the invention is to provide CTLA4 binders (e.g., ISVD such as a Nanobody) that are improved variants of the CTLA4 Nanobody referred to herein as "Reference A" and that have reduced binding by so-called "pre-existing antibodies", and in particular of the kind described in PCT/EP2015/060643 (WO2015/173325) (i.e. those pre-existing antibodies that can bind to an exposed C-terminal region of an ISV even in the presence of a C-terminal extension).

The invention provides CTLA4 binders comprising amino acid sequences that are variants of the sequence of SEQ ID NO: 1 which comprise one or more of the following mutations compared to the sequence of SEQ ID NO: 1:
1D or 1E;
11V;
14P;
45R;
74S;
83R;
89L or 89T;
96P; or
108L;
for example, wherein the CTLA4 binder comprises one or more of the sets of mutations below:
89L in combination with 11V; 14P; 45R; 74S; 83R; 86P; 108L and 1E or 1D;
89L in combination with 11V;
89L in combination with 110K or 110Q;
89L in combination with 112K or 112Q;
89L in combination with 11V; 14P; 45R; 74S; 83R; 86P;108L, 110K or 110Q and 1E or 1D;
89L in combination with 11V; 14P; 45R; 74S; 83R; 86P;108L, 112K or 112Q and 1E or 1D;
89L in combination with 11V and 110K or 110Q;
89L in combination with 11V and 112K or 112Q;
11V in combination with 110K or 110Q; and/or
11V in combination with 112K or 112Q.

In particular, in an embodiment of the invention, CTLA4 binders (e.g., ISVD such as a Nanobody) comprise:
the amino acid at position 1 is preferably E or D;
the amino acid at position 11 is preferably L or V;
the amino acid at position 14 is preferably A or P;
the amino acid at position 45 is preferably Q or R;
the amino acid at position 74 is preferably A or S;
the amino acid at position 83 is preferably K or R;
the amino acid at position 89 is preferably T, V or L;
the amino acid at position 96 is preferably M or P;
the amino acid at position 108 is preferably Q or L;
the amino acid residue at position 110 is preferably suitably chosen from T, K or Q; and
the amino acid residue at position 112 is preferably suitably chosen from S, K or Q; such that, for example, one or more of the following is true:
(i) position 89 is T;
(ii) position 89 is L;
(iii) position 1 is D or E, position 11 is V, position 14 is P, position 45 is R, position 74 is S, position 83 is R, position 89 is L, position 96 is P, and position 108 is L;
(iv) position 89 is L and position 11 is V;
(v) position 89 is L and position 110 is K or Q;
(vi) position 89 is L and position 112 is K or Q;
(vii) position 1 is D or E, position 11 is V, position 14 is P, position 45 is R, position 74 is S, position 83 is R, position 89 is L, position 96 is P, position 108 is L; and position 110 is K or Q;
(viii) position 1 is D or E, position 11 is V, position 14 is P, position 45 is R, position 74 is S, position 83 is R, position 89 is L, position 96 is P, position 108 is L; and position 112 is K or Q;
(ix) position 89 is L and position 11 is V and position 110 is K or Q;

(x) position 89 is L and position 11 is V and position 112 is K or Q;
(xi) position 11 is V and position 110 is K or Q; or
(xii) position 11 is V and position 112 is K or Q.

In particular embodiments, the CTLA4 binders (e.g., an ISVD such as a Nanobody) of the invention comprise amino acid sequences that are variants of SEQ ID NO: 1 in which position 89 is T or in which position 1 is D, position 11 is V, position 14 is P, position 45 is R, position 74 is S, position 83 is R, position 89 is L, position 96 is P and position 108 is L or in which position 11 is V and position 89 is L (optionally in suitable combination with a 110K or 110Q mutation and/or a 112K or 112Q mutation, and in particular in combination with a 110K or 110Q mutation) are particularly preferred. Even more preferred are amino acid sequences in which position 11 is V and position 89 is L, optionally with a 110K or 110Q mutation.

As mentioned, the CTLA4 binders (e.g., ISVD such as a Nanobody) described herein can bind (and in particular, can specifically bind) to CTLA4. In an embodiment of the invention, CTLA4 binders can bind to CTLA4 and thereby prevent CD80, and CD86 on antigen-presenting cells from binding to CTLA-4 on T cells. In an embodiment of the invention, the resulting blockade of CTLA-4 signaling prolongs T-cell activation, restores T-cell proliferation, and thus amplifies T-cell-mediated immunity, which theoretically enhances the patient's capacity to mount an antitumor immune response.

In an embodiment of the invention, a CTLA4 binder of the present invention, has one or more of the following properties:

Binds to CTLA4 (e.g., human and/or cynomolgous monkey CTLA4 (CTLA4-Fc fusion protein), e.g., with a $K_D$ of about 1 nM (e.g., 1.2 nM);
Binds to CTLA4 on the surface of a cell, e.g., a CHO cell expressing CTLA4;
Blocks binding of CD80 or CD86 to CTLA4 (e.g., CTLA4 expressed on CHO cells);
Does not bind to BTLA, CD8, PD1, LAG3, and/or CD28;
Binds in vitro and/or in vivo to human, rhesus monkey and mouse serum albumin (when fused to one or more ALB11002 binders);
Inhibits tumor growth (e.g., of pancreatic tumors, e.g., human pancreatic tumors in a mouse harboring human immune cells)

Table B lists some non-limiting possible combinations of the amino acid residues that can be present at positions 11, 89, 110 and 112 (of SEQ ID NO: 1) in the CTLA4 binders (e.g., ISVD such as a Nanobody) of the invention.

TABLE B

Possible Combinations of Mutations at Amino Acid Positions 11, 89, 110 and 112 in CTLA4 Binder Variants of SEQ ID NO: 1.

| | POSITION | | | | | | POSITION | | | |
|---|---|---|---|---|---|---|---|---|---|---|
| | 11 | 89 | 110 | 112 | | | 11 | 89 | 110 | 112 |
| COMBI-NATION | L | T | T | S | COMBI-NATION | | V | T | T | S |
| | L | T | T | K | | | V | T | T | K |
| | L | T | T | Q | | | V | T | T | Q |
| | L | T | K | S | | | V | T | K | S |
| | L | T | Q | S | | | V | T | Q | S |
| | L | V | T | K | | | V | V | T | K |
| | L | V | T | Q | | | V | V | T | Q |
| | L | V | K | S | | | V | V | K | S |
| | L | V | Q | S | | | V | V | Q | S |
| | | | | | | | V | L | T | S |

TABLE B-continued

Possible Combinations of Mutations at Amino Acid Positions 11, 89, 110 and 112 in CTLA4 Binder Variants of SEQ ID NO: 1.

| POSITION | | | | POSITION | | | |
|---|---|---|---|---|---|---|---|
| 11 | 89 | 110 | 112 | 11 | 89 | 110 | 112 |
| L | L | T | K | V | L | T | K |
| L | L | T | Q | V | L | T | Q |
| L | L | K | S | V | L | K | S |
| L | L | Q | S | V | L | Q | S |

The CTLA4 binders (e.g., ISVD such as a Nanobody) provided by the invention are further as described in the description, examples and figures herein, i.e. they have CDRs that are as described herein and have an overall degree of sequence identity (as defined herein) with the sequence of SEQ ID NO: 1 that is as disclosed herein and/or may have a limited number of "amino acid differences" (as described herein) with (one of) these reference sequences.

The CTLA4 binders (e.g., ISVD such as a Nanobody) of the invention preferably comprise the following CDRs (according to the Kabat convention):

a CDR1 (according to Kabat) that comprises the amino acid sequence FYGMG (SEQ ID NO: 2); and
a CDR2 (according to Kabat) that comprises the amino acid sequence DIRTSAGRTYYADSVKG (SEQ ID NO: 3); and
a CDR3 (according to Kabat) that comprises the amino acid sequence EPSGISGWDY (SEQ ID NO: 116); optionally, wherein CDR1, CDR2 and/or CDR3 comprises 1, 2, 3, 4, 5, 5, 6, 7, 8, 9 or 10 substitutions, e.g., conservative substitutions.

Alternatively, when the CDRs are given according to the Abm convention, the CTLA4 binders (e.g., ISVD such as a Nanobody) of the invention preferably comprise the following CDRs:

a CDR1 (according to Abm) that is the amino acid sequence GGTFSFYGMG (SEQ ID NO: 5); and
a CDR2 (according to Abm) that is the amino acid sequence DIRTSAGRTY (SEQ ID NO: 6); and
a CDR3 (according to Abm) that is the amino acid sequence EPSGISGWDY (SEQ ID NO: 116, which is the same as SEQ ID NO: 4 when X is P); optionally, wherein CDR1, CDR2 and/or CDR3 comprises 1, 2, 3, 4, 5, 5, 6, 7, 8, 9 or 10 substitutions, e.g., conservative substitutions.

A CTLA4 binder (e.g., ISVD such as a Nanobody) of the invention, in an embodiment of the invention, has such CDRs and mutations at positions 1, 11, 14, 45, 74, 83, 89, 96, 108, 110 and/or 112, as discussed herein and, optionally:

a degree of sequence identity with the amino acid sequence of SEQ ID NO: 1 of at least 85%, preferably at least 90%, more preferably at least 95% (in which the CDRs, any C-terminal extension that may be present, as well as the mutations at positions 1, 11, 14, 45, 74, 83, 89, 96, 108, 110 and/or 112 required by the specific aspect involved are not taken into account for determining the degree of sequence identity) when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment); and/or no more than 7, such as no more than 5, preferably no more than 3, such as only 3, 2 or 1 "amino acid differences" with the amino acid sequence of SEQ ID NO: 1 (in which said amino acid differences, if present, may be present in the frameworks and/or the CDRs but are preferably present only in the frameworks and not in the CDRs; not taking into account any C-terminal extension that may be present and not taking into account the mutations at positions 1, 11, 14, 45, 74, 83, 89, 96, 108, 110 and/or 112 required by the specific aspect involved).

The following references relate to BLAST algorithms often used for sequence analysis: BLAST ALGORITHMS: Altschul et al. (2005) FEBS J. 272(20): 5101-5109; Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, New York.

With regards to the various aspects and preferred aspects of the CTLA4 binders (e.g., ISVD such as a Nanobody) of the invention provided by the invention, when it comes to the degree of sequence identity with respect to SEQ ID NO: 1 and/or the number and kind of "amino acid differences" that may be present in such a binder of the invention (i.e. compared to the sequence of SEQ ID NO: 1), it should be noted that, when it is said that:
(i) an amino acid sequence of the invention has a degree of sequence identity with the sequence of SEQ ID NO: 1 of at least 85%, preferably at least 90%, more preferably at least 95% (in which the CDRs, any C-terminal extension that may be present, as well as the mutations at positions 1, 11, 14, 45, 74, 83, 89, 96, 108, 110 and/or 112 required by the specific aspect involved, are not taken into account for determining the degree of sequence identity) when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment);
and/or when it is said that:
(ii) an amino acid sequence of the invention has no more than 7, preferably no more than 5, such as only 3, 2 or 1 "amino acid differences" with the sequence of SEQ ID NO: 1 (again, not taking into account any C-terminal extension that may be present and not taking into account the mutations at positions 1, 11, 14, 45, 74, 83, 89, 96, 108, 110 and/or 112 required by the specific aspect involved),
then this also includes sequences that have no amino acid differences with the sequence of SEQ ID NO: 1 other than the mutations at positions 1, 11, 14, 45, 74, 83, 89, 96, 108, 110 and/or 112 required by the specific aspect involved) and any C-terminal extension that may be present.

Thus, in one specific aspect of the invention, the CTLA4 binders (e.g., ISVD such as a Nanobody) of the invention comprises the amino acid sequence of SEQ ID NO: 1 but wherein at least 1 amino acid mutation at position 1, 11, 14, 45, 74, 83, 89, 96, 108, 110 and/or 112 is substituted (e.g., conservatively substituted) and may have 100% sequence identity with SEQ ID NO: 1 (including the CDRs, but not taking into account the mutation(s) or combination of mutations at positions 1, 11, 14, 45, 74, 83, 89, 96, 108, 110 and/or 112 disclosed herein and/or any C-terminal extension that may be present) and/or may have no amino acid differences with SEQ ID NO: 1 (i.e., other than the mutation(s) or combination of mutations at positions 1, 11, 14, 45, 74, 83, 89, 96, 108, 110 and/or 112 disclosed herein and any C-terminal extension that may be present).

When any amino acid differences are present (i.e. besides any C-terminal extension and the mutations at positions 1, 11, 14, 45, 74, 83, 89, 96, 108, 110 and/or 112 that are required by the specific aspect of the invention involved), these amino acid differences may be present in the CDRs and/or in the framework regions, but they are preferably present only in the framework regions (as defined by the Abm convention, i.e. not in the CDRs as defined according to the Abm convention), i.e. such that the CTLA4 binders (e.g., ISVD such as a Nanobody) of the invention have the same CDRs (defined according to the Abm convention) as are present in SEQ ID NO: 1 or 60.

Also, when a CTLA4 binder (e.g., ISVD such as a Nanobody) of the invention according to any aspect of the invention has one or more amino acid differences with the sequence of SEQ ID NO: 1 (besides the mutations at positions 1, 11, 14, 45, 74, 83, 89, 96, 108, 110 and/or 112 that are required by the specific aspect involved), then some specific, but non-limiting examples of such mutations/amino acid differences that may be present (i.e. compared to the sequences of SEQ ID NO: 1) are for example E1D, P41A, P41L, P41S or P41T (and in particular P41A) and/or T87A (e.g., E1D (optional), Lily, A14P, Q45R, A74S, K83R, V89L, M96P and Q108L). Other examples of mutations are (a suitable combination of) one or more suitable "humanizing" substitutions such as Q108L; reference is for example made to WO 2009/138519 (or in the prior art cited in WO 2009/138519) and WO 2008/020079 (or in the prior art cited in WO 2008/020079), as well as Tables A-3 to A-8 from WO 2008/020079 (which are lists showing possible humanizing substitutions). Preferably, the CTLA4 binders of the invention contain at least a Q108L humanizing substitution.

Also, when the CTLA4 binders (e.g., ISVD such as a Nanobody) of the invention are present at and/or form the N-terminal part of the CTLA4 binder in which they are present, then they preferably contain a D at position 1 (i.e. an E1D mutation compared to Reference A). Some preferred but non-limiting examples of such N-terminal CTLA4 binders are given as SEQ ID NOs: 24 and 25 and 60. Accordingly, in a further aspect, the invention relates to a polypeptide of the invention (which is as further described herein) that has a CTLA4 binder of the invention (which is as further described herein) at its N-terminal end, wherein said CTLA4 binder of the invention has a D at position 1, and is preferably chosen from the CTLA4 binders of SEQ ID NOs: 24 and 25 and 60.

Similarly, when a CTLA4 binder (e.g., ISVD such as a Nanobody) of the invention is used in monovalent format, it preferably has both a C-terminal extension X(n) as described herein and a D at position 1. Some preferred but non-limiting examples of such monovalent CTLA4 binders are given as SEQ ID NOs: 42 and 43. Accordingly, in a further aspect, the invention relates to a monovalent CTLA4 binder of the invention (which is as further described herein) that has a D at position 1 and a C-terminal extension X(n) (which is preferably a single Ala residue). In one specific aspect, said monovalent CTLA4 binder is chosen from SEQ ID NOs: 42 or 43.

By means of preferred, but non-limiting, examples, SEQ ID NOs: 22-25 and 40-42 and 60 are examples of CTLA4 binders (e.g., ISVD such as a Nanobody) of the invention having further amino acid differences with SEQ ID NO: 1, i.e. A14P, Q45R, A74S, K83R and/or Q108L (in addition, as indicated in the previous paragraphs, SEQ ID NOs: 24, 25, 42 and 43 also have a E1D mutation). Thus, in a specific aspect, the invention relates to CTLA4 binders of the invention (i.e. having mutations at positions 11, 89, 110 and/or 112 as described herein and also further being as described herein) that at least have a suitable combination of an optional E1D mutation, A14P mutation, a Q45R mutation, an A74S mutation, a K83R mutation and a Q108L mutation, and preferably a suitable combination of Q108L with any one of the other A14P, Q45R, A74S and K83R mutations, and preferably in combination with any two of these other mutations, more preferably with any three of these mutations (such as with the combination A14P, A74S and K83R or E1D, L11V, A14P, Q45R, A74S, K83R, V89L, M96P and Q108L), such as with all of these mutations (and again, when the CTLA4 binder is monovalent or present at the N-terminal end of a CTLA4 binder of the invention, preferably also an E1D mutation).

The CTLA4 binders (e.g., ISVD such as a Nanobody) of the invention, when they are used in a monovalent format and/or when a CTLA4 binding moiety is present at and/or forms the C-terminal end of the CTLA4 binder (or when they otherwise have an "exposed" C-terminal end in such a polypeptide, by which is generally meant that the C-terminal end of the ISVD is not associated with or linked to a constant domain (such as a CH1 domain); reference is again made to WO 2012/175741 and PCT/EP2015/060643 (WO 2015/173325)), preferably also have a C-terminal extension of the formula $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen from naturally occurring amino acid residues (although according to preferred one aspect, it does not comprise any cysteine residues), and preferably independently chosen from the group consisting of alanine (A), glycine (G), valine (V), leucine (L) or isoleucine (I).

According to some preferred, but non-limiting examples of such C-terminal extensions $X_{(n)}$, and n can be as follows:

(a) n=1 and X=Ala;
(b) n=2 and each X=Ala;
(c) n=3 and each X=Ala;
(d) n=2 and at least one X=Ala (with the remaining amino acid residue(s) X being independently chosen from any naturally occurring amino acid but preferably being independently chosen from Val, Leu and/or Ile);
(e) n=3 and at least one X=Ala (with the remaining amino acid residue(s) X being independently chosen from any naturally occurring amino acid but preferably being independently chosen from Val, Leu and/or Ile);
(f) n=3 and at least two X=Ala (with the remaining amino acid residue(s) X being independently chosen from any naturally occurring amino acid but preferably being independently chosen from Val, Leu and/or Ile);
(g) n=1 and X=Gly;
(h) n=2 and each X=Gly;
(i) n=3 and each X=Gly;
(j) n=2 and at least one X=Gly (with the remaining amino acid residue(s) X being independently chosen from any naturally occurring amino acid but preferably being independently chosen from Val, Leu and/or Ile);
(k) n=3 and at least one X=Gly (with the remaining amino acid residue(s) X being independently chosen from any naturally occurring amino acid but preferably being independently chosen from Val, Leu and/or Ile);
(l) n=3 and at least two X=Gly (with the remaining amino acid residue(s) X being independently chosen from any naturally occurring amino acid but preferably being independently chosen from Val, Leu and/or Ile);
(m) n=2 and each X=Ala or Gly;
(n) n=3 and each X=Ala or Gly;
(o) n=3 and at least one X=Ala or Gly (with the remaining amino acid residue(s) X being independently chosen from any naturally occurring amino acid but preferably being independently chosen from Val, Leu and/or Ile); or
(p) n=3 and at least two X=Ala or Gly (with the remaining amino acid residue(s) X being independently chosen from any naturally occurring amino acid but preferably being independently chosen from Val, Leu and/or Ile);

with aspects (a), (b), (c), (g), (h), (i), (m) and (n) being particularly preferred, with aspects in which n=1 or 2 being preferred and aspects in which n=1 being particularly preferred.

It should also be noted that, preferably, any C-terminal extension present in a CTLA4 binder (e.g., ISVD such as a Nanobody) of the invention does not contain a (free) cysteine residue unless said cysteine residue is used or intended for further functionalization, for example for PEGylation.

Some specific, but non-limiting examples of useful C-terminal extensions are the following amino acid sequences: A, AA, AAA, G, GG, GGG, AG, GA, AAG, AGG, AGA, GGA, GAA or GAG.

When the CTLA4 binders (e.g., ISVD such as a Nanobody) of the invention contain mutations at positions 110 or 112 (optionally in combination with mutations at position 1, 11, 14, 45, 74, 83, 89, 96 and/or 108 as described herein) (relative to the amino acid sequence of SEQ ID NO: 1), the C-terminal amino acid residues of framework 4 (starting from position 109) can, in an embodiment of the invention, be as set forth in SEQ ID NO: 1 but wherein the 5 C-terminal residues can be substituted as follows:

(i) if no C-terminal extension is present: VTVKS (SEQ ID NO: 45), VTVQS (SEQ ID NO: 46), VKVSS (SEQ ID NO: 47) or VQVSS (SEQ ID NO: 48); or
(ii) if a C-terminal extension is present: VTVKSX$_{(n)}$ (SEQ ID NO: 49), VTVQSX(n) (SEQ ID NO: 50), VKVSSX(n) (SEQ ID NO: 51) or VQVSSX$_{(n)}$ (SEQ ID NO: 52), such as VTVKSA (SEQ ID NO: 53), VTVQSA (SEQ ID NO: 54), VKVSSA (SEQ ID NO: 55) or VQVSSA (SEQ ID NO: 56).

When the CTLA4 binders (e.g., ISVD such as a Nanobody) of the invention do not contain mutations at positions 110 or 112 (but only mutations at position 1, 11, 14, 45, 74, 83, 89, 96 and/or 108 as described herein), the C-terminal amino acid residues of framework 4 (starting from position 109) can, in an embodiment of the invention, be as set forth in SEQ ID NO: 1 but wherein the 5 C-terminal residues can be substituted as follows:
 (i) when no C-terminal extension is present: VTVSS (SEQ ID NO: 57) (as in the sequence of SEQ ID NO: 1); or
 (ii) when a C-terminal extension is present: VTVSSX$_{(n)}$ (SEQ ID NO: 58) such as VTVSSA (SEQ ID NO: 59). In these C-terminal sequences, X and n are as defined herein for the C-terminal extensions.

Some preferred but non-limiting examples of CTLA4 binders (e.g., ISVD such as a Nanobody) of the invention are given in SEQ ID NOs: 9-43 and 60, and each of these sequences forms a further aspect of the invention (as do proteins, CTLA4 binders, polypeptides or other compounds or constructs that comprise one of these sequences). Of these, the CTLA4 binders of SEQ ID NOs: 9-25 and 60 do not have a C-terminal extension, and the CTLA4 binders of SEQ ID NOs: 26-43 contain a C-terminal alanine (which is a preferred but non-limiting example of a C-terminal extension as described herein).

Examples of CTLA4 binders (e.g., ISVD such as a Nanobody) of the invention comprise the amino acid sequences of SEQ ID NOs: 22, 23, 24, 25, 40, 41, 42, 43 and 60.

Thus, in a first aspect, the invention relates to a CTLA4 binder (e.g., an immunoglobulin single variable domain such as a Nanobody) having:
  a CDR1 (according to Kabat) that is the amino acid sequence FYGMG (SEQ ID NO: 2); and
  a CDR2 (according to Kabat) that is the amino acid sequence DIRTSAGRTYYADSVKG (SEQ ID NO: 3); and
  a CDR3 (according to Kabat) that is the amino acid sequence EPSGISGWDY (SEQ ID NO: 116);
and having:
  a degree of sequence identity with the amino acid sequence of SEQ ID NO: 1 of at least 85%, preferably at least 90%, more preferably at least 95% (in which the CDRs, any C-terminal extension that may be present, as well as the mutations at positions 1, 11, 14, 45, 74, 83, 89, 96, 108, 110 and/or 112 required by the specific aspect involved are not taken into account for determining the degree of sequence identity) when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment); and/or;
and/or
  no more than 7, such as no more than 5, preferably no more than 3, such as only 3, 2 or 1 "amino acid differences" (as defined herein, and not taking into account any of the above-listed mutations at position(s) 1, 11, 14, 45, 74, 83, 89, 96, 108, 110 and/or 112 that may be present and not taking into account any C-terminal extension that may be present) with the amino acid sequence of SEQ ID NO: 1 (in which said amino acid differences, if present, may be present in the frameworks and/or the CDRs but are preferably present only in the frameworks and not in the CDRs);
and optionally having:
  a C-terminal extension (X)$_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);
wherein, in the amino acid sequence of the CTLA4 binder:
  the amino acid residue at position 1 is preferably chosen from E or D;
  the amino acid residue at position 11 is preferably chosen from L or V;
  the amino acid residue at position 14 is preferably chosen from A or P;
  the amino acid residue at position 45 is preferably chosen from Q or R;
  the amino acid residue at position 74 is preferably chosen from A or S;
  the amino acid residue at position 83 is preferably chosen from K or R;
  the amino acid residue at position 89 is preferably suitably chosen from T, V or L;
  the amino acid residue at position 96 is preferably chosen from M or P;
  the amino acid residue at position 108 is preferably chosen from Q or L;
  the amino acid residue at position 110 is preferably suitably chosen from T, K or Q; and/or
  the amino acid residue at position 112 is preferably suitably chosen from S, K or Q;
such that, for example, one or more of the following is true:
  (i) position 1 is E or D;
  (ii) position 11 is V;
  (iii) position 14 is P;
  (iv) position 45 is R;
  (v) position 74 is S;
  (vi) position 83 is R;
  (vii) position 89 is T or L;
  (viii) position 96 is P;
  (ix) position 108 is L; and/or
  for example, wherein the CTLA4 binder comprises one or more of the sets of mutations below
  a. position 11 is V and position 110 is K or Q;
  b. position 11 is V and position 112 is K or Q.
  c. position 89 is L and position 11 is V;
  d. position 89 is L and position 110 is K or Q;
  e. position 89 is L and position 112 is K or Q;
  f. position 89 is L and position 11 is V and position 110 is K or Q;
  g. position 89 is L and position 11 is V and position 112 is K or Q;
  h. position 1 is E or D; position 11 is V; position 14 is P; position 45 is R; position 74 is S; position 83 is R; position 89 is L; position 96 is P; and position 108 is L;
  i. position 1 is E or D; position 11 is V; position 14 is P; position 45 is R; position 74 is S; position 83 is R; position 89 is L; position 96 is P; position 108 is L; and position 110 is K or Q;

j. position 1 is E or D; position 11 is V; position 14 is P; position 45 is R; position 74 is S; position 83 is R; position 89 is L; position 96 is P; position 108 is L; and position 112 is K or Q;

k. position 1 is E or D; position 11 is V; position 14 is P; position 45 is R; position 74 is S; position 83 is R; position 89 is L; position 96 is P; and position 108 is L.

In a further aspect, the invention relates to a CTLA4 binder (e.g., an immunoglobulin single variable domain such as a Nanobody) having:

- a CDR1 (according to Kabat) that is the amino acid sequence FYGMG (SEQ ID NO: 2); and
- a CDR2 (according to Kabat) that is the amino acid sequence DIRTSAGRTYYADSVKG (SEQ ID NO: 3); and
- a CDR3 (according to Kabat) that is the amino acid sequence EPSGISGWDY (SEQ ID NO: 116.

and having:

- a degree of sequence identity with the amino acid sequence of SEQ ID NO: 1 of at least 85%, preferably at least 90%, more preferably at least 95% (in which the CDRs, any C-terminal extension that may be present, as well as the mutations at positions 1, 11, 14, 45, 74, 83, 89, 96, 108, 110 and/or 112 required by the specific aspect involved are not taken into account for determining the degree of sequence identity) when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment);

and/or no more than 7, such as no more than 5, preferably no more than 3, such as only 3, 2 or 1 "amino acid differences" (as defined herein, and not taking into account any of the above-listed mutations at position(s) 1, 11, 14, 45, 74, 83, 89, 96, 108, 110 and/or 112 that may be present and not taking into account any C-terminal extension that may be present) with the amino acid sequence of SEQ ID NO: 1 (in which said amino acid differences, if present, may be present in the frameworks and/or the CDRs but are preferably present only in the frameworks and not in the CDRs);

and optionally having:

- a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

which CTLA4 binder (e.g., an immunoglobulin single variable domain such as a Nanobody) comprises one or more of the following amino acid residues (i.e. mutations compared to the amino acid sequence of SEQ ID NO: 1) at the positions mentioned (numbering according to Kabat):

1D or 1E;
11V;
14P;
45R;
74S;
83R;
89T or 89L;
96P; or
108L;

for example, wherein the CTLA4 binder comprises one or more of the sets of mutations below:

1D or 1E in combination with 11V; 14P; 45R; 74S; 83R; 89L; 96P; and 108L;
11V in combination with 110K or 110Q;
11V in combination with 112K or 112Q;
89L in combination with 11V;
89L in combination with 110K or 110Q;
89L in combination with 112K or 112Q;
1D or 1E in combination with 11V; 14P; 45R; 74S; 83R; 89L; 96P; 108L and 110K or 110Q;
1D or 1E in combination with 11V; 14P; 45R; 74S; 83R; 89L; 96P; 108L and 112K or 112Q;
89L in combination with 11V and 110K or 110Q; or
89L in combination with 11V and 112K or 112Q;

As mentioned, when a CTLA4 binder (e.g., ISVD such as a Nanobody) of the invention is used in a monovalent format and/or wherein the CTLA4 binding moiety is present at the C-terminal end of a CTLA4 binder of the invention (as defined herein), the CTLA4 binder preferably has a C-terminal extension X(n), which C-terminal extension may be as described herein for the CTLA4 binders of the invention and/or as described in WO 2012/175741 or PCT/EP2015/060643 (WO2015/173325).

Some preferred, but non-limiting examples of CTLA4 binders (e.g., ISVD such as a Nanobody) of the invention are given in SEQ ID NOs: 8-43 or 60, and each of these amino acid sequences individually forms a further aspect of the invention.

As mentioned, in the invention, amino acid sequences in which position 89 is T; or in which position 1 is E or D, position 11 is V, position 14 is P, position 45 is R, position 74 is S, position 83 is R, position 89 is L, position 96 is P and position 108 is L; or in which position 11 is V and position 89 is L (optionally in suitable combination with a 110K or 110Q mutation and/or a 112K or 112Q mutation, and in particular in combination with a 110K or 110Q mutation) are particularly preferred. Even more preferred are amino acid sequences in which position 11 is V and position 89 is L, optionally with a 110K or 110Q mutation.

Thus, in one preferred aspect, the invention relates to a CTLA4 binder (e.g., an immunoglobulin single variable domain such as a Nanobody) having:

- a CDR1 (according to Kabat) that is the amino acid sequence FYGMG (SEQ ID NO: 2); and
- a CDR2 (according to Kabat) that is the amino acid sequence DIRTSAGRTYYADSVKG (SEQ ID NO: 3); and
- a CDR3 (according to Kabat) that is the amino acid sequence EPSGISGWDY (SEQ ID NO: 116;

and having:

- a degree of sequence identity with the amino acid sequence of SEQ ID NO: 1 of at least 85%, preferably at least 90%, more preferably at least 95% (in which the CDRs, any C-terminal extension that may be present, as well as the mutations at positions 1, 11, 14, 45, 74, 83, 89, 96, 108, 110 and/or 112 required by the specific aspect involved are not taken into account for determining the degree of sequence identity), when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment); and/or; and/or no more than 7, such as no more than 5, preferably no more than 3, such as only 3, 2 or 1 "amino acid differences" (as defined herein, and not taking into account any of the above-listed mutations at position(s) 1, 11, 14, 45, 74, 83, 89, 96, 108, 110 and/or 112 that may be present and not taking into account any C-terminal extension that may be present) with the amino acid sequence of SEQ ID NO: 1 (in which said amino acid differences, if present, may be present in the frameworks and/or the CDRs but are preferably present only in the frameworks and not in the CDRs);

and optionally having:

a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

wherein, in the amino acid sequence of the CTLA4 binder:

the amino acid residue at position 1 is preferably chosen from E or D;

the amino acid residue at position 11 is preferably chosen from L or V;

the amino acid residue at position 14 is preferably chosen from A or P;

the amino acid residue at position 45 is preferably chosen from Q or R;

the amino acid residue at position 74 is preferably chosen from A or S;

the amino acid residue at position 83 is preferably chosen from K or R;

the amino acid residue at position 89 is preferably chosen from T, L or V;

the amino acid residue at position 96 is preferably chosen from M or P;

the amino acid residue at position 108 is preferably chosen from L or Q;

the amino acid residue at position 110 is preferably suitably chosen from T, K or Q (and is preferably T); and/or the amino acid residue at position 112 is preferably suitably chosen from S, K or Q (and is preferably S).

In another preferred aspect, the invention relates to a CTLA4 binder (e.g., an immunoglobulin single variable domain such as a Nanobody) having:

a CDR1 (according to Kabat) that is the amino acid sequence FYGMG (SEQ ID NO: 2); and a CDR2 (according to Kabat) that is the amino acid sequence DIRTSAGRTYYADSVKG (SEQ ID NO: 3); and a CDR3 (according to Kabat) that is the amino acid sequence EPSGISGWDY (SEQ ID NO: 116;

and having:

a degree of sequence identity with the amino acid sequence of SEQ ID NO: 1 of at least 85%, preferably at least 90%, more preferably at least 95% (in which the CDRs, any C-terminal extension that may be present, as well as the mutations at positions 1, 11, 14, 45, 74, 83, 89, 96, 108, 110 and/or 112 required by the specific aspect involved are not taken into account for determining the degree of sequence identity) when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment);

and/or no more than 7, such as no more than 5, preferably no more than 3, such as only 3, 2 or 1 "amino acid differences" (as defined herein, and not taking into account any of the above-listed mutations at position(s) 1, 11, 14, 45, 74, 83, 89, 96, 108, 110 and/or 112 that may be present and not taking into account any C-terminal extension that may be present) with the amino acid sequence of SEQ ID NO: 1 (in which said amino acid differences, if present, may be present in the frameworks and/or the CDRs but are preferably present only in the frameworks and not in the CDRs);

and optionally having:

a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

in which, for example, the CTLA4 binder comprises one or more mutations according to the following:

the amino acid residue at position 1 is E or D;
the amino acid residue at position 11 is V;
the amino acid residue at position 14 is P;
the amino acid residue at position 45 is R;
the amino acid residue at position 74 is S;
the amino acid residue at position 83 is R;
the amino acid residue at position 89 is L;
the amino acid residue at position 96 is P;
the amino acid residue at position 108 is L;
the amino acid residue at position 110 is preferably chosen from T, K or Q; or
the amino acid residue at position 112 is preferably chosen from S, K or Q.

In one specific, but non-limiting aspect, the CTLA4 binders (e.g., ISVD such as a Nanobody) of the invention comprise the one or more of following sets of mutations (i.e. mutations compared to the sequence of SEQ ID NO: 1) at the positions mentioned (numbering according to Kabat):

11V in combination with 89L;
11V in combination with 110K or 110Q;
11V in combination with 112K or 112Q;
11V in combination with 89L and 110K or 110Q;
11V in combination with 89L and 112K or 112Q;
11V in combination with 1D or 1E, 14P, 45R, 74S, 83R, 89L, 96P, 108L and 110K or 110Q;
11V in combination with 1D or 1E, 14P, 45R, 74S, 83R, 89L, 96P, 108L and 112K or 112Q; or
11V in combination with 1D or 1E, 14P, 45R, 74S, 83R, 89L, 96P and 108L. and have CDRs which are in a CTLA4 binder of Table A, e.g., in SEQ ID NO: 1 or SEQ ID NO: 60 (e.g., according to Kabat) and have an overall degree of sequence identity with the amino acid sequence of SEQ ID NO: 1 that are as described herein.

In another specific, but non-limiting aspect, the CTLA4 binders (e.g., ISVD such as a Nanobody) of the invention comprise one or more of the following sets of mutations (i.e. mutations compared to the sequence of SEQ ID NO: 1) at the positions mentioned (numbering according to Kabat):

89L in combination with 11V;
89L in combination with 110K or 110Q;
89L in combination with 112K or 112Q;
89L in combination with 11V and 110K or 110Q;
89L in combination with 11V and 112K or 112Q;
89L in combination with 1D or 1E, 11V, 14P, 45R, 74S, 83R, 96P and 108L;
89L in combination with 1D or 1E, 11V, 14P, 45R, 74S, 83R, 96P, 108L and 110K or 110Q; or
89L in combination with 1D or 1E, 11V, 14P, 45R, 74S, 83R, 96P, 108L and 112K or 112Q, and have CDRs which are in a CTLA4 binder of Table A, e.g., in SEQ ID NO: 1 or SEQ ID NO: 60 (e.g., according to Kabat) and have an overall degree of sequence identity with the amino acid sequence of SEQ ID NO: 1 that are as described herein.

In another specific, but non-limiting aspect, the CTLA4 binders (e.g., ISVD such as a Nanobody) of the invention comprise one or more of the following amino acid sets of mutations (i.e. mutations compared to the sequence of SEQ ID NO: 1) at the positions mentioned (numbering according to Kabat):

110K or 110Q in combination with 11V;
110K or 110Q in combination with 89L;
110K or 110Q in combination with 11V and 89L;
110K or 110Q in combination with 1D or 1E, 11V, 14P, 45R, 74S, 83R, 89L, 96P and 108L.

and have CDRs which are in a CTLA4 binder of Table A, e.g., in SEQ ID NO: 1 or SEQ ID NO: 60 (e.g., according to Kabat) and have an overall degree of sequence identity with the amino acid sequence of SEQ ID NO: 1 that are as described herein.

In another specific, but non-limiting aspect, the CTLA4 binders (e.g., ISVD such as a Nanobody) of the invention comprise one or more of the following sets of mutations (i.e. mutations compared to the sequence of SEQ ID NO: 1) at the positions mentioned (numbering according to Kabat):

112K or 112Q in combination with 11V;
112K or 112Q in combination with 89L; or
112K or 112Q in combination with 11V and 89L; or
112K or 112Q in combination with 1D or 1E, 11V, 14P, 45R, 74S, 83R, 89L, 96P and 108L.

and have CDRs which are in a CTLA4 binder of Table A, e.g., in SEQ ID NO: 1 or SEQ ID NO: 60 (e.g., according to Kabat) and have an overall degree of sequence identity with the amino acid sequence of SEQ ID NO: 1 that are as described herein.

In another aspect, the CTLA4 binders (e.g., ISVD such as a Nanobody) of the invention comprise a T at position 89 and have CDRs such as those set forth in SEQ ID NO: 60 (e.g., according to Kabat) and have an overall degree of sequence identity with the amino acid sequence of SEQ ID NO: 1 that are as described herein.

In another aspect, the CTLA4 binders (e.g., ISVD such as a Nanobody) of the invention comprise a V at position 11 and an L at position 89 and have CDRs such as those set forth in SEQ ID NO: 1 or 60 (e.g., according to Kabat) and have an overall degree of sequence identity with the amino acid sequence of SEQ ID NO: 1 that are as described herein.

As mentioned, the CTLA4 binders (e.g., ISVD such as a Nanobody) of the invention according to the above aspects preferably further contain a suitable combination of an E1D mutation, L11V mutation, A14P mutation, a Q45R mutation, an A74S mutation, a K83R mutation, a V89L mutation, an M96P mutation and a Q108L mutation, and, in an embodiment of the invention, a suitable combination of Q108L with any one of the other A14P, Q45R, A74S and K83R mutations, and, in an embodiment of the invention, in combination with any two of these other mutations, more preferably with any three of these mutations (such as with the combination A14P, A74S and K83R), such as with all four of these mutations (and again, when the CTLA4 binder is monovalent or present at the N-terminal end of a CTLA4 binder of the invention, preferably also an E1D mutation).

In another aspect, the invention relates to a CTLA4 binder (e.g., an immunoglobulin single variable domain such as a Nanobody) having:

a CDR1 (according to Abm) that is the amino acid sequence GGTFSFYGMG (SEQ ID NO: 5); and
a CDR2 (according to Abm) that is the amino acid sequence DIRTSAGRTY (SEQ ID NO: 6); and
a CDR3 (according to Abm) that is the amino acid sequence EPSGISGWDY (SEQ ID NO: 116;

and having:
a degree of sequence identity with the amino acid sequence of SEQ ID NO: 1 of at least 85%, preferably at least 90%, more preferably at least 95% (in which the CDRs, any C-terminal extension that may be present, as well as the mutations at positions 1, 11, 14, 45, 74, 83, 89, 96, 108, 110 and/or 112 required by the specific aspect involved are not taken into account for determining the degree of sequence identity) when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment);

and/or
no more than 7, such as no more than 5, preferably no more than 3, such as only 3, 2 or 1 "amino acid differences" (as defined herein, and not taking into account any of the above-listed mutations at position(s) 1, 11, 14, 45, 74, 83, 89, 96, 108, 110 and/or 112 that may be present and not taking into account any C-terminal extension that may be present) with the amino acid sequence of SEQ ID NO: 1 (in which said amino acid differences, if present, may be present in the frameworks and/or the CDRs but are preferably present only in the frameworks and not in the CDRs);

and optionally having:
a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

comprising an amino acid sequence wherein:
the amino acid residue at position 1 is E or D;
the amino acid residue at position 11 is L or V;
the amino acid residue at position 14 is P;
the amino acid residue at position 45 is R;
the amino acid residue at position 74 is S;
the amino acid residue at position 83 is R;
the amino acid residue at position 89 is preferably chosen from T, V or L;
the amino acid residue at position 96 is P;
the amino acid residue at position 108 is L;
the amino acid residue at position 110 is preferably chosen from T, K or Q; and the amino acid residue at position 112 is preferably chosen from S, K or Q;

for example, such that one or more of the following is true:
(i) position 1 is D or E;
(ii) position 11 is V;
(iii) position 14 is P;
(iv) position 45 is R;
(v) position 74 is S;
(vi) position 83 is R;
(vii) position 89 is L or T;
(viii) position 96 is P; or
(ix) position 108 is L.

for example, wherein the CTLA4 binder comprises one or more of the sets of mutations below:
a. position 11 is V and position 110 is K or Q;
b. position 11 is V and position 112 is K or Q;
c. position 89 is L and position 11 is V;
d. position 89 is L and position 110 is K or Q;
e. position 89 is L and position 112 is K or Q;
f. position 89 is L and position 11 is V and position 110 is K or Q; or
g. position 89 is L and position 11 is V and position 112 is K or Q.

In a further aspect, the invention relates to an CTLA4 binder (e.g., an immunoglobulin single variable domain such as a Nanobody) having:
a CDR1 (according to Abm) that is the amino acid sequence GGTFSFYGMG (SEQ ID NO: 5); and
a CDR2 (according to Abm) that is the amino acid sequence DIRTSAGRTY (SEQ ID NO: 6); and
a CDR3 (according to Abm) that is the amino acid sequence EPSGISGWDY (SEQ ID NO: 116;
and having:
a degree of sequence identity with the amino acid sequence of SEQ ID NO: 1 of at least 85%, preferably at least 90%, more preferably at least 95% (in which the CDRs, any C-terminal extension that may be present, as well as the mutations at positions 1, 11, 14, 45, 74, 83, 89, 96, 108, 110 and/or 112 required by the specific aspect involved are not taken into account for determining the degree of sequence identity) when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment);
and/or
no more than 7, such as no more than 5, preferably no more than 3, such as only 3, 2 or 1 "amino acid differences" (as defined herein, and not taking into account any of the above-listed mutations at position(s) 1, 11, 14, 45, 74, 83, 89, 96, 108, 110 and/or 112 that may be present and not taking into account any C-terminal extension that may be present) with the amino acid sequence of SEQ ID NO: 1 (in which said amino acid differences, if present, may be present in the frameworks and/or the CDRs but are preferably present only in the frameworks and not in the CDRs);
and optionally having:
a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I); which CTLA4 binder (e.g., an immunoglobulin single variable domain such as a Nanobody) comprises one or more of the following amino acid residues (i.e. mutations compared to the amino acid sequence of SEQ ID NO: 1) at the positions mentioned (numbering according to Kabat):
1D or 1E;
11V;
14P;
45R;
74S;
83R;
89L or 89T;
96P; or
108L;

for example, wherein the CTLA4 binder comprises one or more of the sets of mutations below:
11V in combination with 110K or 110Q;
11V in combination with 112K or 112Q;
89L in combination with 11V;
89L in combination with 110K or 110Q;
89L in combination with 112K or 112Q;
89L in combination with 11V and 110K or 110Q; or
89L in combination with 11V and 112K or 112Q.

As mentioned, when a CTLA4 binder (e.g., ISVD such as a Nanobody) of the invention is used in a monovalent format and/or wherein the CTLA4 binding moiety is present at the C-terminal end of a CTLA4 binder of the invention (as defined herein), the CTLA4 binder preferably has a C-terminal extension X(n), which C-terminal extension may be as described herein for the CTLA4 binders of the invention and/or as described in WO 2012/175741 or PCT/EP2015/060643 (WO2015/173325).

Some preferred, but non-limiting examples of CTLA4 binders (e.g., ISVD such as a Nanobody) of the invention are given in SEQ ID NOs: 8-43 and 60, and each of these amino acid sequences individually forms a further aspect of the invention.

As mentioned, in the invention, amino acid sequences in which position 89 is T; or in which position 1 is E or D, position 11 is V, position 14 is P, position 45 is R, position 74 is S, position 83 is R, position 89 is L, position 96 is P, or position 108 is L; or in which position 11 is V and position 89 is L (optionally in suitable combination with a 110K or 110Q mutation and/or a 112K or 112Q mutation, and in particular in combination with a 110K or 110Q mutation) are particularly preferred. Even more preferred are amino acid sequences in which position 11 is V and position 89 is L, optionally with a 110K or 110Q mutation.

Thus, in one preferred aspect, the invention relates to a CTLA4 binder (e.g., an immunoglobulin single variable domain such as a Nanobody) having:
a CDR1 (according to Abm) that is the amino acid sequence GGTFSFYGMG (SEQ ID NO: 5); and
a CDR2 (according to Abm) that is the amino acid sequence DIRTSAGRTY (SEQ ID NO: 6); and
a CDR3 (according to Abm) that is the amino acid sequence EPSGISGWDY (SEQ ID NO: 116;
and having:
a degree of sequence identity with the amino acid sequence of SEQ ID NO: 1 of at least 85%, preferably at least 90%, more preferably at least 95% (in which the CDRs, any C-terminal extension that may be present, as well as the mutations at positions 1, 11, 14, 45, 74, 83, 89, 96, 108, 110 and/or 112 required by the specific aspect involved are not taken into account for determining the degree of sequence identity) when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment);

and/or no more than 7, such as no more than 5, preferably no more than 3, such as only 3, 2 or 1 "amino acid differences" (as defined herein, and not taking into account any of the above-listed mutations at position(s) 1, 11, 14, 45, 74, 83, 89, 96, 108, 110 and/or 112 that may be present and not taking into account any C-terminal extension that may be present) with the amino acid sequence of SEQ ID NO: 1 (in which said amino acid differences, if present, may be present in the frameworks and/or the CDRs but are preferably present only in the frameworks and not in the CDRs);

and optionally having:

a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I); comprising an amino acid sequence having one or mutations (relative to the amino acid sequence of SEQ ID NO: 1) according to the following:

the amino acid residue at position 1 is preferably chosen from E and D;

the amino acid residue at position 11 is preferably chosen from L and V;

the amino acid residue at position 14 is preferably chosen from A and P;

the amino acid residue at position 45 is preferably chosen from Q and R;

the amino acid residue at position 74 is preferably chosen from A and S;

the amino acid residue at position 83 is preferably chosen from K and R;

the amino acid residue at position 89 is preferably chosen from T, L and V;

the amino acid residue at position 96 is preferably chosen from M or P;

the amino acid residue at position 108 is preferably chosen from L or Q;

the amino acid residue at position 110 is preferably chosen from T, K or Q (and is preferably T); and the amino acid residue at position 112 is preferably chosen from S, K or Q (and in preferably S).

In another preferred aspect, the invention relates to a CTLA4 binder (e.g., an immunoglobulin single variable domain such as a Nanobody) having:

a CDR1 (according to Abm) that is the amino acid sequence GGTFSFYGMG (SEQ ID NO: 5); and a CDR2 (according to Abm) that is the amino acid sequence DIRTSAGRTY (SEQ ID NO: 6); and a CDR3 (according to Abm) that is the amino acid sequence EPSGISGWDY (SEQ ID NO: 116;

and having:

a degree of sequence identity with the amino acid sequence of SEQ ID NO: 1 of at least 85%, preferably at least 90%, more preferably at least 95% (in which the CDRs, any C-terminal extension that may be present, as well as the mutations at positions 1, 11, 14, 45, 74, 83, 89, 96, 108, 110 and/or 112 required by the specific aspect involved are not taken into account for determining the degree of sequence identity) when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment);

and/or no more than 7, such as no more than 5, preferably no more than 3, such as only 3, 2 or 1 "amino acid differences" (as defined herein, and not taking into account any of the above-listed mutations at position(s) 1, 11, 14, 45, 74, 83, 89, 96, 108, 110 and/or 112 that may be present and not taking into account any C-terminal extension that may be present) with the amino acid sequence of SEQ ID NO: 1 (in which said amino acid differences, if present, may be present in the frameworks and/or the CDRs but are preferably present only in the frameworks and not in the CDRs);

and optionally having:

a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

in which the CTLA4 binder comprises one or more of the following mutations:

the amino acid residue at position 1 is D or E;

the amino acid residue at position 11 is V;

the amino acid residue at position 14 is P;

the amino acid residue at position 45 is R;

the amino acid residue at position 74 is S;

the amino acid residue at position 83 is R;

the amino acid residue at position 89 is L;

the amino acid residue at position 96 is P;

the amino acid residue at position 108 is L;

the amino acid residue at position 110 is preferably suitably chosen from T, K or Q; or the amino acid residue at position 112 is preferably suitably chosen from S, K or Q.

In one specific, but non-limiting aspect, the CTLA4 binders (e.g., ISVD such as a Nanobody) of the invention comprise the one or more of following sets of mutations (i.e. mutations compared to the sequence of SEQ ID NO: 1) at the positions mentioned (numbering according to Kabat):

11V in combination with 89L;

11V in combination with 1D, 14P, 45R, 74S, 83R, 89L, 96P, 108L;

11V in combination with 1E, 14P, 45R, 74S, 83R, 89L, 96P, 108L;

11V in combination with 110K or 110Q;

11V in combination with 110K or 110Q, and 1D or 1E and 14P, 45R, 74S, 83R, 89L, 96P, and 108L;

11V in combination with 112K or 112Q;

11V in combination with 112K or 112Q, and 1D or 1E and 14P, 45R, 74S, 83R, 89L, 96P, and 108L;

11V in combination with 89L and 110K or 110Q; or 11V in combination with 89L and 112K or 112Q, and have CDRs which are in a CTLA4 binder of Table A, e.g., in SEQ ID NO: 1 or SEQ ID NO: 60 (e.g., according to Abm) and have an overall degree of sequence identity with the amino acid sequence of SEQ ID NO: 1 that are as described herein.

In another specific, but non-limiting aspect, the CTLA4 binders (e.g., ISVD such as a Nanobody) of the invention comprise the following sets of mutations (i.e. mutations compared to the sequence of SEQ ID NO: 1) at the positions mentioned (numbering according to Kabat):
  89L in combination with 11V;
  89L in combination with 1D or 1E, 11V, 14P, 45R, 74S, 83R, 96P and 108L;
  89L in combination with 110K or 110Q;
  89L in combination with 110K or 110Q and 1D or 1E and 11V, 14P, 45R, 74S, 83R, 96P and 108L;
  89L in combination with 112K or 112Q;
  89L in combination with 112K or 112Q and 1D or 1E and 11V, 14P, 45R, 74S, 83R, 96P and 108L;
  89L in combination with 11V and 110K or 110Q; or
  89L in combination with 11V and 112K or 112Q;
and have CDRs which are in a CTLA4 binder of Table A, e.g., in SEQ ID NO: 1 or SEQ ID NO: 60 (e.g., according to Abm) and have an overall degree of sequence identity with the amino acid sequence of SEQ ID NO: 1 that are as described herein.

In another specific, but non-limiting aspect, the CTLA4 binders (e.g., ISVD such as a Nanobody) of the invention comprise the following sets of mutations (i.e. mutations compared to the sequence of SEQ ID NO: 1) at the positions mentioned (numbering according to Kabat):
  110K or 110Q in combination with 11V;
  110K or 110Q in combination with 89L;
  110K or 110Q in combination with 11V and 89L; or
  110K or 110Q in combination with 1D or 1E and 11V, 14P, 45R, 74S, 83R, 89L, 96P and 108L,
and have CDRs which are in a CTLA4 binder of Table A, e.g., in SEQ ID NO: 1 or SEQ ID NO: 60 (e.g., according to Abm) and have an overall degree of sequence identity with the amino acid sequence of SEQ ID NO: 1 that are as described herein.

In another specific, but non-limiting aspect, the CTLA4 binders (e.g., ISVD such as a Nanobody) of the invention comprise the following sets of mutations (i.e. mutations compared to the sequence of SEQ ID NO: 1) at the positions mentioned (numbering according to Kabat):
  112K or 112Q in combination with 11V;
  112K or 112Q in combination with 89L;
  112K or 112Q in combination with 11V and 89L; or
  112K or 112Q in combination with 1D or 1E and 11V, 14P, 45R, 74S, 83R, 89L, 96P and 108L,
and have CDRs which are in a CTLA4 binder of Table A, e.g., in SEQ ID NO: 1 or SEQ ID NO: 60 (e.g., according to Abm) and have an overall degree of sequence identity with the amino acid sequence of SEQ ID NO: 1 that are as described herein.

In another aspect, the CTLA4 binders (e.g., ISVD such as a Nanobody) of the invention comprise a T at position 89 and have CDRs such as those set forth in SEQ ID NO: 1 or 60 (e.g., according to Abm) and have an overall degree of sequence identity with the amino acid sequence of SEQ ID NO: 1 that are as described herein.

In another aspect, the CTLA4 binders (e.g., ISVD such as a Nanobody) of the invention comprise a V at position 11 and an L at position 89 and have CDRs such as those set forth in SEQ ID NO: 60 (e.g., according to Abm) and have an overall degree of sequence identity with the amino acid sequence of SEQ ID NO: 1 that are as described herein.

As mentioned, the CTLA4 binders (e.g., ISVD such as a Nanobody) of the invention according to the above aspects are preferably further such that they contain a suitable combination of an optional E1D mutation, an L11V mutation, A14P mutation, a Q45R mutation, an A74S mutation, a K83R mutation, a V89L mutation, an M96P mutation and a Q108L mutation, and preferably a suitable combination of Q108L with any one of the other A14P, Q45R, A74S and K83R mutations, and preferably in combination with any two of these other mutations, more preferably with any three of these mutations (such as with the combination A14P, A74S and K83R), such as with all of these mutations (and again, when the CTLA4 binder is monovalent or present at the N-terminal end of a CTLA4 binder of the invention, preferably also an E1D mutation). In an embodiment of the invention, the CTLA4 binders of the present invention comprise the mutations E1D (or lacking such a mutation, wherein residue 1 is E), L11V, A14P, Q45R, A74S, K83R, V89L, M96P, Q108L.

In another specific, but non-limiting aspect, the invention relates to a CTLA4 binder (e.g., an immunoglobulin single variable domain such as a Nanobody) that is or essentially consists of an amino acid sequence chosen from one of the following amino acid sequences: SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43 or SEQ ID NO: 60.

In another specific, but non-limiting aspect, the invention relates to a CTLA4 binder (e.g., an immunoglobulin single variable domain such as a Nanobody) that is or essentially consists of an amino acid sequence chosen from one of the following amino acid sequences: SEQ ID NO: 22, SEQ ID NO: 23, SEQ ID NO: 24, SEQ ID NO: 25, SEQ ID NO: 40, SEQ ID NO: 41, SEQ ID NO: 42, SEQ ID NO: 43 or SEQ ID NO: 60.

Also, as already indicated herein, the amino acid residues of a CTLA4 binder (e.g., an ISVD such as a Nanobody) are numbered according to the general numbering for VHs given by Kabat et al. ("Sequence of proteins of immunological interest", US Public Health Services, NIH Bethesda, Md., Publication No. 91), as applied to VHH domains from Camelids in the article of Riechmann and Muyldermans, J. Immunol. Methods 2000 Jun. 23; 240 (1-2): 185-195; or referred to herein. It should be noted that, as is well known in the art for VH domains and for VHH domains, the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence.

Alternative methods for numbering the amino acid residues of VH domains, which methods can also be applied in an analogous manner to VHH domains from Camelids and to Nanobodies, are the method described by Chothia et al. (Nature 342, 877-883 (1989)), the so-called "AbM definition" and the so-called "contact definition". However, in the present description, aspects and figures, the numbering according to Kabat as applied to VHH domains by Riechmann and Muyldermans will be followed, unless indicated otherwise.

The invention also relates to CTLA4 binders (e.g., ISVD such as a Nanobody); to methods for expressing/producing the CTLA4 binders of the invention; to compositions and products (such as pharmaceutical compositions and products) that comprise the CTLA4 binders of the invention; to polynucleotides that encode the CTLA4 binders of the invention; and to uses (and in particular therapeutic, prophylactic and diagnostic uses) of the CTLA4 binders of the invention.

These and other aspects, embodiments, advantages, applications and uses of the invention will become clear from the further description herein.

Accordingly, in a further aspect, the invention relates to polypeptides or other chemical entities that comprise or essentially consist of at least one (such as one, two or three) CTLA4 binding moieties described herein. These molecules themselves may be referred to as "CTLA4 binders" or "compounds of the invention" or "polypeptides of the invention".

CTLA4 binders (e.g., ISVD such as a Nanobody) of the invention can contain one or more other amino acid sequences, chemical entities or moieties. These other amino acid sequences, chemical entities or moieties can confer one or more desired properties to the resulting CTLA4 binders of the invention and/or can alter the properties of the resulting CTLA4 binders of the invention in a desired manner, for example to provide the resulting CTLA4 binders of the invention with a desired biological and/or therapeutic activity (for example, to provide the resulting CTLA4 binders of the invention with affinity and preferably potency against another therapeutically relevant target such that the resulting polypeptide becomes "bispecific" with respect to CTLA4 and that other therapeutically relevant target such as PD1, LAG3, BTLA and/or CD27), to provide a desired half-life and/or to otherwise modify or improve pharmacokinetic and/or pharmacodynamic properties, to target the CTLA4 binder to specific cells, tissues or organs (including cancer cells and cancer tissues), to provide a cytotoxic effect and/or to serve as a detectable tag or label. Some non-limiting examples of such other amino acid sequences, chemical entities or moieties are:

- one or more suitable linkers (such a 9GS, 15GS or 35GS linker (any combination of 9, 15 or 35 G and S amino acids such as, for example, GGGGSGGGGSGGGGSGGGGSGGGGSGGGGSGGGGS)) (SEQ ID NO: 65). In an embodiment of the invention, the linker is (GGGGS)$_n$(SEQ ID NO: 118), wherein n is 1, 2, 3, 4, 5, 6, 7, 8, 9 or 10; and/or
- one or more binding moieties, binding domains or binding units that are directed against a therapeutically relevant target other than CTLA4 (i.e. so as to provide a CTLA4 binder of the invention that is bispecific for both CTLA4 and the other therapeutically relevant target such as a different epitope of CTLA4, PD1, CD27, LAG3, BTLA, TIM3, ICOS, B7-H3, B7-H4, CD137, GITR, PD-L1, PD-L2, ILT1, ILT2 CEACAM1, CEACAM5, TIM3, TIGIT, VISTA, ILT3, ILT4, ILT5, ILT6, ILT7, ILT8, CD40, OX40, CD137, KIR2DL1, KIR2DL2, KIR2DL3, KIR2DL4, KIR2DL5A, KIR2DL5B, KIR3DL1, KIR3DL2, KIR3DL3, NKG2A, NKG2C, NKG2E, IL-10, IL-17, TSLP)) and/or
- one or more binding domains or binding units that provide for an increase in half-life (for example, a binding domain or binding unit that can bind against a serum protein such as serum albumin); and/or
- one or more binding moieties, binding domains or binding units that target the CTLA4 binder (e.g., ISVD such as a Nanobody) to a desired cell, tissue or organ (such as a cancer cell); and/or
- one or more binding moieties, binding domains or binding units that provide for increased specificity against CTLA4 (usually, these will be able to bind to CTLA4 but will generally by themselves essentially not be functional against CTLA4); and/or
- a binding moiety, binding domain, binding unit or other chemical entity that allows for the CTLA4 binder to be internalized into a (desired) cell (for example, an internalizing anti-EGFR Nanobody as described in WO 2005/044858); and/or
- a moiety that improves half-life such as a suitable polyethyleneglycol group (i.e. PEGylation) or an amino acid sequence that provides for increased half-life such as human serum albumin or a suitable fragment thereof (i.e. albumin fusion) or for example a serum albumin binding peptide as described in WO 2008/068280; and/or
- a payload such as a cytotoxic payload; and/or
- a detectable label or tag, such as a radiolabel or fluorescent label; and/or
- a tag that can help with immobilization, detection and/or purification of the CTLA4 binder, such as a HIS or FLAG3 tag; and/or
- a tag that can be functionalized, such as a C-terminal GGC or GGGC tag; and/or
- a C-terminal extension X(n), which may be as further described herein for the CTLA4 binders of the invention and/or as described in WO 2012/175741 or PCT/EP2015/060643 (WO2015/173325).

CTLA4 binders (e.g., ISVD such as a Nanobody) that also contain one or more parts or fragments of a (preferably human) conventional antibody (such as an Fc part or a functional fragment thereof or one or more constant domains) and/or from a Camelid heavy-chain only antibody (such as one or more constant domains) are part of the present invention.

Multispecific Binders

The present invention includes CTLA4 binders that may be fused in a single multivalent (e.g., multispecific) molecule that also binds to CTLA4 or to another polypeptide and, in an embodiment of the invention, such binders are linked to one or more half-life extenders that increases the half-life of the binders in the body of a subject (e.g., comprising the amino acid sequence set forth in SEQ ID NO: 62 or 64). In an embodiment of the invention, the half-life extender is an ISVD (e.g, a Nanobody) that specifically binds to human serum albumin (HSA), e.g., ALB11002. In an embodiment of the invention, the multispecific binder is F023700912 or F023700914 as described herein.

A polypeptide may be "fused to" another molecule either directly, with no linker, or through a linker such as a peptide linker, e.g., 35GS.

Multispecific binders may include a CTLA4 binder as well as a one or more binders that bind to an additional antigen such as CD27, PD1, :LAG3, BTLA, TIM3, ICOS, B7-H3, B7-H4, CD137, GITR, PD-L1, PD-L2, ILT1, ILT2 CEACAM1, CEACAM5, TIM3, TIGIT, VISTA, ILT3, ILT4, ILT5, ILT6, ILT7, ILT8, CD40, OX40, CD137, KIR2DL1, KIR2DL2, KIR2DL3, KIR2DL4, KIR2DL5A, KIR2DL5B, KIR3DL1, KIR3DL2, KIR3DL3, NKG2A, NKG2C, NKG2E, IL-10, IL-17 or TSLP.

For some specific but non-limiting examples of such ISVD-based or Nanobody-based biologicals, reference is to the various applications by Ablynx N.V., such as for example and without limitation WO 2004/062551, WO 2006/122825, WO 2008/020079 and WO 2009/068627, as well as for example, and without limitation, to applications such as WO 2006/038027, WO 2006/059108, WO 2007/063308, WO 2007/063311, WO 2007/066016 and WO 2007/085814. Also, as further described herein, a further moiety, which may be part of a molecule set forth in the applications mentioned above, may be an ISVD or Nanobody as described herein, directed against a (human) serum protein such as (human) serum albumin, and such an ISVD or Nanobody (e.g., ALB11002) may also find therapeutic uses, in particular in and/or for extending the half-life of the CTLA4 binders (and polypeptides comprising the same) that are described herein. Reference is for example made to WO 2004/041865, WO 2006/122787 and WO 2012/175400, which generally describe the use of serum-albumin binding Nanobodies for half-life extension. WO 2009/138519 (or in the prior art cited in WO 2009/138519) or WO 2008/020079 (or in the prior art cited in WO 2008/020079) are incorporated by reference. Also, where a method or technique is not specifically described herein, it can, in an embodiment of the invention, be performed as described in WO 2009/138519 (or in the prior art cited in WO 2009/138519) or WO 2008/020079 (or in the prior art cited in WO 2008/020079).

When the CTLA4 binders (e.g., ISVD such as a Nanobody) contain one or more further binding moieties, binding domains or binding units (e.g. a further essentially non-functional binding domain or binding unit against CTLA4 that provides for increased specificity against CTLA4, a binding moiety, binding domain or binding unit against a therapeutic target other than CTLA4, a binding moiety, binding domain or binding unit against a target such as human serum albumin that provides for increased half-life, and/or a binding moiety, binding domain or binding unit that targets the CTLA4 binder to a specific cell, tissue or organ and/or that allows for the CTLA4 binder to be internalized into a cell), these other binding moieties, binding domains or binding units preferably comprise one or more ISVDs, and more preferably are all ISVDs. For example and without limitation, these one or more further binding domains or binding units can be one or more Nanobodies (including a VHH, a humanized VHH and/or a camelized VHs such as camelized human VHs), a (single domain) antibody that is a VH domain or that is derived from a VH domain, a dAb that is or essentially consists of a VH domain or that is derived from a VH domain, or even a (single) domain antibody or a dAb that is or essentially consists of VL domain. In particular, these one or more binding domains or binding units, when present, may comprise one or more Nanobodies, and more in particular are all Nanobodies.

When a CTLA4 binder of the invention has an ISVD at its C-terminal end (which C-terminal ISVD may be a CTLA4 binding moiety described herein or may for example be, if present in the CTLA4 binder, a further essentially non-functional ISVD against CTLA4 that provides for increased specificity against CTLA4, an ISVD against a therapeutic target other than CTLA4, an ISVD against a target such as human serum albumin that provides for increased half-life, or an ISVD that targets the CTLA4 binder to a specific cell, tissue or organ and/or that allows for the CTLA4 binder to be internalized into a cell), then the CTLA4 binding moiety (i.e. said C-terminal ISVD) preferably has a C-terminal extension X(n), which C-terminal extension may be as described herein for the CTLA4 binders of the invention and/or as described in WO 2012/175741 or PCT/EP2015/060643 (WO2015/173325).

When a CTLA4 binder (e.g., ISVD such as a Nanobody) contains, in addition to the one or more CTLA4 binding moieties described herein, any further ISVDs (which one or more further ISVDs may, as mentioned, be a further essentially non-functional ISVD against CTLA4 that provides for increased specificity against CTLA4, an ISVD against a therapeutic target other than CTLA4, an ISVD against a target such as human serum albumin that provides for increased half-life, and/or an ISVD that targets the CTLA4 binder to a specific cell, tissue or organ and/or that allows for the CTLA4 binder to be internalized into a cell), and where such further ISVDs are Nanobodies or are ISVDs that are, that essentially consist of and/or that are derived from VH sequences, then according to a preferred aspect of the invention said one or more (and preferably all) further ISVDs present in the CTLA4 binder will contain within their sequence one or more framework mutations that reduce binding by pre-existing antibodies. In particular, according to this aspect of the invention, such further ISVDs may contain (a suitable combination of) amino acid residues/mutations at positions 11, 89, 110 and/or 112 that are as described in PCT/EP2015/060643 (WO2015/173325) and/or that essentially are as described herein for the CTLA4 binders of the invention. In one specific aspect, when the CTLA4 binder has such an ISVD at its C-terminal end (i.e. does not have CTLA4 binding moiety of the invention at its C-terminal end), then at least said ISVD that is present at and/or forms the C-terminal end has such framework mutations that reduce binding by pre-existing antibodies (and said C-terminal ISVD will preferably also have a C-terminal extension X(n) as described herein).

As mentioned, when the CTLA4 binder (e.g., ISVD such as a Nanobody) is to have an increased half-life (i.e. compared to the monovalent CTLA4 binder of the invention), the CTLA4 binder preferably contains at least one (such as one) ISVD (and in particular Nanobody) that provides for such increased half-life. Such an ISVD will usually be directed against a suitable serum protein such as transferrin and in particular against (human) serum albumin. In particular, such an ISVD or Nanobody may be a (single) domain antibody or dAb against human serum albumin as described in for example EP 2 139 918, WO 2011/006915, WO 2012/175400, WO 2014/111550 and may in particular be a serum albumin binding Nanobody as described in WO 2004/041865, WO 2006/122787, WO 2012/175400 or PCT/EP2015/060643 (WO2015/173325). Particularly preferred serum albumin binding ISVDs are the Nanobody Alb-1 (see WO 2006/122787) or its humanized variants such as Alb-8 (WO 2006/122787, SEQ ID NO: 62), Alb-23 (WO 2012/175400, SEQ ID NO: 1) and other humanized (and preferably also sequence-optimized) variants of Alb-1 and/or variants of Alb-8 or Alb-23 (or more generally ISVDs that have essentially the same CDRs as Alb-1, Alb-8 and Alb-23).

In an embodiment of the invention, the ISVD (e.g., Nanobody) is ALB11002 which binds to human serum albumin. ALB11002 is summarized below in Table C.

The present invention includes CTLA4 binders comprising an HSA binder of the invention, for example, having the same combination of CDRs (i.e. CDR1, CDR2 and CDR3) as are present in ALB11002 or in a binder comprising the sequence of SEQ ID NO: 66. See Table C.

TABLE C

Human Serum Albumin (HSA) Binder ALB11002

| SEQ ID NO | Description | Sequence |
|---|---|---|
| 66 | ALB11002 | EVQLVESGGG XVQPGNSLRL SCAASGFTFS SFGMSWVRQA PGKGLEWVSS ISGSGSDTLY ADSVKGRFTI SRDNAKTTLY LQMNSLRPED TAXYYCTIGG SLSRSSQGTL VTVSSA; wherein X at residues 11 and 93 are L or V; for example, EVQLVESGGGVVQPGNSLRLSCAASGF TFSSFGMSWVRQAPGKGLEWVSSISGSGS DTLYADSVKGRFTISRDNAKTTLYLQMNSLR PEDTALYYCTIGGSLSRSSQGTLVTVSS (SEQ ID NO: 112) |
| 67 | CDR1 | GFTFSSFGMS or SFGMS (SEQ ID NO: 113; amino acids 6-10 of SEQ ID NO: 67) |
| 68 | CDR2 | SISGSGSDTLYADSVKG or SISGSGSDTL (SEQ ID NO: 114; amino acids 1-10 of SEQ ID NO: 68) |
| 69 | CDR3 | GGSLSR |

Optionally, ALB lacks the C-terminal Alanine. In an embodiment of the invention, the HSA binder comprises the amino acid sequence of SEQ ID NO: 66 but including a mutation at position 1, 1, 89, 110 or 112, e.g., comprising a set of mutations set forth in Table C herein.

Residue 1 of SEQ ID NO: 66 can be D or E. If residue 1 is D, the HSA binder may be designated as 1D and if residue 1 is E, the HSA binder may be designated as 1E.

The present invention includes HSA binders comprising one, two or three of the CDRs of a HSA binder wherein each comprises 0, 1, 2, 3, 4, 5, 6, 7, 8, 9 or 10 amino acid substitutions, e.g., conservative substitutions, and/or comprises 100, 99, 98, 97, 96 or 95% sequence identity relative to the CDRs that are in the HSA binder sequences set forth of Table C or are set forth in SEQ ID NOs: 67-69, wherein an HSA binder having such CDRs retains the ability to bind to HSA.

In an embodiment of the invention, the half-life extender is an anti-HSA ISVD (e.g., a Nanobody) comprising:
a CDR1 that comprises the amino acid sequence GFTFSSFGMS (SEQ ID NO: 67); and
a CDR2 that comprises the amino acid sequence SISGSGSDTL (SEQ ID NO: 114; and
a CDR3 that comprises the amino acid sequence GGSLSR (SEQ ID NO: 69); and, optionally, having:
a degree of sequence identity with the amino acid sequence of SEQ ID NO: 66 (in which any C-terminal extension that may be present as well as the CDRs are not taken into account for determining the degree of sequence identity) of at least 85%, preferably at least 90%, more preferably at least 95% (in which the CDRs, any C-terminal extension that may be present, as well as the mutations at positions 1, 11, 89, 110 and/or 112 required by the specific aspect involved are not taken into account for determining the degree of sequence identity);
and/or
no more than 7, such as no more than 5, preferably no more than 3, such as only 3, 2 or 1 "amino acid differences" (as defined herein, and not taking into account any of the above-listed mutations at position(s) 1, 11, 89, 110 and/or 112 that may be present and not taking into account any C-terminal extension that may be present) with the amino acid sequence of SEQ ID NO: 66 (in which said amino acid differences, if present, may be present in the frameworks and/or the CDRs but are preferably present only in the frameworks and not in the CDRs);
and optionally having:
a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I).

Again, as mentioned, such a serum albumin binding ISVD, when present, may contain within its sequence one or more framework mutations that reduce binding by pre-existing antibodies. In particular, when such a serum albumin binding ISVD is a Nanobody or a (single) domain antibody that is, essentially consist of and/or is derived from a VH domain, the serum albumin binding ISVD may contain (a suitable combination of) amino acid residues/mutations at positions 11, 89, 110 and/or 112 that are as described in PCT/EP2015/060643 (WO2015/173325) and/or that essentially are as described herein for the CTLA4 binders of the invention. For example, PCT/EP2015/060643 (WO2015/173325) describes a number of variants of Alb-1, Alb-8 and Alb-23 that contain amino acid residues/mutations at positions 11, 89, 110 and/or 112 that reduce binding by pre-existing antibodies that can be used in the CTLA4 binders of the invention.

Again, when such a serum albumin binding ISVD is present at the C-terminal end of a CTLA4 binder (e.g., ISVD such as a Nanobody) of the invention, the serum albumin binding ISVD (and as a result, the CTLA4 binder of the invention) preferably has a C-terminal extension X(n), which C-terminal extension may be as described herein for the CTLA4 binders of the invention and/or as described in WO 2012/175741 or PCT/EP2015/060643 (WO2015/173325). It also preferably has mutations that reduce the binding of pre-existing antibodies, like (a suitable combination of) the amino acid residues/mutations at positions 11, 89, 110 and/or 112 described in PCT/EP2015/060643 (WO2015/173325).

However, as mentioned, other means of increasing the half-life of a CTLA4 binder of the invention (such as PEGylation, fusion to human albumin or a suitable fragment thereof, or the use of a suitable serum albumin-binding peptide), are also included in the scope of the invention.

Generally, when a CTLA4 binder (e.g., ISVD such as a Nanobody) of the invention has increased half-life (e.g. through the presence of a half-life increasing ISVD or any other suitable way of increasing half-life), the resulting CTLA4 binder preferably has a half-life (as defined herein) that is at least 2 times, preferably at least 5 times, for example at least 10 times or more than 20 times, greater than the half-life of the monovalent CTLA4 binder of the invention (as measured in either in man and/or a suitable animal model, such as mouse or cynomolgus monkey). In particular, a CTLA4 binder of the invention preferably has a half-life (as defined herein) in human subjects of at least 1 day, preferably at least 3 days, more preferably at least 7 days, such as at least 10 days.

It will be clear from the disclosure herein that CTLA4 binder of the invention (e.g., that are based on one or more ISVDs such as Nanobodies) can have different "formats", i.e. essentially be monovalent, bivalent or trivalent, can be monospecific, bispecific, trispecific etc., and can be biparatopic (as defined herein and in for example WO 2009/068625). For example, a CTLA4 binder of the invention can be:

- (essentially) monovalent, i.e. (essentially) comprising a single CTLA4 binding moiety of the invention. As mentioned, when used in monovalent format, a CTLA4 binder of the invention preferably has a C-terminal extension X(n) as further described herein. Such a CTLA4 binder of the invention may also be half-life extended;
- (essentially) bivalent or trivalent and monospecific. Such a CTLA4 binder of the invention will comprise two or more binding moieties (e.g., ISVDs) against CTLA4, which may be the same or different and when different may be directed against the same epitope on CTLA4 or against different epitopes on CTLA4 (in the latter case, so as to provide a biparatopic or multiparatopic CTLA4 binder of the invention). Such a CTLA4 binder of the invention may also be half-life extended;
- (essentially) bivalent, trivalent (or multivalent) and bispecific or trispecific (or multispecific). Such a CTLA4 binder of the invention will be directed against CTLA4 and at least one other target. As described herein, said other target may for example be another therapeutically relevant target (i.e. other than CTLA4), such as, for example, PD1, LAGS, BTLA and/or CD27, so as to provide a CTLA4 binder that is bispecific with regards to CTLA4 and said other therapeutic target. Said other target may also be a target that provides for increased half-life (such as human serum albumin), so as to provide a CTLA4 binder of the invention that has increased half-life. As also mentioned herein, such other target may allow also for the CTLA4 binder of the invention to be targeted to specific cells, tissues or organs or may allow for the CTLA4 binder of the invention to be internalized into a cell. It is also possible to combine these approaches/ISVDs, for example to provide a CTLA4 binder of the invention that is bispecific for CTLA4 and for at least one other therapeutically relevant target and that is half-life extended.

Again, preferably, when these CTLA4 binder (e.g., ISVD such as a Nanobody) of the invention contain one or more binding moieties (e.g., ISVDs) other than the at least one CTLA4 binder of the invention, at least one and preferably all of these other ISVDs will contain within its sequence one or more framework mutations that reduce binding by pre-existing antibodies (such as, in particular, a combination of amino acid residues/mutations at positions 11, 89, 110 and/or 112 that is as described herein for the CTLA4 binders of the invention and/or as generally described in PCT/EP2015/060643 (WO2015/173325)). Also, when such CTLA4 binder of the invention have a CTLA4 binding moiety at their C-terminal end, then said C-terminal CTLA4 binding moiety (and as a result, the CTLA4 binder of the invention) will preferably have a C-terminal extension X(n) as described herein. Similarly, when such CTLA4 binder of the invention have another ISVD at their C-terminal end (i.e. not a CTLA4 binding moiety of the invention, but for example a half-life extending ISVD), then said C-terminal ISVD (and as a result, the CTLA4 binder of the invention) will preferably have a C-terminal extension X(n) as described herein and/or will contain within its sequence one or more framework mutations that reduce binding by pre-existing antibodies (again, as further described herein and in PCT/EP2015/060643 (WO2015/173325)).

As will be clear to the skilled person, when a CTLA4 binder (e.g., ISVD such as a Nanobody) of the invention is intended for topical use (i.e. on the skin or in the eye) or is for example meant to have a (localized) therapeutic action somewhere in for example the GI tract (i.e. after oral administration or administration by suppository) or in the lungs (i.e. after administration by inhalation) or is otherwise meant to be directly applied to its intended place of action (for example, by direct injection), a CTLA4 binder of the invention may not require half-life extension. Also, for treatment of certain acute conditions or indications, it may be preferable not to have a prolonged half-life. In these cases, the use of a monovalent CTLA4 binder of the invention or of a CTLA4 binder of the invention (comprising the CTLA4 binding moiety of the invention) without half-life extension (for example, a CTLA4 binder of the invention that is bivalent or biparatopic with respect to CTLA4) is preferred.

Some preferred, but non-limiting examples of such CTLA4 binder (e.g., ISVD such as a Nanobody) of the invention are schematically represented in Table C-1 below, and each of these forms a further aspect of the invention. Other examples of suitable CTLA4 binders of the invention without half-life extension will be clear to the skilled person based on the disclosure herein.

TABLE C-1

Schematic representation of some CTLA4 binders of the invention without a half-life extending ISVD.

[CTLA4 binding moiety]
[CTLA4 binding moiety]-X(n)
[CTLA4 binding moiety]-[CTLA4 binding moiety]
[CTLA4 binding moiety]-[CTLA4 binding moiety]-X(n)
[CTLA4 binding moiety]-[Other]
[CTLA4 binding moiety]-[Other]-X(n)
[Other]-[CTLA4 binding moiety]
[Other]-[CTLA4 binding moiety]-X(n)
[CTLA4 binding moiety]-[Targeting unit]
[Targeting unit]-[CTLA4 binding moiety]
[CTLA4 binding moiety]-[Targeting unit]-X(n)
[Targeting unit]-[CTLA4 binding moiety]-X(n)
[CTLA4 binding moiety]-[CTLA4 binding moiety]-[Targeting unit]
[CTLA4 binding moiety]-[CTLA4 binding moiety]-[Targeting unit]-X(n)
[Targeting unit]-[CTLA4 binding moiety]-[CTLA4 binding moiety]
[Targeting unit]-[CTLA4 binding moiety]-[CTLA4 binding moiety]-X(n)

Legend:
"[CTLA4 binding moiety]" represents a CTLA4 binding domain or unit (e.g., an ISVD such as a Nanobody), e.g., 11F01 (E1D, L11V, A14P, Q45R, A74S, K83R, V89L, M96P, Q108L).
"—" represents either a direct covalent linkage or a suitable linker, such as a 9GS, 15GS or 35GS linker
"X(n)" represents a C-terminal extension as defined herein such as a single alanine residue.
"[Other]" represents a binding domain or binding unit (e.g., an ISVD such as a Nanobody) against CTLA4 different from the CTLA4 binding moiety or against a different antigen such as PD1, LAG3, CD27 and/or BTLA.
"[Targeting unit]" represents a binding domain or binding unit (e.g., an ISVD such as a Nanobody) that targets the CTLA4 binder of the invention to a specific cell, tissue or organ As will be clear to the skilled person, when a CTLA4 binder (e.g., ISVD such as a Nanobody) of the invention is intended for systemic administration and/or for prevention and/or treatment of a chronic disease or disorder, it will usually be preferred that said CTLA4 binder of the invention has increased half-life (as defined herein). More preferably, such a CTLA4 binder of the invention will contain a half-life extending ISVD such as, preferably, an ISVD and in particular a Nanobody binding to human serum albumin (as described herein).

Some preferred, but non-limiting examples of such CTLA4 binders (e.g., ISVD such as a Nanobody) of the invention are schematically represented in Table C-2 below, and each of these forms a further aspect of the invention. Other examples of suitable CTLA4 binder of the invention with half-life extension will be clear to the skilled person based on the disclosure herein. Generally, for CTLA4 binder of the invention with half-life extension, the presence of a C-terminal extension is much preferred.

TABLE C-2

Schematic Representation of Some CTLA4 Binders of the Invention with a Half-Life Extending ISVD.

[CTLA4 binding moiety]-[HLE]
[HLE]-[CTLA4 binding moiety]
[CTLA4 binding moiety]-[HLE]-X(n)
[HLE]-[CTLA4 binding moiety]-X(n)
[CTLA4 binding moiety]-[CTLA4 binding moiety]-[HLE]
[CTLA4 binding moiety]-[HLE]-[CTLA4 binding moiety]
[HLE]-[CTLA4 binding moiety]-[CTLA4 binding moiety]
[CTLA4 binding moiety]-[CTLA4 binding moiety]-[HLE]-X(n)
[CTLA4 binding moiety]-[HLE]-[CTLA4 binding moiety]-X(n)
[HLE]-[CTLA4 binding moiety]-[CTLA4 binding moiety]-X(n)
[CTLA4 binding moiety]-[Other]-[HLE]
[CTLA4 binding moiety]-[HLE]-[Other]
[HLE]-[CTLA4 binding moiety]-[Other]
[HLE]-[Other]-[CTLA4 binding moiety]
[Other]-[CTLA4 binding moiety]-[HLE]
[Other]-[HLE]-[CTLA4 binding moiety]
[CTLA4 binding moiety]-[Other]-[HLE]-X(n)
[CTLA4 binding moiety]-[HLE]-[Other]-X(n)
[HLE]-[CTLA4 binding moiety]-[Other]-X(n)
[HLE]-[Other]-[CTLA4 binding moiety]-X(n)

TABLE C-2-continued

Schematic Representation of Some CTLA4 Binders of the Invention with a Half-Life Extending ISVD.

[Other]-[CTLA4 binding moiety]-[HLE]-X(n)
[Other]-[HLE]-[CTLA4 binding moiety]-X(n)
[CTLA4 binding moiety]-[Targeting unit]-[HLE]
[CTLA4 binding moiety]-[HLE]-[Targeting unit]
[HLE]-[CTLA4 binding moiety]-[Targeting unit]
[Targeting unit]-[CTLA4 binding moiety]-[HLE]
[Targeting unit]-[HLE]-[CTLA4 binding moiety]
[HLE]-[Targeting unit]-[CTLA4 binding moiety]
[CTLA4 binding moiety]-[Targeting unit]-[HLE]-X(n)
[CTLA4 binding moiety]-[HLE]-[Targeting unit]-X(n)
[HLE]-[CTLA4 binding moiety]-[Targeting unit]-X(n)
[Targeting unit]-[CTLA4 binding moiety]-[HLE]-X(n)
[Targeting unit]-[HLE]-[CTLA4 binding moiety]-X(n)
[HLE]-[Targeting unit]-[CTLA4 binding moiety]-X(n)
[CTLA4 binding moiety]-[CTLA4 binding moiety]-[Targeting unit]-[HLE]
[CTLA4 binding moiety]-[CTLA4 binding moiety]-[HLE]-[Targeting unit]
[CTLA4 binding moiety]-[HLE]-[CTLA4 binding moiety]-[Targeting unit]
[HLE]-[CTLA4 binding moiety]-[CTLA4 binding moiety]-[Targeting unit]
[CTLA4 binding moiety]-[CTLA4 binding moiety]-[Targeting unit]-[HLE]-X(n)
[CTLA4 binding moiety]-[CTLA4 binding moiety]-[HLE]-[Targeting unit]-X(n)
[CTLA4 binding moiety]-[HLE]-[CTLA4 binding moiety]-[Targeting unit]-X(n)
[HLE]-[CTLA4 binding moiety]-[CTLA4 binding moiety]-[Targeting unit]-X(n)
[Targeting unit]-[CTLA4 binding moiety]-[CTLA4 binding moiety]-[HLE]
[Targeting unit]-[CTLA4 binding moiety]-[HLE]-[CTLA4 binding moiety]
[Targeting unit]-[HLE]-[CTLA4 binding moiety]-[CTLA4 binding moiety]
[HLE]-[Targeting unit]-[CTLA4 binding moiety]-[CTLA4 binding moiety]
[Targeting unit]-[CTLA4 binding moiety]-[CTLA4 binding moiety]-[HLE]-X(n)
[Targeting unit]-[CTLA4 binding moiety]-[HLE]-[CTLA4 binding moiety]-X(n)
[Targeting unit]-[HLE]-[CTLA4 binding moiety]-[CTLA4 binding moiety]-X(n)
[HLE]-[Targeting unit]-[CTLA4 binding moiety]-[CTLA4 binding moiety]-X(n)

Legend:
"[CTLA4 binding moiety]" represents a CTLA4 binding unit or domain (e.g., an ISVD such as a Nanobody), e.g., 11F01 (E1D, L11V, A14P, Q45R, A74S, K83R, V89L, M96P, Q108L).
"—" represents either a direct covalent linkage or a suitable linker, such as a 9GS, 15GS or 35GS linker
"X(n)" represents a C-terminal extension as defined herein such as a single alanine residue.
"[HLE]" represents a half-life extending binding domain or binding unit (and in particular a half-life extending ISVD), such as an ISVD (and in particular Nanobody) against (human) serum albumin, e.g., ALB11002;
"[Other]" represents a binding domain or binding unit (and in particular ISVD such as a Nanobody) against CTLA4 different from the "CTLA4 binding moiety" or against another antigen such as PD1, LAG3, CD27 and/or BTLA.
"[Targeting unit]" represents a binding domain or binding unit (and in particular ISVD such as a Nanobody) that targets the CTLA4 binder to a specific cell, tissue or organ The present invention also provides a CTLA4 ISVD, F023700912, comprising amino acid sequence:

DVQLVESGGGVVQPGGSLRLSCAASGGTFSFYGMG

WFRQAPGKEREFVADIRTSAGRTTYYADSVKGRFTISRDNSKNTVYLQMNSLRPEDTALYY

CAAEPSGISGWDYWGQGTLVTVSSGGGGSGGGGSGGGGSGGGGSGGGGSGGGGSGGGGSE

VQLVESGGGVVQPGGSLRLSCAASGGTFSFYGMGWFRQAPGKEREFVADIRTSAGRTTYYA

DSVKGRFTISRDNSKNTVYLQMNSLRPEDTALYYCAAEPSGISGWDYWGQGTLVTVSSGG

GGSGGGGSGGGGSGGGGSGGGGSGGGGSGGGGSEVQLVESGGGVVQPGNSLRLSCAASGF

TFSSFGMSWVRQAPGKGLEWVSSISGSGSDTLYADSVKGRFTISRDNAKTTLYLQMNSLR

PEDTALYYCTIGGSLSRSSQGTLVTVSSA (SEQ ID NO: 62; 35GS linkers underscored with dotted line; CDRs underscored and/or bold). Optionally, the first residue of any binder moiety in the molecule is substituted with a D or an E as appropriate.

Optionally, the CTLA4 ISVD comprises a signal peptide such as:

(SEQ ID NO: 70)
MRFPSIFTAVLFAASSALAAPVNTTTEDETAQIPAEAVIGYSDLEGDFDVA
VLPESNSTNNGLLFINTTIASIAAKEEGVSLEKR

F023700912 can be encoded by a polynucleotide comprising the following nucleotides:

```
gacgtgcaat tggtggagtc tggggagga gtggtgcagc cggggggctc tctgagactc    60
tcctgtgcag cctctggtgg caccttcagt ttctatggca tgggctggtt ccgccaggct   120
ccagggaagg agcgcgagtt tgtagcagat attagaacca gtgctggtag gacatactat   180
gcagactccg tgaagggccg attcaccatc tccagagaca acagcaagaa cacggtgtat   240
ctgcaaatga acagcctgcg ccctgaggac acggccctgt attactgtgc agcagagcca   300
agtggaataa gtggttggga ctactgggc caggggaccc tggtcacggt ctcctccgga   360
ggcggtgggt caggtggcgg aggcagcggt ggaggaggta gtgcggtgg cggtagtggg   420
ggtgaggca gcggaggcgg aggcagtggg ggcggtggat ccgaggtgca gttggtggag   480
tctgggggag gagtggtgca gccgggggc tctctgagac tctcctgtgc agcctctggt   540
ggcaccttca gttttctatgg catgggctgg ttccgccagg ctccagggaa ggagcgcgag   600
tttgtagcag atattagaac cagtgctggt aggacatact atgcagactc cgtgaagggc   660
cgattcacca tctccagaga caacagcaag aacacggtgt atctgcaaat gaacagcctg   720
cgccctgagg acacggccct gtattactgt gcagcagagc caagtggaat aagtggttgg   780
gactactggg gccagggaga cctggtcacg gtctcgagcg gaggcggtgg gtcaggtggc   840
ggaggcagcg gtggaggagg tagtgcggt ggcggtagtg gggtggagg cagcggaggc   900
ggaggcagtg gggcggtgg ctcagaggta aactagtgg agtctggagg tggcgttgtg   960
caaccgggta acagtctgcg ccttagctgc gcagcgtctg gctttacctt cagctccttt  1020
ggcatgagct gggttcgcca ggctccggga aaaggactgg aatgggtttc gtctattagc  1080
ggcagtggta gcgatacgct ctacgcggac tccgtgaagg gccgtttcac catctcccgc  1140
gataacgcca aaactacact gtatctgcaa atgaatagcc tgcgtcctga agatacggcc  1200
ctgtattact gtactattgg tggctcgtta agccgttctt cacagggtac cctggtcacc  1260
gtctcctcag cg                                                     1272
```

(SEQ ID NO: 61; optionally lacking the signal sequence of nucleotides 1-255) F023700912 comprises the following moieties:

CTLA4 binder 11F01(E1D,L11V,A14P,Q45R,A74S, K83R,V89L,M96P,Q108L) 35 GS linker

CTLA4 binder 11F01(L11V,A14P,Q45R,A74S,K83R, V89L,M96P,Q108L)

35 GS linker

Human serum albumin binder ALB11002;

C-terminal extension alanine.

For example:

CTLA4 binder SEQ ID NO: 60

35GS linker SEQ ID NO: 65

CTLA4 binder SEQ ID NO: 60 (D1E)

35GS linker SEQ ID NO: 65

Human serum albumin binder SEQ ID NO: 66

Alanine (the present invention includes any binder including such an arrangement of moieties)

The present invention also provides a CTLA4 ISVD, F023700914, comprising amino acid sequence:

DVQLVESGGGVVQPGGSLRLSCAASGGTFSFYGMG

WFRQAPGKEREFVADIRTSAGRTYYADSVKGRFTISRDNSKNTVYLQMNSLRPEDTALYY

CAAEPSGISGWDYWGQGTLVTVSSGGGGSGGGGSGGGGSGGGGSGGGGSGGGGSGGGGSE

VQLVESGGGVVQPGNSLRLSCAASGFTFSSFGMSWVRQAPGKGLEWVSSISGSGSDTLYA

DSVKGRFTISRDNAKTTLYLQMNSLRPEDTALYYCTIGGSLSRSSQGTLVTVSSA (SEQ ID NO: 64; 35GS linker underscored with dotted line; CDRs underscored and/or bold). Optionally, the first residue of any binder moiety in the molecule is substituted with a D or an E as appropriate.

Optionally, the CTLA4 ISVD comprises a signal peptide such as:

(SEQ ID NO: 70)
MRFPSIFTAVLFAASSALAAPVNTTTEDETAQIPAEAVIGYSDLEGDFDV
AVLPESNSTNNGLLFINTTIASIAAKEEGVSLEKR

F023700914 can be encoded by a polynucleotide comprising the following nucleotides:

```
gacgtgcaat tggtggagtc tgggggagga gtggtgcagc cggggggctc tctgagactc    60
tcctgtgcag cctctggtgg caccttcagt ttctatggca tgggctggtt ccgccaggct   120
ccagggaagg agcgcgagtt tgtagcagat attagaacca gtgctggtag gacatactat   180
gcagactccg tgaagggccg attcaccatc tccagagaca acagcaagaa cacggtgtat   240
ctgcaaatga acagcctgcg ccctgaggac acggccctgt attactgtgc agcagagcca   300
agtggaataa gtggttggga ctactgggcc caggggaccc tggtcacggt ctcctccgga   360
ggcggtgggt caggtggcgg aggcagcggt ggaggaggta gtggcggtgg cggtagtggg   420
ggtggaggca gcggaggcgg aggcagtggg ggcggtggat ccgaggtgca gttggtggag   480
tctggaggtg gcgttgtgca accgggtaac agtctgcgcc ttagctgcgc agcgtctggc   540
tttaccttca gctcctttgg catgagctgg gttcgccagg ctccgggaaa aggactggaa   600
tgggtttcgt ctattagcgg cagtggtagc gatacgctct acgcggactc cgtgaagggc   660
cgtttcacca tctcccgcga taacgccaaa actacactgt atctgcaaat gaatagcctg   720
cgtcctgaag atacggccct gtattactgt actattggtg gctcgttaag ccgttcttca   780
cagggtaccc tggtcaccgt ctcctcagcg                                    810
```

(SEQ ID NO: 63; optionally lacking the signal sequence of nucleotides 1-255)

F023700914 comprises the following moieties:
CTLA4 binder 11F01 (E1D,L11V,A14P,Q45R,A74S, K83R,V89L,M96P,Q108L);
35 GS linker;
Human serum albumin binder ALB11002;
C-terminal extension alanine.
For example:
CTLA4 binder SEQ ID NO: 60
35GS linker SEQ ID NO: 65
Human serum albumin binder SEQ ID NO: 66
Alanine
(the present invention includes any binder including such an arrangement of moieties)

The present invention includes any multispecific CTLA4 binder comprising the amino acid sequence of SEQ ID NO: 62 or 64 or an amino acid sequence comprising 80% or more (e.g., 85%, 90%, 95%, 96%, 97%, 98% or 99%) amino acid sequence identity wherein the CTLA4 binder retains the ability to bind to CTLA4 and, optionally, HSA.

Epitope Binding and Cross-Blocking

Figure 13:
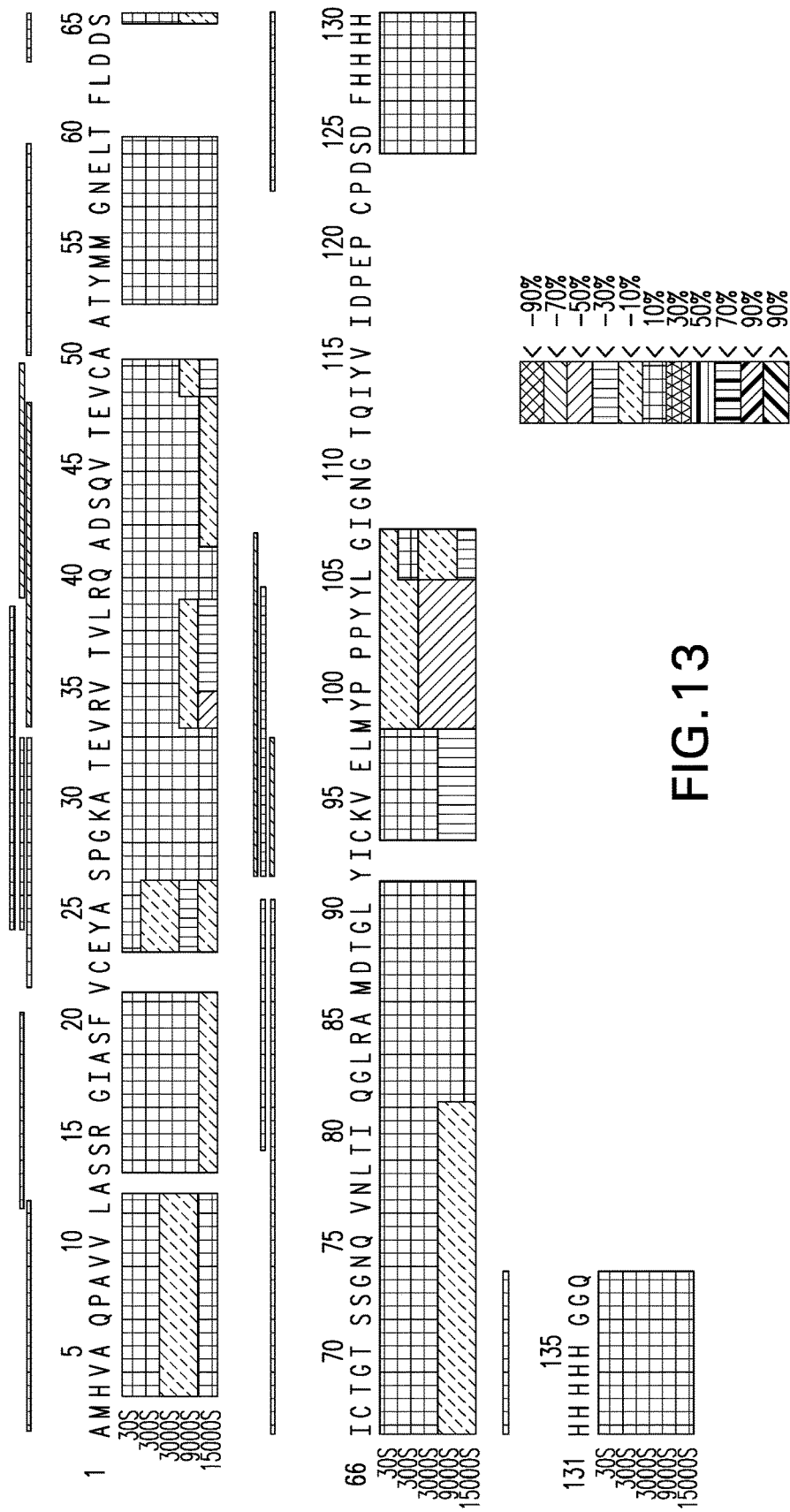
FIG. 13. Deuterium labeling difference heatmap of human CTLA4 binding by F023700912 CTLA4 binder.

The present invention provides CTLA4 binders set forth herein (e.g., F023700912 or F023700914) as well as binders, e.g., comprising CTLA4 ISVDs (e.g., Nanobodies) that bind to the same CTLA4 epitope of such binders. For example, the present invention includes binders that bind to human CTLA4 by contacting the same residues as F023700912 or F023700914. For example, the present invention provides binders that bind to human CTLA4 at residues VRVTVL (SEQ ID NO: 118; amino acids 33-38 of SEQ ID NO: 110), ADSQVTEVC (SEQ ID NO: 119; amino acids 41-49 of SEQ ID NO: 110) and CKVELMYPPPYYLG (SEQ ID NO:120; amino acids 93-106 of SEQ ID NO: 110), e.g., all three sites, of human CTLA4. In an embodiment of the invention, the binder demonstrates binding to human CTLA4 at these residues in a hydrogen-deuterium exchange assay, e.g., protects the residues from exchange of hydrogen for deuterium in the presence of deuterium such as $D_2O$, e.g., as represented by a binding heat map essentially as set forth in FIG. 13.

The present invention includes a CTLA4 binder (e.g., F023700912 or F023700914 or 11F01 or any of its variants set forth herein) that is bound to a polypeptide that comprises the peptide sequences VRVTVL (SEQ ID NO: 118; amino acids 33-38 of SEQ ID NO: 110), ADSQVTEVC (SEQ ID NO: 119; amino acids 41-49 of SEQ ID NO: 110) and CKVELMYPPPYYLG (SEQ ID NO:120; amino acids 93-106 of SEQ ID NO: 110), for example, CTLA4. Optionally, the polypeptide is on the surface of a cell, e.g., a T-cell and the polypeptide is bound by the CTLA4 binder.

The present invention also provides cross-blocking binders that are able to cross-block binding of any of the binders disclosed herein (e.g., F023700912 or F023700914). Such cross-blocking binders may be any molecule that exhibits such cross-blocking, e.g., an ISVD, Nanobody, antibody or antigen-binding fragment thereof.

In general, a binder (e.g., ISVD such as Nanobody) or antibody or antigen-binding fragment thereof that "cross-blocks" a reference binder refers to a binder (e.g., ISVD such as Nanobody) or antibody or antigen-binding fragment thereof that blocks binding of the reference binder to its antigen in a competition assay by 50% or more, and conversely, the reference binder blocks binding of the binder (e.g., ISVD such as Nanobody) or antibody or antigen-binding fragment thereof to its antigen in a competition assay by 50% or more. Cross-blocking can be determined any assay known in the art, including suface plasmon resonance (SPR), ELISA and flow cytometry.

In an embodiment of the invention, cross-blocking is determined by use of a Biacore assay. For convenience, reference is made to two binders, however, the scope of the present invention includes antibodies and antigen binding fragments thereof, e.g., Fab fragments, that cross-block a binder of the present invention. A Biacore machine (for example the Biacore 3000) is operated in line with the manufacturer's recommendations.

Thus, in one cross-blocking assay, CTLA4 is coupled to a CM5 Biacore chip using standard amine coupling chemistry to generate a CTLA4-coated surface. For example, 200-800 resonance units of CTLA4 would be coupled to the chip (or any amount that gives easily measurable levels of binding but that is readily saturable by the concentrations of test reagent being used).

The two binders (termed A* and B*) to be assessed for their ability to cross-block each other are mixed at a one to one molar ratio of binding sites in a suitable buffer to create the test mixture.

The concentration of each binder in the test mix should be high enough to readily saturate the binding sites for that binder on the CTLA4 molecules captured on the Biacore chip. The binders in the mixture are at the same molar concentration.

Separate solutions containing binder A* alone and binder B* alone are also prepared. Binder A* and binder B* in these solutions should be in the same buffer and at the same concentration as in the test mix.

The test mixture is passed over the CTLA4-coated Biacore chip and the total amount of binding recorded. The chip is then treated in such a way as to remove the bound binders without damaging the chip-bound CTLA4. In an embodiment of the invention, this is done by treating the chip with 30 mM HCl for 60 seconds.

The solution of binder A* alone is then passed over the CTLA4-coated surface and the amount of binding recorded. The chip is again treated to remove all of the bound binder without damaging the chip-bound CTLA4.

The solution of binder B* alone is then passed over the CTLA4-coated surface and the amount of binding recorded.

The maximum theoretical binding of the mixture of binder A* and binder B* is next calculated, and is the sum of the binding of each binder when passed over the CTLA4 surface alone. If the actual recorded binding of the mixture is less than this theoretical maximum, then the two binders are cross-blocking each other.

Thus, in general, a cross-blocking binder according to the invention is one which will bind to CTLA4 in the above Biacore cross-blocking assay such that, during the assay and in the presence of a second binder, the recorded binding is between, for example, 80% and 0.1% (e.g., 80% to 4%) of the maximum theoretical binding, for example between 75% and 0.1% (e.g., 75% to 4%) of the maximum theoretical binding, for example, between 70% and 0.1% (e.g., 70% to 4%) of maximum theoretical binding (as just defined above) of the two binders in combination.

In an embodiment of the invention, an ELISA assay is used for determining whether a CTLA4 binder cross-blocks or is capable of cross-blocking according to the invention.

The general principal of the assay is to have an CTLA4 binder coated onto the wells of an ELISA plate. An excess amount of a second, potentially cross-blocking, CTLA4 binder is added in solution (i.e., not bound to the ELISA plate). A limited amount of CTLA4 is then added to the wells. The coated binder and the binder in solution compete for binding of the limited number of CTLA4 molecules. The plate is washed to remove CTLA4 that has not been bound by the coated binder and to also remove the second, solution phase binder as well as any complexes formed between the second, solution phase binder and CTLA4. The amount of bound CTLA4 is then measured using an appropriate CTLA4 detection reagent. A binder in solution that is able to cross-block the coated binder will be able to cause a decrease in the number of CTLA4 molecules that the coated binder can bind relative to the number of CTLA4 molecules that the coated binder can bind in the absence of the second, solution phase, binder.

Expression Methods

The present invention includes recombinant methods for making an CTLA4 binders (e.g., an ISVD such as a Nanobody) of the present invention (e.g., F023700912 or F023700914) comprising (i) introducing a polynucleotide encoding the amino acid sequence of said CTLA4 binder, for example, wherein the polynucleotide is in a vector and/or is operably linked to a promoter; (ii) culturing the host cell (e.g., CHO or *Pichia* or *Pichia pastoris*) under condition favorable to expression of the polynucleotide and, (iii) optionally, isolating the CTLA4 binder from the host cell and/or medium in which the host cell is grown. See e.g., WO 04/041862, WO 2006/122786, WO 2008/020079, WO 2008/142164 or WO 2009/068627.

The invention also relates to polynucleotides that encode CTLA4 binders of the present invention (e.g., an ISVD such as a Nanobody) as described herein (e.g., F023700912 or F023700914). The polynucleotides may, in an embodiment of the invention, be operably linked to one or more control sequences. The polynucleotide may be in the form of a plasmid or vector. Again, such polynucleotides can be generally as described in the published patent applications of Ablynx N.V., such as for example WO 04/041862, WO 2006/122786, WO 2008/020079, WO 2008/142164 or WO 2009/068627.

The invention also relates to hosts or host cells that contain such polynucleotides, vectors, and/or CTLA4 binders described herein (e.g., F023700912 or F023700914). Again, such host cells can be generally as described in the published patent applications of Ablynx N.V., such as for example WO 04/041862, WO 2006/122786, WO 2008/020079, WO 2008/142164 or WO 2009/068627. Examples of specific host cells are discussed below.

Eukaryotic and prokaryotic host cells, including mammalian cells as hosts for expression of the CTLA4 binder (e.g., ISVD such as a Nanobody) are well known in the art and include many immortalized cell lines available from the American Type Culture Collection (ATCC). These include, inter alia, Chinese hamster ovary (CHO) cells, NS0, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines (e.g., *Spodoptera frugiperda* or *Trichoplusia ni*), amphibian cells, bacterial cells, plant cells and fungal cells. Fungal cells include yeast and filamentous fungus cells including, for example, *Pichia pastoris, Pichia finlandica, Pichia trehalophila, Pichia koclamae, Pichia membranaefaciens, Pichia minuta* (*Ogataea minuta, Pichia* lindneri),

*Pichia opuntiae, Pichia thermotolerans, Pichia salictaria, Pichia guercuum, Pichia* pijperi, *Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens* and *Neurospora crassa. Pichia* sp., any *Saccharomyces* sp., *Hansenula polymorpha,* any *Kluyveromyces* sp., *Candida albicans,* any *Aspergillus* sp., *Trichoderma reesei, Chrysosporium lucknowense,* any *Fusarium* sp., *Yarrowia lipolytica,* and *Neurospora crassa.* The present invention includes any host cell (e.g., a CHO cell or *Pichia* cell, e.g., *Pichia pastoris*) containing an CTLA4 binder of the present invention (e.g., F023700912 or F023700914) or containing a polynucleotide encoding such a binder or containing a vector that contains the polynucleotide.

Further, expression of a CTLA4 binder (e.g., an ISVD such as a Nanobody) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4. Thus, in an embodiment of the invention, the mammalian host cells (e.g., CHO) lack a glutamine synthetase gene and are grown in the absence of glutamine in the medium wherein, however, the polynucleotide encoding the immunoglobulin chain comprises a glutamine synthetase gene which complements the lack of the gene in the host cell. Such host cells containing the binder or polynucleotide or vector as discussed herein as well as expression methods, as discussed herein, for making the binder using such a host cell are part of the present invention.

The present invention includes methods for purifying a CTLA4 binder (e.g., ISVD such as a Nanobody) comprising introducing a sample (e.g., culture medium, cell lysate or cell lysate fraction, e.g., a soluble fraction of the lysate) comprising the CTLA4 binder to a purification medium (e.g., cation-exchange medium, anion-exchange medium, hydrophobic exchange medium, affinity purification medium (e.g., protein-A, protein-G, protein-A/G, protein-L)) and either collecting purified CTLA4 binder from the flow-through fraction of said sample that does not bind to the medium; or, discarding the flow-through fraction and eluting bound CTLA4 binder from the medium and collecting the eluate. In an embodiment of the invention, the medium is in a column to which the sample is applied. In an embodiment of the invention, the purification method is conducted following recombinant expression of the antibody or fragment in a host cell, e.g., wherein the host cell is first lysed and, optionally, the lysate is purified of insoluble materials prior to purification on a medium; or wherein the CTLA4 binder is secreted into the culture medium by the host cell and the medium or a fraction thereof is applied to the purification medium.

In general, glycoproteins produced in a particular cell line or transgenic animal will have a glycosylation pattern that is characteristic for glycoproteins produced in the cell line or transgenic animal. Therefore, the particular glycosylation pattern of a CTLA4 binder (e.g., ISVD such as a Nanobody) will depend on the particular cell line or transgenic animal used to produce the CTLA4 binder. CTLA4 binders comprising only non-fucosylated N-glycans are part of the present invention and may be advantageous, because non-fucosylated antibodies have been shown to typically exhibit more potent efficacy than their fucosylated counterparts both in vitro and in vivo (See for example, Shinkawa et al., J. Biol. Chem. 278: 3466-3473 (2003); U.S. Pat. Nos. 6,946, 292 and 7,214,775). These CTLA4 binders with non-fucosylated N-glycans are not likely to be immunogenic because their carbohydrate structures are a normal component of the population that exists in human serum IgG.

Figure 4:
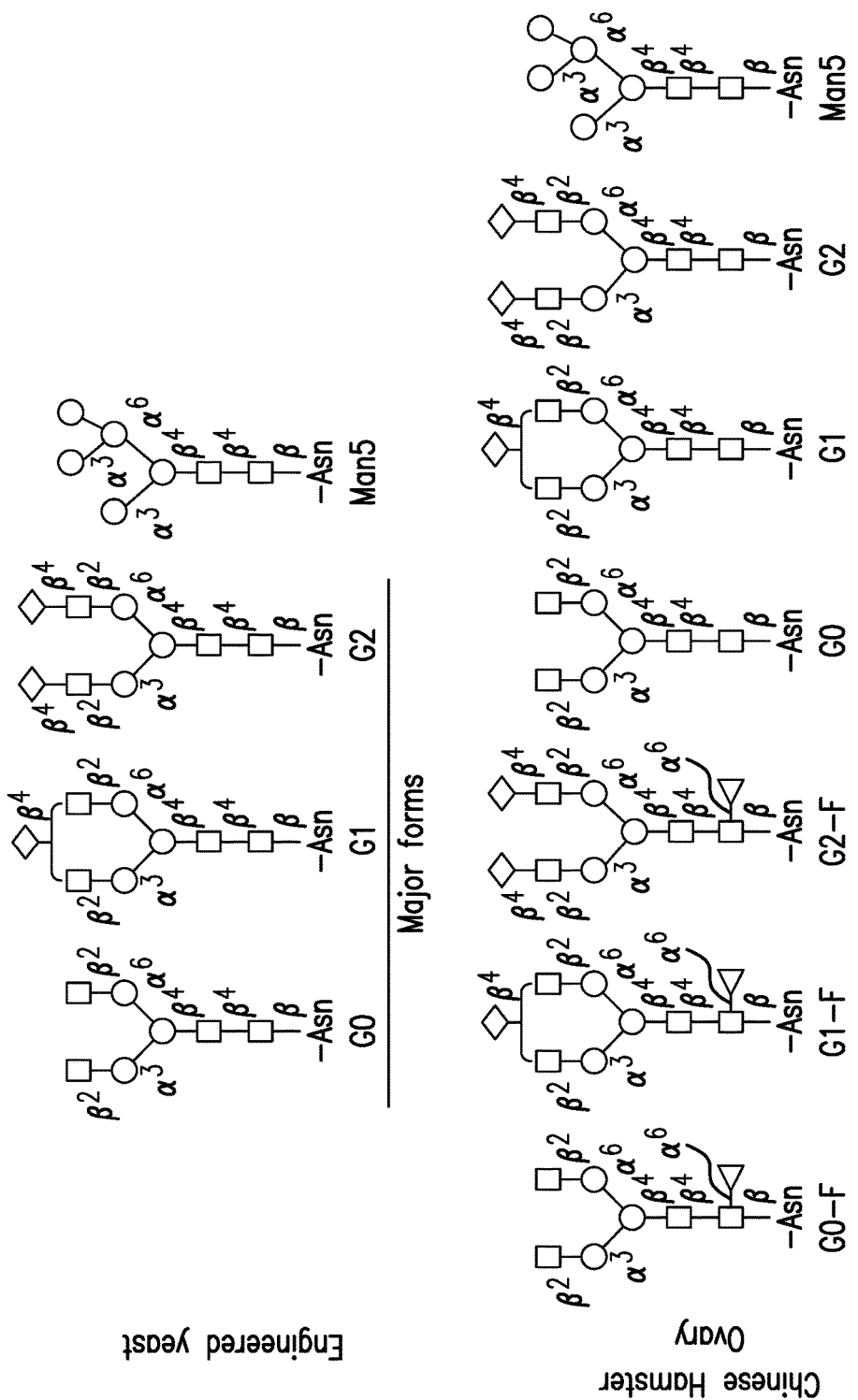

The present invention includes CTLA4 binders comprising N-linked glycans that are typically added to immunoglobulins produced in Chinese hamster ovary cells (CHO N-linked glycans) or to engineered yeast cells (engineered yeast N-linked glycans), such as, for example, *Pichia pastoris*. For example, in an embodiment of the invention, the CTLA4 binder (e.g., ISVD such as a Nanobody) comprises one or more of the "engineered yeast N-linked glycans" or "CHO N-linked glycans" that are set forth in FIG. 4 (e.g., G0 and/or G0-F and/or G1 and/or G1-F and/or and/or G2-F and/or Man5). In an embodiment of the invention, the CTLA4 binder comprises the engineered yeast N-linked glycans, i.e., G0 and/or G1 and/or G2, optionally, further including Man5. In an embodiment of the invention, the CTLA4 binders comprise the CHO N-linked glycans, i.e., G0-F, G1-F and G2-F, optionally, further including G0 and/or G1 and/or G2 and/or Man5. In an embodiment of the invention, about 80% to about 95% (e.g., about 80-90%, about 85%, about 90% or about 95%) of all N-linked glycans on the CTLA4 binders are engineered yeast N-linked glycans or CHO N-linked glycans. See Nett et al. Yeast. 28(3): 237-252 (2011); Hamilton et al. Science. 313(5792): 1441-1443 (2006); Hamilton et al. Curr Opin Biotechnol. 18(5): 387-392 (2007). For example, in an embodiment of the invention, an engineered yeast cell is GFI5.0 or YGLY8316 or strains set forth in U.S. Pat. No. 7,795,002 or Zha et al. Methods Mol Biol. 988:31-43 (2013). See also international patent application publication no. WO2013/066765.

Combinations

In particular embodiments, the CTLA4 binders (e.g., ISVD such as a Nanobody) of the present invention may be used alone, or in association with other, further therapeutic agents and/or therapeutic procedures, for treating or preventing any disease such as cancer, e.g., as discussed herein, in a subject in need of such treatment or prevention. Compositions or kits, e.g., pharmaceutical compositions comprising a pharmaceutically acceptable carrier, comprising such CTLA4 binders in association with further therapeutic agents are also part of the present invention.

The term "in association with" indicates that the components, a CTLA4 binder (e.g., ISVD such as a Nanobody) of the present invention along with another agent such as pembrolizumab or nivolumab, can be formulated into a single composition, e.g., for simultaneous delivery, or formulated separately into two or more compositions (e.g., a kit). Each component can be administered to a subject at a different time than when the other component is administered; for example, each administration may be given non-simultaneously (e.g., separately or sequentially) at intervals over a given period of time. Moreover, the separate components may be administered to a subject by the same or by a different route (e.g., wherein a CTLA4 binder of the present invention is administered parenterally and paclitaxel is administered orally).

In particular embodiments, the CTLA4 binders (e.g., ISVD such as a Nanobody) may be used in association with an anti-cancer therapeutic agent or immunomodulatory drug such as an immunomodulatory receptor inhibitor, e.g., an antibody or antigen-binding fragment thereof that specifically binds to the receptor.

In an embodiment of the invention, a CTLA4 binder (e.g., ISVD such as a Nanobody) is in association with one or more of an inhibitors (e.g., a small organic molecule or an antibody or antigen-binding fragment thereof) such as: an MTOR (mammalian target of rapamycin) inhibitor, a cytotoxic agent, a platinum agent a BRAF inhibitor, a CDK4/6 inhibitor an EGFR inhibitor, a VEGF inhibitor, a microtubule stabilizer, a taxane, a CD20 inhibitor, a CD52 inhibitor, a CD30 inhibitor, a RANK (Receptor activator of nuclear factor kappa-B) inhibitor, a RANKL (Receptor activator of nuclear factor kappa-B ligand) inhibitor, an ERK inhibitor, a MAP Kinase inhibitor, an AKT inhibitor, a MEK inhibitor, a PI3K inhibitor, a HER1 inhibitor, a HER2 inhibitor, a HER3 inhibitor, a HER4 inhibitor, a Bcl2 inhibitor, a CD22 inhibitor, a CD79b inhibitor, an ErbB2 inhibitor, or a farnesyl protein transferase inhibitor.

In an embodiment of the invention, a CTLA4 binder (e.g., ISVD such as a Nanobody) is in association with one or more of: anti-CTLA4 antibodies or antigen-binding fragments thereof (e.g., ipilimumab), anti-PD1 antibody or antigen-binding fragment thereof (e.g., pembrolizumab, nivolumab, CT-011), anti-PDL1, anti-CTLA4, anti-TIM3, anti-CS1, (e.g., elotuzumab), anti-KIR2DL1/2/3 (e.g., lirilumab), anti-CD27, anti-CD137 (e.g., urelumab), anti-GITR (e.g., TRX518), anti-PD-L1 (e.g., BMS-936559, MSB0010718C or MPDL3280A), anti-PD-L2, anti-ILT1, anti-ILT2, anti-ILT3, anti-ILT4, anti-ILT5, anti-ILT6, anti-ILT7, anti-ILT8, anti-CD40, anti-OX40, anti-CD137, anti-KIR2DL1, anti-KIR2DL2/3, anti-KIR2DL4, anti-KIR2DL5A, anti-KIR2DL5B, anti-KIR3DL1, anti-KIR3DL2, anti-KIR3DL3, anti-NKG2A, anti-NKG2C, anti-NKG2E, or any small organic molecule inhibitor of such targets; IL-10, anti-IL10, anti-TSLP (thymic stromal lymphopoietin) or PEGylated IL-10.

In an embodiment of the invention, the molecular weight of the polyethylene glycol (PEG) moiety, on a PEGylated IL-10 molecule, is about 12,000 daltons or about 20,000 daltons. In an embodiment of the invention, PEGylated IL-10 (e.g., PEGylated human IL-10) comprises one or more polyethylene glycol molecules covalently attached via a linker (e.g., $C_{2-12}$ alkyl such as —$CH_2CH_2CH_2$—) to a single amino acid residue of a single subunit of IL-10, wherein said amino acid residue is the alpha amino group of the N-terminal amino acid residue or the epsilon amino group of a lysine residue. In an embodiment of the invention PEGylated IL-10 is: (PEG) b-L-NH-IL-10; wherein b is 1-9 and L is a $C_{2-12}$ alkyl linker moiety covalently attached to a nitrogen (N) of the single amino acid residue of the IL-10. In an embodiment of the invention, the IL-10 of PEGylated IL-10 has the formula: $[X-O(CH_2CH_2O)_n]_b$-L-NH-IL-10, wherein X is H or $C_{1-4}$ alkyl; n is 20 to 2300; b is 1 to 9; and L is a $C_{1-11}$ alkyl linker moiety which is covalently attached to the nitrogen (N) of the alpha amino group at the amino terminus of one IL-10 subunit; provided that when b is greater than 1, the total of n does not exceed 2300. See U.S. Pat. No. 7,052,686.

In an embodiment of the invention, the anti-IL-10 antibody or antigen-binding fragment thereof (e.g., humanized antibody) comprises the CDRs set forth below:

CDR-L1:
KTSQNIFENLA; (SEQ ID NO: 71)

CDR-L2:
NASPLQA; (SEQ ID NO: 72)

CDR-L3:
HQYYSGYT; (SEQ ID NO: 73)

CDR-H1:
GFTFSDYHMA; (SEQ ID NO: 74)

CDR-H2:
SITLDATYTYYRDSVRG; (SEQ ID NO: 75)

CDR-H3:
HRGFSVWLDY; (SEQ ID NO: 76)

(See U.S. Pat. No. 7,662,379)

In an embodiment of the invention, the anti-TSLP antibody or antigen-binding fragment thereof (e.g., humanized antibody) comprises the CDRs set forth below:

CDR-H1:
GYIFTDYAMH; (SEQ ID NO: 77)

CDR-H2:
TFIPLLDTSDYNQNFK; (SEQ ID NO: 78)

CDR-H3:
MGVTHSYVMDA; (SEQ ID NO: 79)

CDR-L1:
RASQPISISVH; (SEQ ID NO: 80)

CDR-L2:
FASQSIS; (SEQ ID NO: 81)

CDR-L3:
QQTFSLPYT; (SEQ ID NO: 82)

(see WO2008/76321)

In an embodiment of the invention, the anti-CD27 antibody or antigen-binding fragment thereof (e.g., humanized antibody) comprises the CDRs set forth below:

CDR-H1:
GFIIKATYMH; (SEQ ID NO: 83)

CDR-H2:
RIDPANGETKYDPKFQV; (SEQ ID NO: 84)

CDR-H3:
YAWYFDV; (SEQ ID NO: 85)

CDR-L1:
RASENIYSFLA; (SEQ ID NO: 86)

CDR-L2:
(SEQ ID NO: 87)

-continued
```
HAKTLAE;

CDR-L3:
                                             (SEQ ID NO: 88)
QHYYGSPLT;
```

(See WO2012/04367).

Thus, the present invention includes compositions comprising a CTLA4 binder (e.g., ISVD such as a Nanobody) in association with pembrolizumab; as well as methods for treating or preventing cancer in a subject comprising administering an effective amount of the CTLA4 binder in association with pembrolizumab (e.g., pembrolizumab dosed at 200 mg once every three weeks) to the subject. Optionally, the subject is also administered in association with a another further therapeutic agent.

In an embodiment of the invention, a CTLA4 binder (e.g., ISVD such as a Nanobody) is in association with a pembrolizumab antibody which comprises an immunoglobulin heavy chain (or CDR-H1, CDR-H2 and CDR-H3 thereof) comprising the amino acid sequence:

```
                                             (SEQ ID NO: 89)
QVQLVQSGVEVKKPGASVKVSCKASGYTFTNYYMYWVRQAPGQGLEWMGG

INPSNGGTNENEKEKNRVTLTTDSSTTTAYMELKSLQFDDTAVYYCARRD

YREDMGEDYWGQGTTVTVSSASTKGPSVFPLAPCSRSTSESTAALGCLVK

DYFPEPVTVSWNSGALTSGVHTFPAVLQSSGLYSLSSVVTVPSSSLGTKT

YTCNVDHKPSNTKVDKRVESKYGPPCPPCPAPEFLGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK;
``` and an immunoglobulin light chain (or CDR-L1, CDR-L2 and CDR-L3 thereof) comprising the amino acid sequence:

```
                                             (SEQ ID NO: 90)
EIVLTQSPATLSLSPGERATLSCRASKGVSTSGYSYLHWYQQKPGQAPRL

LIYLASYLESGVPARFSGSGSGTDFTLTISSLEPEDFAVYYCQHSRDLPL

TFGGGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC.
```

In an embodiment of the invention, a CTLA4 binder (e.g., ISVD such as a Nanobody) is in association with an antibody comprising an immunoglobulin heavy chain (or CDR-H1, CDR-H2 and CDR-H3 thereof) comprising the amino acid sequence:

```
                                             (SEQ ID NO: 91)
QVQLVESGGGVVQPGRSLRLDCKASGITESNSGMHWVRQAPGKGLEWVAV

IWYDGSKRYYADSVKGRETISRDNSKNTLFLQMNSLRAEDTAVYYCATND

DYWGQGTLVTVSSASTKGPSVFPLAPCSRSTSESTAALGCLVKDYFPEPV

TVSWNSGALTSGVHTFPAVLQSSGLYSLSSVVTVPSSSLGTKTYTCNVDH

KPSNTKVDKRVESKYGPPCPPCPAPEFLGGPSVFLFPPKPKDTLMISRTP

EVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLY

SRLTVDKSRWQEGNVFSCSVMHEALHNHYTQKSLSLSLGK;
``` and an immunoglobulin light chain (or CDR-L1, CDR-L2 and CDR-L3 thereof) comprising the amino acid sequence:

```
                                             (SEQ ID NO: 92)
EIVLTQSPATLSLSPGERATLSCRASQSVSSYLAWYQQKPGQAPRLLIYD

ASNRATGIPARFSGSGSGTDFTLTISSLEPEDFAVYYCQQSSNWPRTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.
```

In an embodiment of the invention, a CTLA4 binder is in association with any one or more of: 13-cis-retinoic acid, 3-[5-(methylsulfonylpiperadinemethyl)-indolyl]-quinolone, 4-hydroxytamoxifen, 5-deooxyuridine, 5'-deoxy-5-fluorouridine, 5-fluorouracil, 6-mecaptopurine, 7-hydroxystaurosporine, A-443654, abirateroneacetate, abraxane, ABT-578, acolbifene, ADS-100380, aflibercept, ALT-110, altretamine, amifostine, aminoglutethimide, amrubicin, amsacrine, anagrelide, anastrozole, angiostatin, AP-23573, ARQ-197, arzoxifene, AS-252424, AS-605240, asparaginase, ATI3387, AT-9263, atrasentan, axitinib, AZD1152, *Bacillus* Calmette-Guerin (BCG) vaccine, batabulin, BC-210, besodutox, bevacizumab, BGJ398, bicalutamide, Bio111, BIO140, BKM120, bleomycin, BMS-214662, BMS-247550, BMS-275291, BMS-310705, bortezimib, buserelin, busulfan, calcitriol, camptothecin, canertinib, capecitabine, carboplatin, carmustine, CC8490, CEA (recombinant vaccinia-carcinoembryonic antigen vaccine), cediranib, CG-1521, CG-781, chlamydocin, chlorambucil, chlorotoxin, cilengitide, cimitidine, cisplatin, cladribine, clodronate, cobimetnib, COL-3, CP-724714, cyclophosphamide, cyproterone, cyproteroneacetate, cytarabine, cytosinearabinoside, dabrafenib, dacarbazine, dacinostat, dactinomycin, dalotuzumab, danusertib, dasatanib, daunorubicin, decatanib, deguelin, denileukin, deoxycoformycin, depsipeptide, diarylpropionitrile, diethylstilbestrol, diftitox, DNE03, docetaxel, dovitinib, doxorubicin, droloxifene, edotecarin, yttrium-90 labeled-edotreotide, edotreotide, EKB-569, EMD121974, encorafenib, endostatin, enzalutamide, enzastaurin, epirubicin, epithilone B, ERA-923, erbitux, erlotinib, estradiol, estramustine, etoposide, everolimus, exemestane, ficlatuzumab, finasteride, flavopiridol, floxuridine, fludarabine, fludrocortisone, fluoxymesterone, flutamide, FOLFOX regimen, fulvestrant, galeterone, ganetespib, gefitinib, gemcitabine, gimatecan, glucopyranosyl lipid A, goserelin, goserelin acetate, gossypol, GSK461364, GSK690693, HMR-3339, hydroxyprogesteronecaproate, hydroxyurea, IC87114, idarubicin, idoxyfene, ifosfamide, IM862, imatinib, IMC-1C11, imiquimod, INC280, INCB24360, INO1001, interferon, interleukin-2, interleukin-12, ipilimumab, irinotecan, JNJ-16241199, ketoconazole, KRX-0402, lapatinib, lasofoxifene, LEE011, letrozole, leucovorin, leuprolide, leuprolide acetate, levamisole, liposome entrapped paclitaxel, lomustine, lonafarnib, lucanthone, LY292223, LY292696, LY293646, LY293684, LY294002, LY317615, LY3009120, marimastat, mechlorethamine, medroxyprogesteroneacetate, megestrolacetate, MEK162, melphalan, mercaptopurine, mesna, methotrexate, mithramycin, mitomycin, mitotane, mitoxantrone, a suspension of heat killed *Mycobacterium obuense*, tozasertib, MLN8054, natitoclax, neovastat, Neratinib, neuradiab, nilotinib, nilutimide, nolatrexed, NVP-BEZ235, oblimersen, octreotide, ofatumumab, oregovomab, ornatuzumab, orteronel, oxaliplatin, paclitaxel, palbociclib, pamidronate, panitumumab, pazopanib, PD0325901, PD184352, PEG-interferon, pemetrexed, pentostatin, perifosine, phenylalaninemustard, PI-103, pictilisib, PIK-75, pipendoxifene, PKI-166, plicamycin, polyICLC, porfimer, prednisone, procarbazine, progestins, PSK protein bound polysaccharide (derived from Basidiomycete *coriolus versicolor*), PLX8394, PX-866, R-763, raloxifene, raltitrexed, razoxin, ridaforolimus, rituximab, romidepsin, RTA744, rubitecan, scriptaid, Sdx102, seliciclib, selumetinib, semaxanib, SF1126, sirolimus, SN36093, sorafenib, spironolactone, squalamine, SR13668, streptozocin, SU6668, suberoylanalide hydroxamic acid, sunitinib, synthetic estrogen, talampanel, talimogene laherparepvec, tamoxifen, temozolomide, temsirolimus, teniposide, tesmilifene, testosterone, tetrandrine, TGX-221, thalidomide, 6-thioguanine, thiotepa, ticilimumab, tipifarnib, tivozanib, TKI-258, TLK286, TNF☐ (tumor necrosis factor alpha), topotecan, toremifene citrate, trabectedin, trametinib, trastuzumab, tretinoin, trichostatin A, triciribinephosphate monohydrate, triptorelin pamoate, TSE-424, uracil mustard, valproic acid, valrubicin, vandetanib, vatalanib, VEGF trap, vemurafenib, vinblastine, vincristine, vindesine, vinorelbine, vitaxin, vitespan, vorinostat, VX-745, wortmannin, Xr311, Z-100 hot water extract of *Bacillus* tuberculosis, zanolimumab, ZK186619, ZK-304709, ZM336372 or ZSTK474.

In an embodiment of the invention, a CTLA4 binder (e.g., ISVD such as a Nanobody) is in association with one or more antiemetics including, but not limited to: casopitant (GlaxoSmithKline), Netupitant (MGI-Helsinn) and other NK-1 receptor antagonists, palonosetron (sold as Aloxi by MGI Pharma), aprepitant (sold as Emend by Merck and Co.; Rahway, N.J.), diphenhydramine (sold as Benadryl® by Pfizer; New York, N.Y.), hydroxyzine (sold as Atarax® by Pfizer; New York, N.Y.), metoclopramide (sold as Reglan® by AH Robins Co; Richmond, Va.), lorazepam (sold as Ativan® by Wyeth; Madison, N.J.), alprazolam (sold as Xanax® by Pfizer; New York, N.Y.), haloperidol (sold as Haldol® by Ortho-McNeil; Raritan, N.J.), droperidol (Inapsine®), dronabinol (sold as Marinol® by Solvay Pharmaceuticals, Inc.; Marietta, Ga.), dexamethasone (sold as Decadron® by Merck and Co.; Rahway, N.J.), methylprednisolone (sold as Medrol® by Pfizer; New York, N.Y.), prochlorperazine (sold as Compazine® by Glaxosmithkline; Research Triangle Park, NC), granisetron (sold as Kytril® by Hoffmann-La Roche Inc.; Nutley, N.J.), ondansetron (sold as Zofran® by by Glaxosmithkline; Research Triangle Park, NC), dolasetron (sold as Anzemet® by Sanofi-Aventis; New York, N.Y.), tropisetron (sold as Navoban® by Novartis; East Hanover, N.J.).

Other side effects of cancer treatment include red and white blood cell deficiency. Accordingly, in an embodiment of the invention, a CTLA4 binder (e.g., ISVD such as a Nanobody) is in association with an agent which treats or prevents such a deficiency, such as, e.g., filgrastim, PEG-filgrastim, erythropoietin, epoetin alfa or darbepoetin alfa.

In an embodiment of the invention, a CTLA4 binder (e.g., ISVD such as a Nanobody) is in association with a vaccine. In an embodiment of the invention, the vaccine is an anti-cancer vaccine, a peptide vaccine or a DNA vaccine. For example, in an embodiment of the invention, the vaccine is a tumor cell (e.g., an irradiated tumor cell) or a dendritic cell (e.g., a dendritic cell pulsed with a tumor peptide).

In an embodiment of the invention, a CTLA4 binder (e.g., ISVD such as a Nanobody) is administered in association with a therapeutic procedure. A therapeutic procedure is one or more steps carried out by a physician or clinician in treating a subject which is intended to alleviate one or more symptoms (e.g., of cancer and/or infectious disease) in the treated subject, whether by inducing the regression or elimination of such symptoms or by inhibiting the progression of such symptom(s), e.g., cancer symptoms such as tumor growth or metastasis, by any clinically measurable degree.

In an embodiment of the invention, a therapeutic procedure is anti-cancer radiation therapy. For example, in an embodiment of the invention, the radiation therapy is external beam therapy (EBT): a method for delivering a beam of high-energy X-rays to the location of the tumor. The beam is generated outside the patient (e.g., by a linear accelerator) and is targeted at the tumor site. These X-rays can destroy the cancer cells and careful treatment planning allows the surrounding normal tissues to be spared. No radioactive sources are placed inside the patient's body. In an embodiment of the invention, the radiation therapy is proton beam therapy: a type of conformal therapy that bombards the diseased tissue with protons instead of X-rays. In an embodiment of the invention, the radiation therapy is conformal external beam radiation therapy: a procedure that uses advanced technology to tailor the radiation therapy to an individual's body structures.

In an embodiment of the invention, the radiation therapy is brachytherapy: the temporary placement of radioactive materials within the body, usually employed to give an extra dose—or boost—of radiation to an area.

In an embodiment of the invention, a surgical procedure administered in association with a CTLA4 binder (e.g., ISVD such as a Nanobody) is surgical tumorectomy.

Therapeutic Uses

The invention includes a method for the preventing and/or treating at least one disease or disorder that can be prevented or treated by the use of a CTLA4 binder (e.g., ISVD such as a Nanobody) of the present invention, optionally in association with a further therapeutic agent or therapeutic procedure, which method comprises administering, to a subject in need thereof, a pharmaceutically active amount of the CTLA4 binder, and/or of a pharmaceutical composition comprising the same.

"Treat" or "treating" means to administer a CTLA4 binder (e.g., ISVD such as a Nanobody) of the present invention, to a subject (e.g., a mammal such as a human) having one or more symptoms of a disease for which the CTLA4 binders are effective, e.g., in the treatment of a subject having cancer or an infectious disease, or being suspected of having cancer or infectious disease, for which the agent has therapeutic activity. Typically, the CTLA4 binder is administered in an "effective amount" or "effective dose" which will alleviate one or more symptoms (e.g., of cancer or infectious disease) in the treated subject or population, whether by inducing the regression or elimination of such symptoms or by inhibiting the progression of such symptom(s), e.g., cancer symptoms such as tumor growth or metastasis, by any clinically measurable degree. The effective amount of the CTLA4 binder may vary according to factors such as the disease stage, age, and weight of the patient, and the ability of the drug to elicit a desired response in the subject.

The subject to be treated may be any warm-blooded animal, but is in particular a mammal, and more in particular a human being. As will be clear to the skilled person, the subject to be treated will in particular be a person suffering from, or at risk from, the diseases and disorders mentioned herein. Generally, the treatment regimen will be followed until the desired therapeutic effect is achieved and/or for as long as the desired therapeutic effect is to be maintained. Again, this can be determined by the clinician.

The CTLA4 binders (e.g., ISVD such as a Nanobody), polypeptides, compounds, and polynucleotides (e.g., vectors) described herein are preferably administered to the circulation. As such, they can be administered in any suitable manner that allows the CTLA4 binders, polypeptides, compounds, and polynucleotides to enter the circulation, such as intravenously, via injection or infusion, or in any other suitable manner (including oral administration, subcutaneous administration, intramuscular administration, administration through the skin, intranasal administration, administration via the lungs, etc.) that allows the CTLA4 binders, polypeptides, compounds, and polynucleotides to enter the circulation. Suitable methods and routes of administration will be clear to the skilled person, again for example also from the teaching of the published patent applications of Ablynx N.V., such as for example WO 04/041862, WO 2006/122786, WO 2008/020079, WO 2008/142164 or WO 2009/068627.

To prepare pharmaceutical or sterile compositions of the CTLA4 binders (e.g., ISVD such as a Nanobody) of the present invention, the CTLA4 binders is admixed with a pharmaceutically acceptable carrier or excipient. See, e.g., Remington's Pharmaceutical Sciences and U.S. Pharmacopeia: National Formulary, Mack Publishing Company, Easton, Pa. (1984) or Remington's Pharmaceutical Sciences. Such compositions are part of the present invention.

The scope of the present invention includes dessicated, e.g., freeze-dried, compositions comprising an CTLA4 binders (e.g., ISVD such as a Nanobody) or a pharmaceutical composition thereof that includes a pharmaceutically acceptable carrier but substantially lacks water.

Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

Generally, for the prevention and/or treatment of the diseases and disorders mentioned herein and depending on the specific disease or disorder to be treated, the potency and/or the half-life of the specific fusion proteins or constructs to be used, the specific route of administration and the specific pharmaceutical formulation or composition used, the Nanobodies and polypeptides of the invention will generally be administered in an amount between 1 gram and 0.01 microgram per kg body weight per day, preferably between 0.1 gram and 0.1 microgram per kg body weight per day, such as about 1, 10, 100 or 1000 microgram per kg body weight per day, either continuously (e.g., by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

The mode of administration of a CTLA4 binder (e.g., ISVD such as a Nanobody) to a subject can vary. Routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

Determination of the appropriate dose is made by the clinician, e.g., using parameters or factors known or suspected in the art to affect treatment. Generally, in determining the dose, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent. In the case of human subjects, for example, chimeric, humanized and fully human antibodies are may be desirable. Guidance in selecting appropriate doses is available (see, e.g., Wawrzynczak (1996) Antibody Therapy, Bios Scientific Pub. Ltd, Oxfordshire, UK; Kresina (ed.) (1991) Monoclonal Antibodies, Cytokines and Arthritis, Marcel Dekker, New York, N.Y.; Bach (ed.) (1993) Monoclonal Antibodies and Peptide Therapy in Autoimmune Diseases, Marcel Dekker, New York, N.Y.; Baert et al. (2003) New Engl. J. Med. 348:601-608; Milgrom et al. (1999) New Engl. J. Med. 341:1966-1973; Slamon et al. (2001) New Engl. J. Med. 344:783-792; Beniaminovitz et al. (2000) New Engl. J. Med. 342:613-619; Ghosh et al. (2003) New Engl. J. Med. 348:24-32; Lipsky et al. (2000) New Engl. J. Med. 343:1594-1602).

Whether a disease symptom has been alleviated can be assessed by any clinical measurement typically used by physicians or other skilled healthcare providers to assess the severity or progression status of that symptom. While an embodiment of the present invention (e.g., a treatment method or article of manufacture) may not be effective in alleviating the target disease symptom(s) in every subject, it should alleviate the target disease symptom(s) in a statistically significant number of subjects as determined by any statistical test known in the art such as the Student's t-test, the $chi^2$-test, the U-test according to Mann and Whitney, the Kruskal-Wallis test (H-test), Jonckheere-Terpstra-test and the Wilcoxon-test.

Generally, the treatment regimen will be followed until the desired therapeutic effect is achieved and/or for as long as the desired therapeutic effect is to be maintained. Again, this can be determined by the clinician.

As the CTLA4 binders (e.g., ISVD such as a Nanobody) of the present invention are capable of binding to CTLA4, they can in particular be used for treatment or prevention of cancer, metastatic cancer, a solid tumor, a hematologic cancer, leukemia, lymphoma, osteosarcoma, rhabdomyosarcoma, neuroblastoma, kidney cancer, leukemia, renal transitional cell cancer, bladder cancer, Wilm's cancer, ovarian cancer, pancreatic cancer, breast cancer, prostate cancer, bone cancer, lung cancer, non-small cell lung cancer, gastric cancer, colorectal cancer, cervical cancer, synovial sarcoma, head and neck cancer, squamous cell carcinoma, multiple myeloma, renal cell cancer, retinoblastoma, hepatoblastoma, hepatocellular carcinoma, melanoma, rhabdoid tumor of the kidney, Ewing's sarcoma, chondrosarcoma, brain cancer, glioblastoma, meningioma, pituitary adenoma, vestibular schwannoma, a primitive neuroectodermal tumor, medulloblastoma, astrocytoma, anaplastic astrocytoma, oligodendroglioma, ependymoma, choroid plexus papilloma, polycythemia vera, thrombocythemia, idiopathic myelfibrosis, soft tissue sarcoma, thyroid cancer, endometrial cancer, carcinoid cancer or liver cancer, breast cancer and gastric cancer.

CTLA4 binders (e.g., ISVD such as a Nanobody) of the present invention can be used for treatment or prevention of infectious diseases such as, for example, viral infection, bacterial infection, fungal infection or parasitic infection. In an embodiment of the invention, the viral infection is infection with a virus selected from the group consisting of human immunodeficiency virus (HIV), ebola virus, hepatitis virus (A, B, or C), herpes virus (e.g., VZV, HSV-I, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus or arboviral encephalitis virus. In an embodiment of the invention, the bacterial infection is infection with a bacteria selected from the group consisting of *Chlamydia*, rickettsial bacteria, mycobacteria, staphylococci, streptococci, pneumonococci, meningococci and gonococci, *klebsiella, proteus, serratia, pseudomonas, Legionella, Corynebacterium* diphtherias, *Salmonella*, bacilli, *Vibrio cholerae, Clostridium tetan, Clostridium botulinum, Bacillus anthricis, Yersinia pestis, Mycobacterium leprae, Mycobacterium* lepromatosis, and Borriella. In an embodiment of the invention, the fungal infection is infection with a fungus selected from the group consisting of *Candida (albicans, krusei, glabrata, tropicalis,* etc.), *Cryptococcus neoformans, Aspergillus (fumigatus, niger,* etc.), Genus Mucorales *(mucor, absidia, rhizopus), Sporothrix schenkii, Blastomyces dermatitidis, Paracoccidioides brasiliensis, Coccidioides immitis* and *Histoplasma capsulatum. In an embodiment of the invention, the parasitic infection is infection with a parasite selected from the group consisting of Entamoeba histolytica, Balantidium coli, Naegleria fowleri, Acanthamoeba, Giardia* Zambia, *Cryptosporidium, Pneumocystis carinii, Plasmodium vivax, Babesia microti, Trypanosoma brucei, Trypanosoma cruzi, Leishmania donovani, Toxoplasma gondii, Nippostrongylus brasiliensis*

The present invention also includes methods for:
  preventing CTLA4 mediated inhibition of: T-cell costimulatory signaling; T-cell activation, T-cell proliferation;
  preventing CTLA4 binding to B7-1 (CD80) or B7-2 (CD86); and/or
  enhancing T-cell activation
in the body of a subject by administering the CTLA4 binder (e.g., F023700912 or F023700914) to the subject; or in vitro by contacting CTLA4 with the CTLA4 binder. Such activities can be mediated via the CTLA4 binder. Thus, such methods may also be performed with any binder that includes a CTLA4 binder.

The invention also relates to methods of treatment of the aforementioned diseases and disorders, which generally comprise administering to a subject in need thereof (i.e. suffering from one of the aforementioned diseases) a therapeutically effective amount of a CTLA4 binder (e.g., ISVD such as a Nanobody) of the invention. The invention also relates to a CTLA4 binder of the invention for use in the prevention or treatment of one of the aforementioned diseases or disorders.

The present invention also provides an injection device comprising any of the CTLA4 binders (e.g., ISVD such as a Nanobody), polypeptides or polynucleotides set forth herein or a pharmaceutical composition thereof. An injection device is a device that introduces a substance into the body of a patient via a parenteral route, e.g., intramuscular, subcutaneous or intravenous. For example, an injection device may be a syringe (e.g., pre-filled with the pharmaceutical composition, such as an auto-injector) which, for example, includes a cylinder or barrel for holding fluid to be injected (e.g., comprising the CTLA4 binder or a pharmaceutical composition thereof), a needle for piecing skin and/or blood vessels for injection of the fluid; and a plunger for pushing the fluid out of the cylinder and through the needle bore. In an embodiment of the invention, an injection device that comprises an CTLA4 binder or a pharmaceutical composition thereof is an intravenous (IV) injection device. Such a device includes the CTLA4 binder or a pharmaceutical composition thereof in a cannula or trocar/needle which may be attached to a tube which may be attached to a bag or reservoir for holding fluid (e.g., saline; or lactated ringer solution comprising NaCl, sodium lactate, KCl, $CaCl_2$ and optionally including glucose) introduced into the body of the subject through the cannula or trocar/needle. The CTLA4 binder or a pharmaceutical composition thereof may, in an embodiment of the invention, be introduced into the device once the trocar and cannula are inserted into the vein of a subject and the trocar is removed from the inserted cannula. The IV device may, for example, be inserted into a peripheral vein (e.g., in the hand or arm); the superior vena cava or inferior vena cava, or within the right atrium of the heart (e.g., a central IV); or into a subclavian, internal jugular, or a femoral vein and, for example, advanced toward the heart until it reaches the superior vena cava or right atrium (e.g., a central venous line). In an embodiment of the invention, an injection device is an autoinjector; a jet injector or an external infusion pump. A jet injector uses a high-pressure narrow jet of liquid which penetrate the epidermis to introduce the CTLA4 binder or a pharmaceutical composition thereof to a patient's body. External infusion pumps are medical devices that deliver the CTLA4 binder or a pharmaceutical composition thereof into a patient's body in controlled amounts. External infusion pumps may be powered electrically or mechanically. Different pumps operate in different ways, for example, a syringe pump holds fluid in the reservoir of a syringe, and a moveable piston controls fluid delivery, an elastomeric pump holds fluid in a stretchable balloon reservoir, and pressure from the elastic walls of the balloon drives fluid delivery. In a peristaltic pump, a set of rollers pinches down on a length of flexible tubing, pushing fluid forward. In a multi-channel pump, fluids can be delivered from multiple reservoirs at multiple rates.

It should also be noted that the Figures, any Sequence Listing and the Experimental Part/Examples are only given to further illustrate the invention and should not be interpreted or construed as limiting the scope of the invention and/or of the appended claims in any way, unless explicitly indicated otherwise herein.

Other aspects, embodiments, advantages and applications of the invention will become clear from the further description herein.

EXAMPLES

These examples are intended to exemplify the present invention are not a limitation thereof. Compositions and methods set forth in the Examples form part of the present invention.

Example 1: F023700906 Nanobody Binding to CTLA-4-Fc

Monovalent F023700906 Nanobody 11F01 (L11V,A14P, Q45R,A74S,K83R, V89L,M96P,Q108L)-FLAG3-HIS6), a building block of F023700912, demonstrates binding to CTLA-4-Fc fusion molecule from both human and cynomolgus monkey. On-rate, off-rate and affinity were determined on a ProteOn XPR36 (BioRad 670BR0166) using human CTLA-4-hFc and cynomolgus monkey CTLA4-hFc (Table D below). These results demonstrate high-affinity binding of the Nanobody to human and cynomolgus monkey CTLA-4 suggesting potential for the Nanobody to modulate the function of CTLA-4 and that cynomolgus monkey may be used as a toxicology species.

irrelavant Nb (filled triangles) to (A) bulksorted hCTLA4-overexpressing jurkat JE6.2.11 cells or (B) hCTLA4-overexpressing CHO-K1 cells was studied by flow cytometry. Nanobodies were detected via the ALB11002-binding mAB ABH0074. The data generated in these experiments are set forth in FIG. 5 (A-B). These results demonstrate binding of the F023700912 and F023700925 to CTLA-4 expressed on cell surface suggesting that these Nanobodies modulate the function of CTLA-4.

Figure 5A:
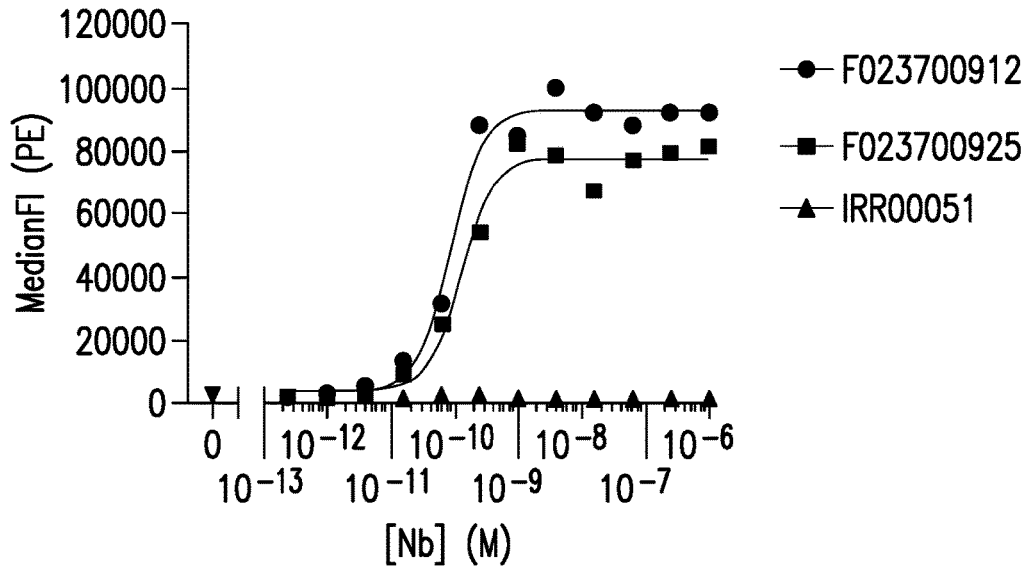
Figure 5B:
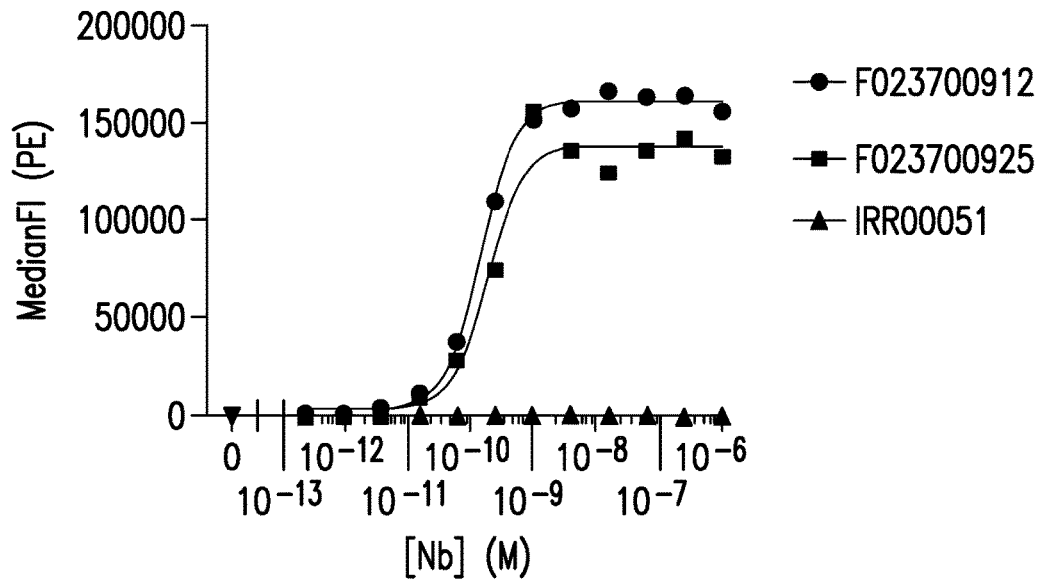

FIG. 5 (A-B) is a dilution series (start concentration 1/4 serial dilution, 12 pts) of batches of half-life extended (ALB0011 building block) Nbs F023700912 (filled circles), F023700925 (filled squares) and negative control Nb IRR00051 (filled triangles) in 200 µl FACS buffer (PBS (Life Technologies, 14190-094), 10% heat-inactivated foetal bovine serum (Sigma, F7524), 0.05% $NaN_3$ (ThermoScientific, 19038)) were added to (A) 2E4 bulksorted human CTLA4-overexpressing jurkat JE6.2.11 cells/well or (B) 2E4 human CTLA4-overexpressing CHO-K1 cells/well and incubated for 30 minutes at 4° C.

After three washing steps (1 washing step=removal of Nb dilutions, addition of 100 µl cold FACS buffer, centrifugation for 5 minutes at 250 g), the cells were incubated for 30 minutes at 4° C. with 3 µg/ml anti-ALB11002 mouse mAb ABH00074 in cold FACS buffer for detection of the half-life-extended Nanobodies.

After three washing steps, the cells were incubated for 30 minutes at 4° C. with a 1/100 dilution in cold FACS buffer of PE goat F(ab')2 anti-mouse IgG (Jackson ImmunoResearch, 115-116-071).

TABLE D-1

| Nanobody Binding to Human or Cynomolgous Monkey CTLA-4-Fc | | | | | | |
|---|---|---|---|---|---|---|
| | Human CTLA-4-Fc | | | Cynomolgus CTLA-4-Fc | | |
| | Ka (1/Ms) | Kd (1/s) | KD (M) | Ka (1/Ms) | Kd (1/s) | KD (M) |
| F023700906 | 4.8E+06 | 5.9E−03 | 1.2E−09 | 4.7E+06 | 5.7E−03 | 1.2E−09 |

TABLE D-2

| Reagents | | | | | |
|---|---|---|---|---|---|
| Reagent | Expression system | Conc. (mg/ml) | Formulation Buffer | SEC purity | RP purity |
| hCTLA4-Fc | HEK293F | 16.13 | 10 mM Sodium Phosphate, 75 mM NaCl, 3% Sucrose, pH = 7.4 | 94.86% (~150 KDa (tetramer) | 61.50% |
| cynoCTLA4-Fc | HEK293EBNA | 0.32 | PBS pH 7.4 | 81.58% | 83.50% |

Example 2: F023700912 Nanobody Binding to Cell Surface CTLA4

F023700912 demonstrates binding to human CTLA-4 expressed on cell surface. Binding of batches of F023700912 (11F01 (E1D,L11V,A14P,Q45R,A74S,K83R,V89L, M96P,Q108L)-35GS-11F01 (L11V,A14P,Q45R,A74S,K83R,V89L,M96P,Q108L)-35GS-ALB11002-AD (filled circles), F023700925 (PD1 binder-35GS-PD1 binder-35GS-11F01(L11V,A14P,Q45R,A74S,K83R,V89L,M96P,Q108L)-35GS-11F01(L11V,A14P,Q45R,A74S,K83R,V89L,M96P,Q108L)-35GS-ALB11002-A1) (filled squares) and an After three washing steps, the cells were resuspended in 50 µl cold FACS buffer supplemented with 5 nM TO-PRO-3 (Molecular Probes, T3605) and analyzed with a FACS Canto.

First, a P1 population is selected based on FSC-SSC distribution. Stopping gate was set on 10000 cells in P1. From this population the TO-PRO-3+cells (dead cells) are excluded. For this P1/TO-PRO-3-negative population the median PE value is calculated.

Example 3: F023700912 Nanobody Blocks Binding of CTLA-4 to CD80 and CD86

F023700912 block binding of human CTLA-4 to its ligands CD80 and CD86. Flow cytometry analysis of a competition experiment of F023700912 (filled circles) and ipilimumab (filled squares) with fixed concentrations (10× EC30) of (A) hCD80-hFc or (B) hCD86-hFc on hCTLA4-overexpressing CHO-K1 cells. The ligands were detected via the human IgG Fc fusion protein. The data generated in these experiments are set forth in FIG. 6 (A-B). These results demonstrate the ability of F023700912 to block binding of CTLA-4 to its ligands CD80 and CD86, illustrating the ability of F023700912 to affect immune responses modulated by CTLA-4 and its interactions with CD80 and CD86.

Figure 6A:
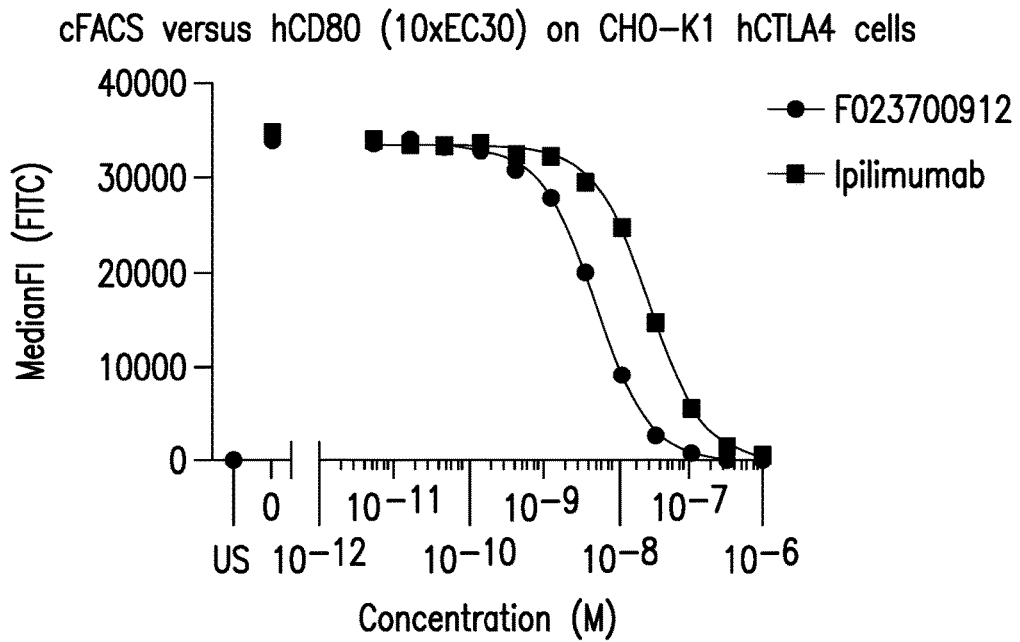
FIG. 6 (A-B). Competition between Nanobody F023700912 or ipilimumab and (A) CD80 or (B) CD86 for binding to human CTLA4 expressed on CHO-K1 cells.
Figure 6B:
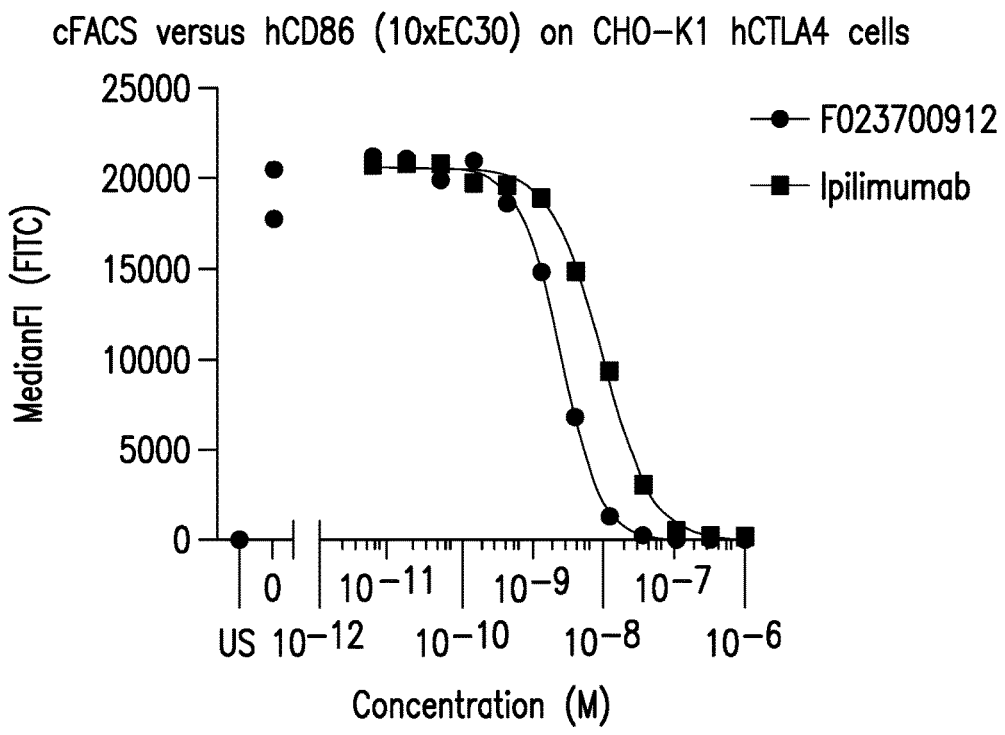
Figure 7A:
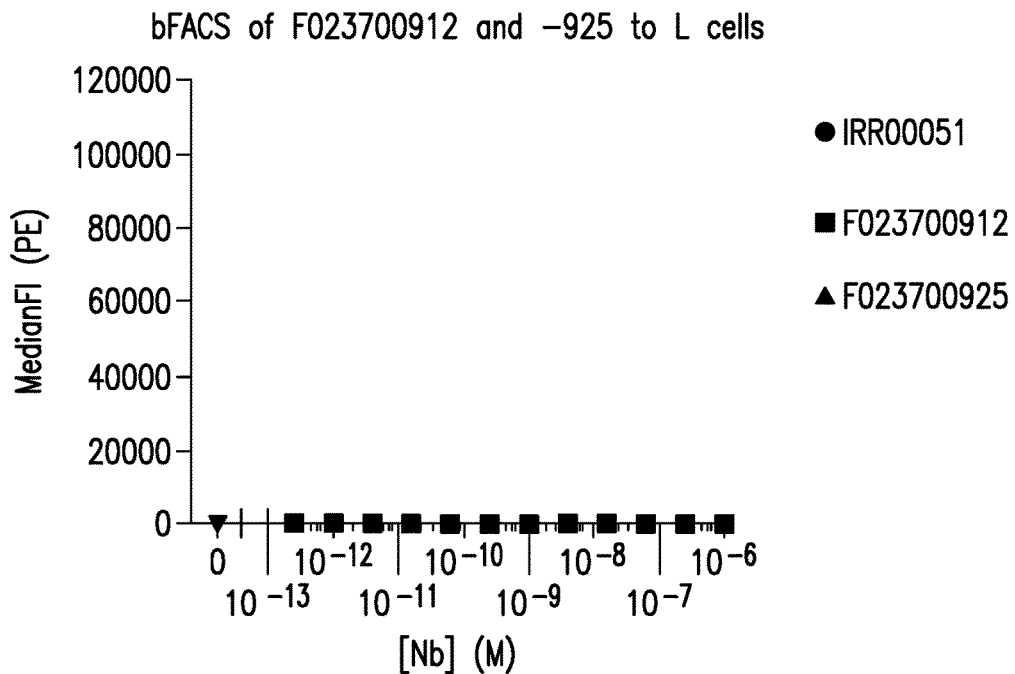
FIG. 7 (A-H). Specificity assessment of Nanobody F023700912, F023700925 or control nanobody (IRR00051) for binding to BTLA, CD8, PD1, CTLA4, LAG3, CD28 or control cells. Binding of the Nanobodies was determined to (A) negative control L cells, (B) negative control CHO-K1 cells, (C) huCD28+L cells, (D) huCD8alpha+L cells, (E) huLag-3+CHO-K1 cells, (F) huBTLA+CHO-K1 cells, (G) huCTLA-4+CHO-K cells, and (H) huPD-1+CHO-K1 cells.
Figure 7B:
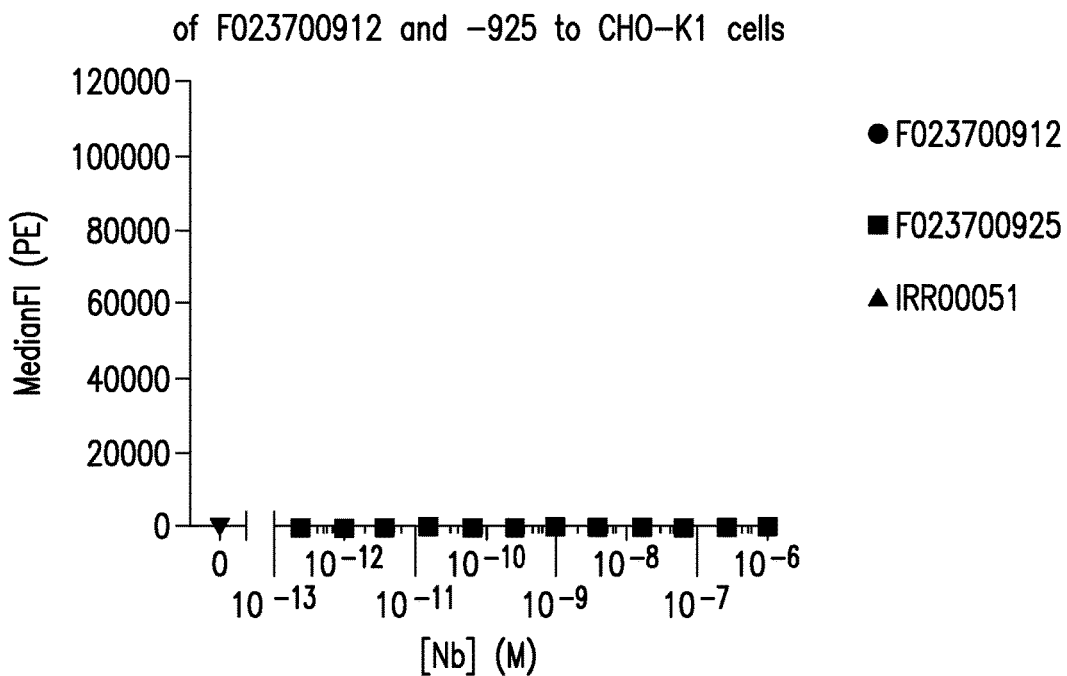
Figure 7C:
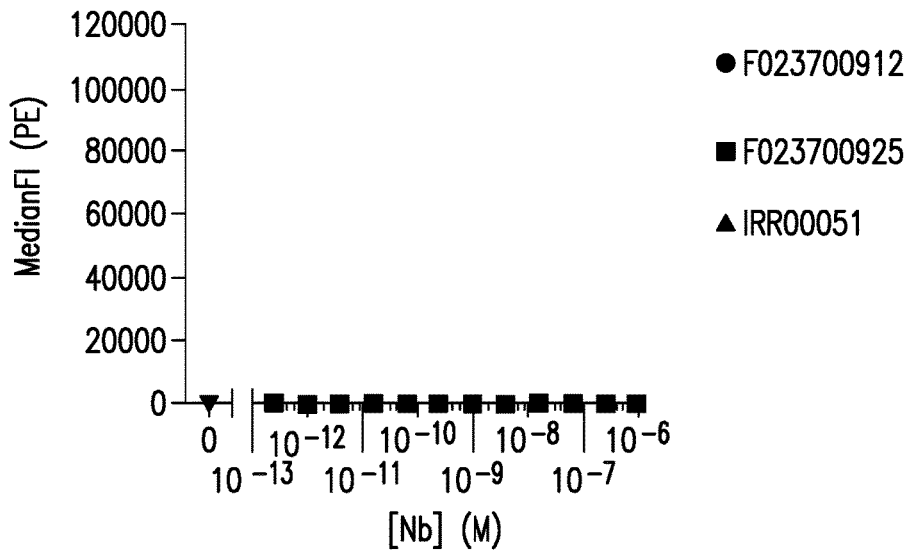
Figure 7D:
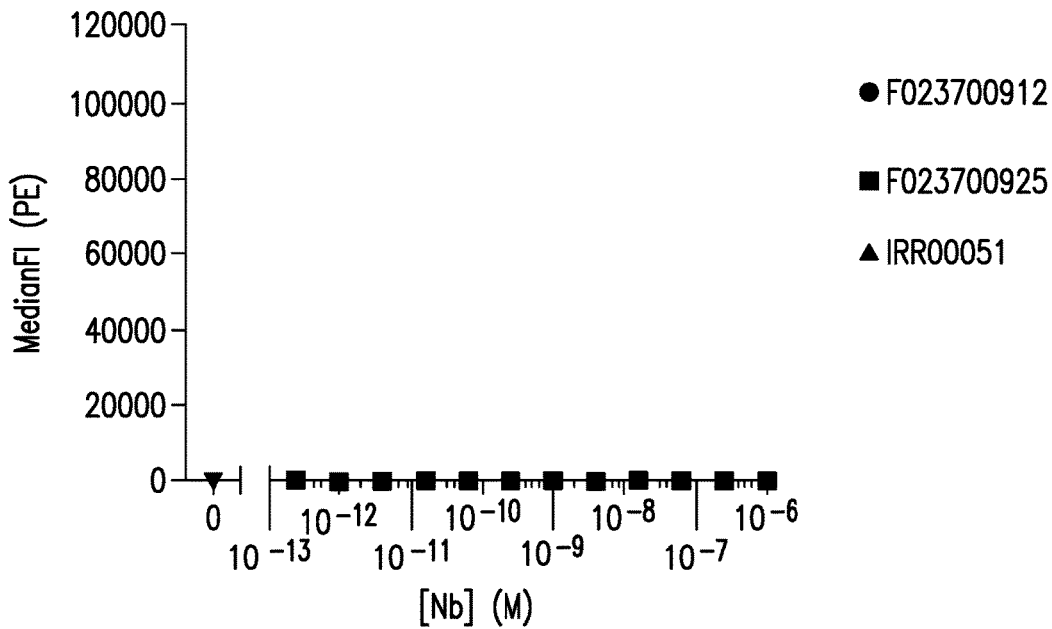
Figure 7E:
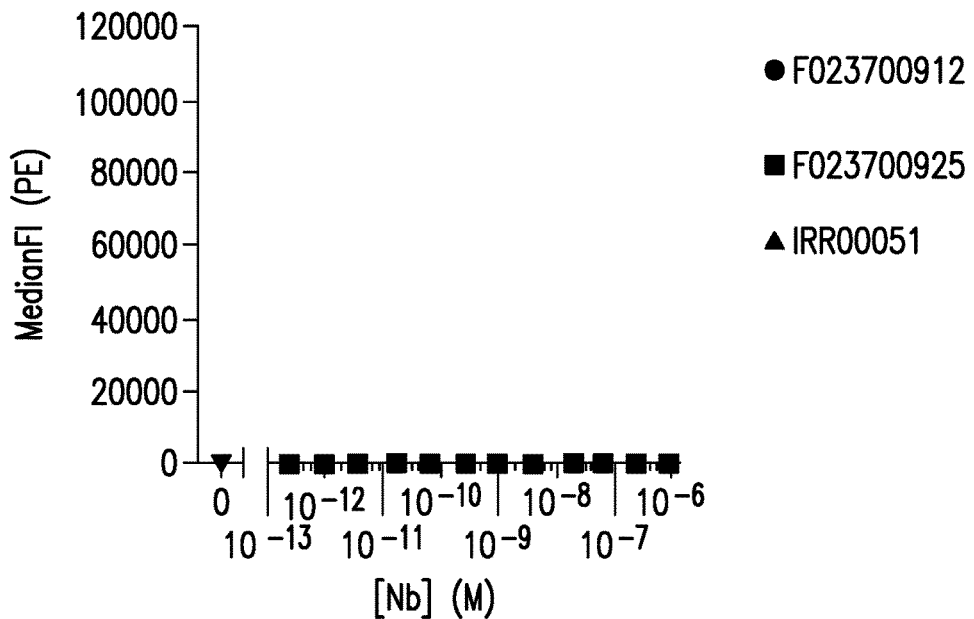
Figure 7F:
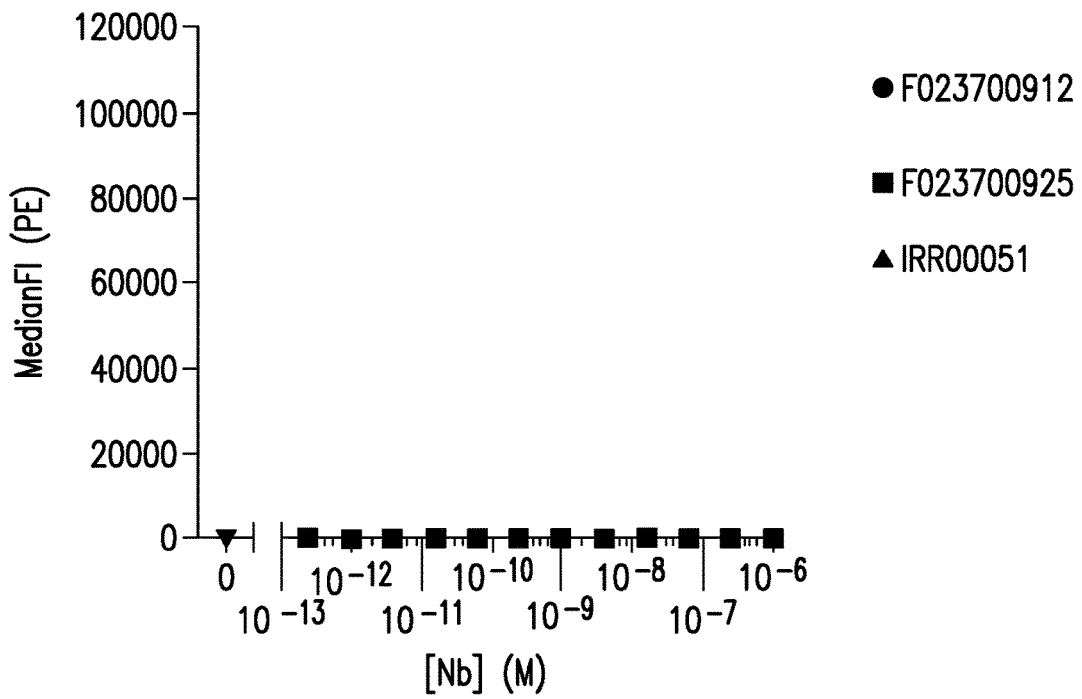
Figure 7G:
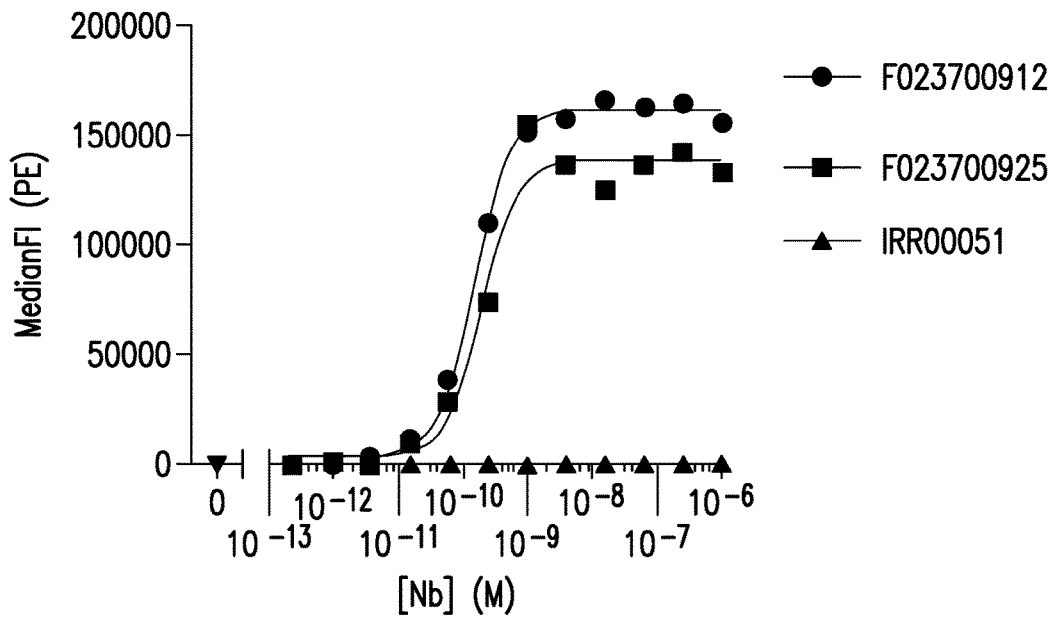
Figure 7H:
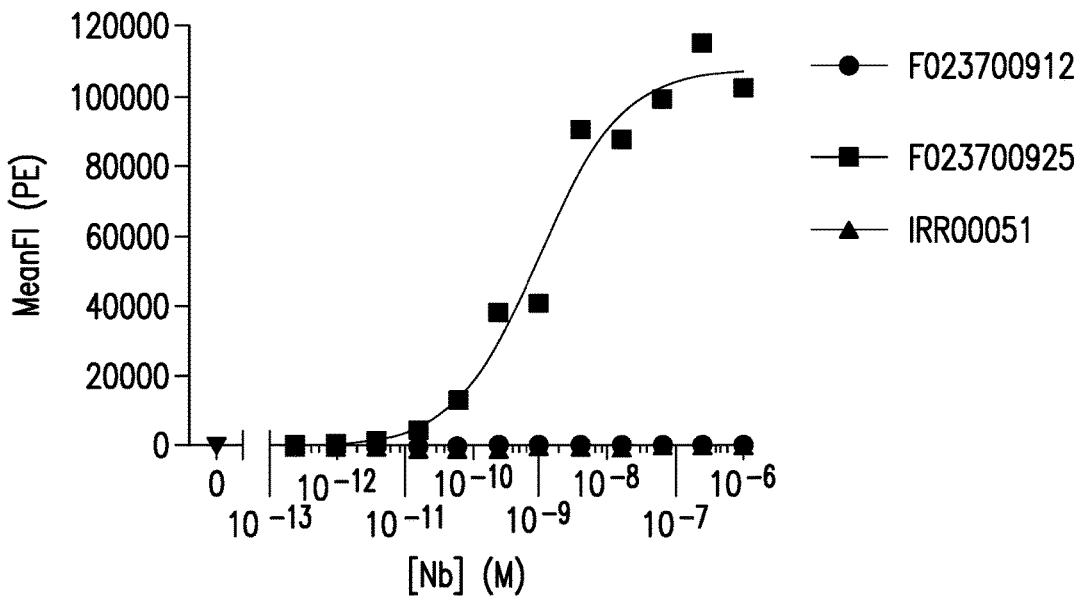

FIG. 6 (A-B) is a dilution series (start concentration 1/3 serial dilution, 12 pts) of Nb F023700912 (filled circles) and Ipilimumab (filled squares) in 100 µl FACS buffer (PBS (Life Technologies, 14190-094), 10% heat-inactivated foetal bovine serum (Sigma, F7524), 0.05% $NaN_3$ (ThermoScientific, 19038)) were added to 1E5 human CTLA4-overexpressing CHO-K1 cells/well in the presence of a fixed concentration of (A) FITC-labelled human CD80-hFc-HIS6 or (B) FITC-labelled human CD86-hFc-HIS6 (FITC labelling was performed with a degree of labelling of 3.6 and 2 respectively; concentration=10× EC30, being 3.71E-08 M or 4.35E-08 M respectively) and incubated for 90 minutes at 4° C.

After three washing steps (1 washing step=removal of Nb dilutions, addition of 100 µl cold FACS buffer, centrifugation for 5 minutes at 250 g), the cells were resuspended in 50 µl cold FACS buffer supplemented with 5 nM TO-PRO-3 (Molecular Probes, T3605) and analyzed with a FACS Canto.

First, a P1 population is selected based on FSC-SSC distribution. Stopping gate was set on 10000 cells in P1. From this population the TO-PRO-3+cells (dead cells) are excluded. For this P1/TO-PRO-3-negative population the median FITC value is calculated.

Example 4: F023700912 Specificity Assessment

Specificity assessment F023700912 demonstrated selective binding to CTLA-4. Specificity assessment against BTLA, CD8, PD1, CTLA4, LAG3, CD28 was performed on overexpressing cells using flow cytometry, whereas ICOS binding was evaluated in ELISA as a recombinant protein (hICOS-hFc). Expression of BTLA, CD8, PD1, CTLA4, LAG3, CD28 was confirmed via directly-labelled target-specific Abs. Anti-hICOS and anti-hCTLA4/anti-hPD1 positive controls were all positive. No binding to hICOS was observed in the ELISA assays. FIG. 7(A-H) assesses binding to negative control L cells, negative control CHO-K1 cells, huCD28+L cells, huCD8alpha+L cells, huLag-3+CHO-K1 cells, huBTLA+CHO-K1 cells, huCTLA-4+CHO-K cells, and huPD-1+CHO-K1 cells, respectively. No binding to BTLA, CD8, PD1, LAG3, CD28 could be observed for F023700912, whereas potent binding of F023700912 was observed on CTLA-4+CHO-K1 cells. The data generated in these experiments are set forth in FIG. 7 (A-H). These results illustrated selective binding of F023700912 to CTLA-4 predicting minimal off-target effects upon in vivo administration.

FIG. 7 (A-H) is a dilution series (start concentration 1/4 serial dilution, 12 pts) of batches of half-life extended (ALB0011 building block) Nbs F023700912 (filled circles), F023700925 (filled squares) and negative control Nb IRR00051 (filled triangles) in 200 µl FACS buffer (PBS (Life Technologies, 14190-094), 10% heat-inactivated foetal bovine serum (Sigma, F7524), 0.05% $NaN_3$ (ThermoScientific, 19038)) were added to (A) 2E4 L-cells/well, (B) 2E4 CHO-K1 cells/well, (C) human CD28-overexpressing L-cells or (D) human CD8 alpha-overexpressing L-cells, (E) 2E4 human LAG3-overexpressing CHO-K1/well, (F) 2E4 human BTLA-overexpressing CHO-K1 cells/well, (G) human CTLA4-overexpressing CHO-K1 cells/well or (H) human PD1-overexpressing CHO-K1 cells/well and incubated for 30 minutes at 4° C.

After three washing steps (1 washing step=removal of Nb dilutions, addition of 100 µl cold FACS buffer, centrifugation for 5 minutes at 250 g), the cells were incubated for 30 minutes at 4° C. with 3 µg/ml anti-ALB0011 mouse mAb ABH00074 in cold FACS buffer for detection of the half-life-extended Nbs.

After three washing steps, the cells were incubated for 30 minutes at 4° C. with a 1/100 dilution in cold FACS buffer of PE goat F(ab')$_2$ anti-mouse IgG (Jackson ImmunoResearch, 115-116-071).

After three washing steps, the cells were resuspended in 50 µl cold FACS buffer supplemented with 5 nM TO-PRO-3 (Molecular Probes, T3605) and analyzed with a FACS Canto.

First, a P1 population is selected based on FSC-SSC distribution. Stopping gate was set on 10000 cells in P1. From this population the TO-PRO-3+cells (dead cells) are excluded. For this P1/TO-PRO-3-negative population the median PE value is calculated.

Example 5: F023700912 Nanobody Binding to Human, Rhesus Monkey and Mouse Albumin F023700912 binds to human, rhesus monkey and mouse albumin, predicting prolonged half-life when compared to non-albumin-binding Nanobodies. Binding to human, rhesus monkey and mouse serum albumin was observed, when analyzed using surface plasmin resonance (SPR). The data are set forth below in Table E. Albumin binding of F023700912 is expected to reduce the clearance of the Nanobody upon in vivo administration improving its therapeutic potential.

TABLE E

Binding of Nanobody to Albumin.

| | Human serum albumin | | | Rhesus serum albumin | | | Mouse serum albumin | | |
|---|---|---|---|---|---|---|---|---|---|
| | Ka (1/Ms) | Kd (1/s) | KD (M) | Ka (1/Ms) | Kd (1/s) | KD (M) | Ka (1/Ms) | Kd (1/s) | KD (M) |
| F023700912 | 9.4E+04 | 8.8E−03 | 9.3E−08 | 9.5E+04 | 8.9E−03 | 9.3E−08 | 1.2E+05 | 1.8E−01 | 1.5E−06 |
| F023700925 | 3.4E+04 | 7.6E−03 | 2.2E−07 | 3.3E+04 | 8.1E−03 | 2.4E−07 | 4.8E+04 | 1.5E−01 | 3.1E−06 |

Instrument: Biacore T100 (GE Healthcare);
Sensor chip: CM5 (ID T160713-2, GE Healthcare, lot 10242599)

Example 6: Nanobody F023700906 N73 Variants

Figure 8A:
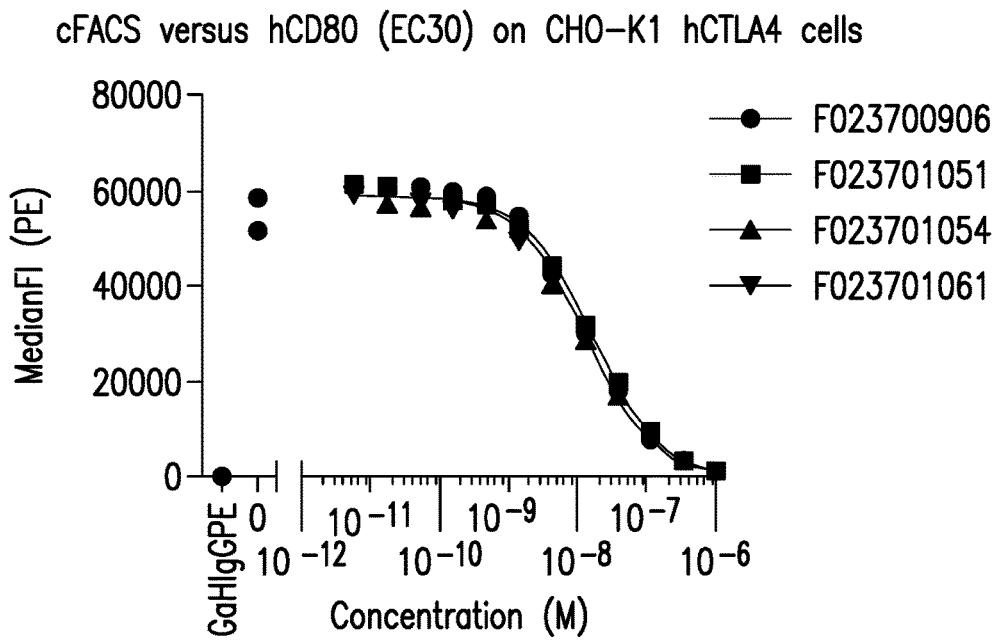
FIG. 8 (A-B). Competition between Nanobody F023700906, F023701051, F02371054 or F023701061 and (A) human CD80 or (B) human CD86 for binding to human CTLA-4 expressed on CHO-K1 cells.
Figure 8B:
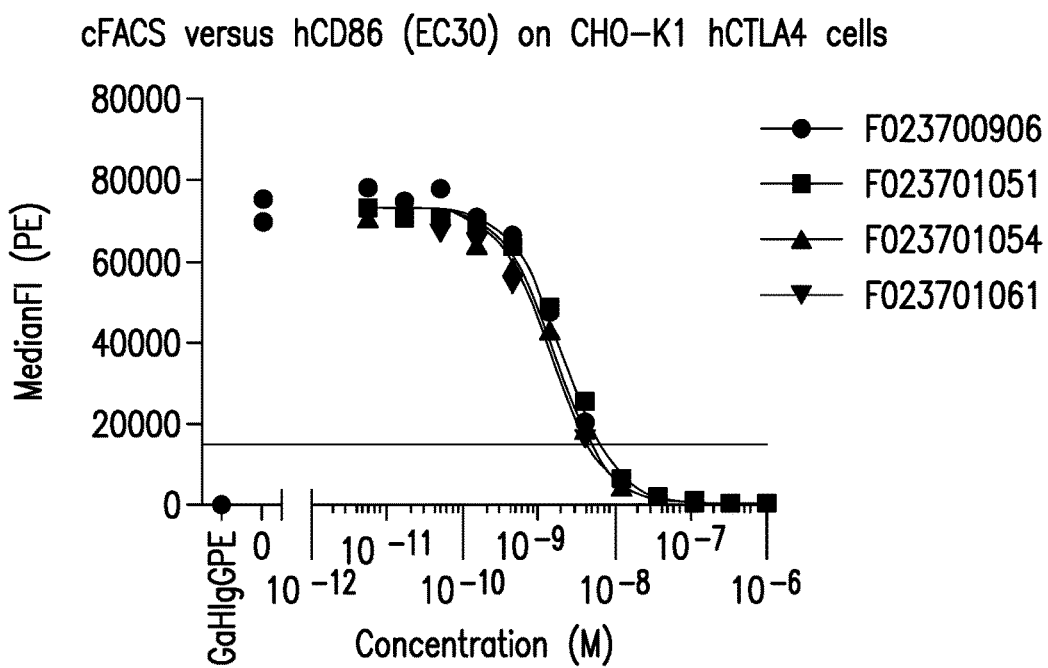
Figure 9C:
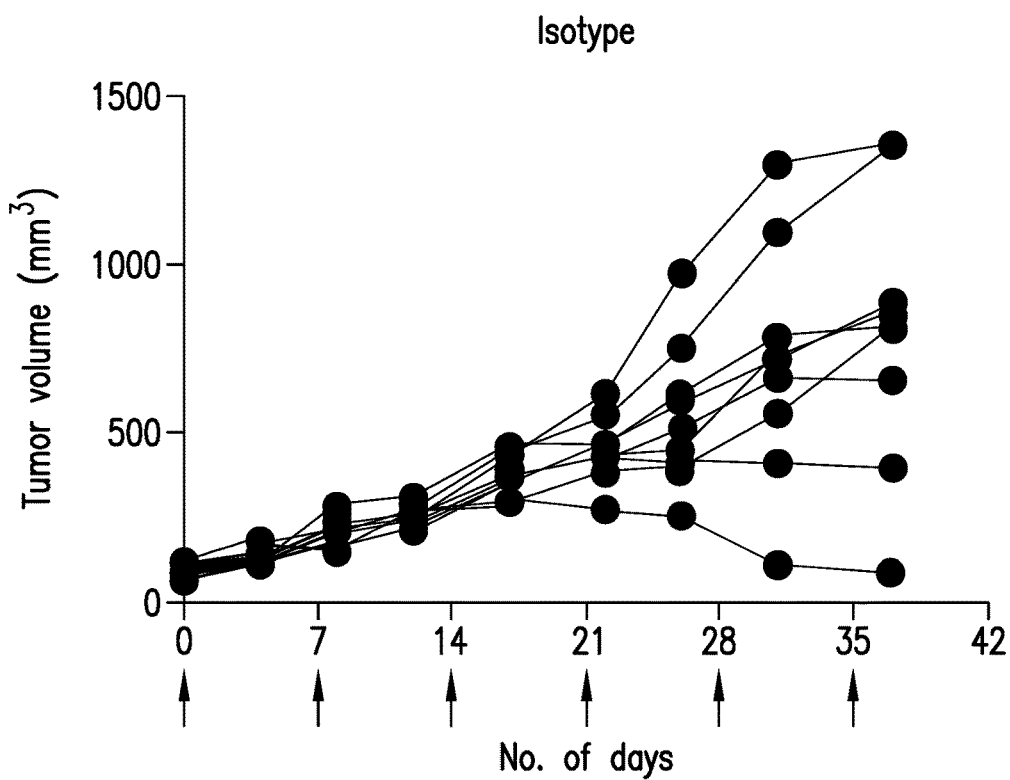
FIG. 9 (A-S). Nanobody effect on panc 08.13 tumors in humanized mice. (A) average tumor volumes ±SEM and (B) individual tumor volumes on day-37 in mice treated with isotype control, ipilimumab (N297A), ipilimumab, pembrolizumab, ipilimumab+pembrolizumab, F023700912 at 5 mpk dosage (CTLA4 Nab-5), F023700912 at 15 mpk dosage (CTLA4 Nab-15), or pembrolizumab+CTLA4 Nab-15; and tumor volumes in individual mice over the course of the experiment in mice treated with (C) isotype control antibody, (D) ipilimumab (N297A), (E) ipilimuamb, (F) pembrolizumab, (G) ipilimumab+pembrolizumab, (H) CTLA4 Nab-5, (I) CTLA4 Nab-15 or (J) CTLA4 Nab-15+pembrolizumab; (K-S) average (mean±SEM) and individual body weight changes in each treatment group.
Figure 9D:
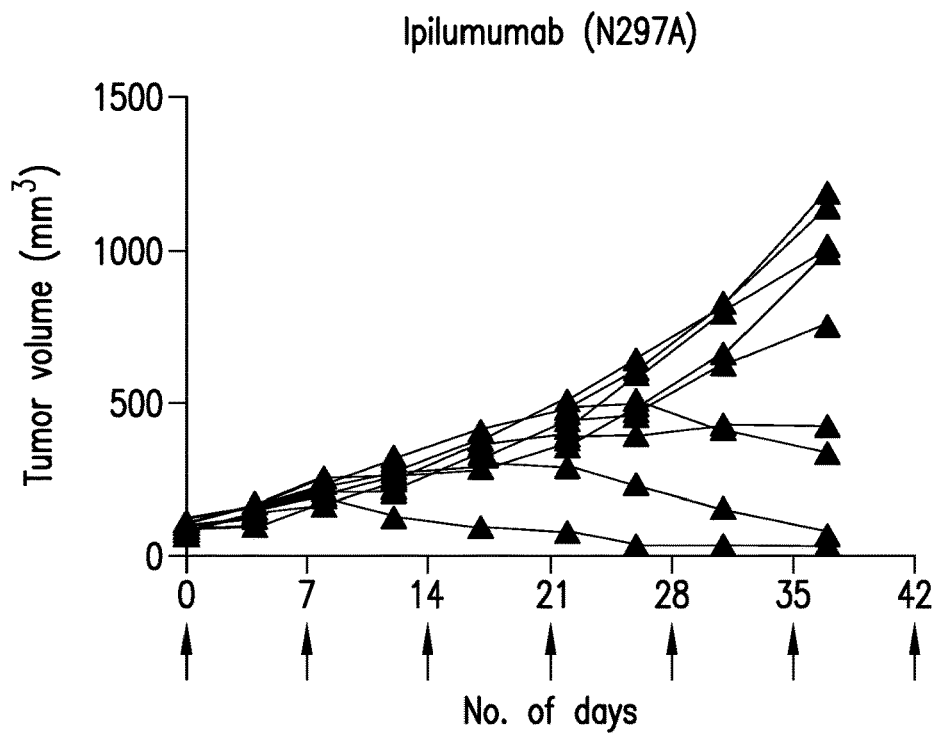
Figure 9E:
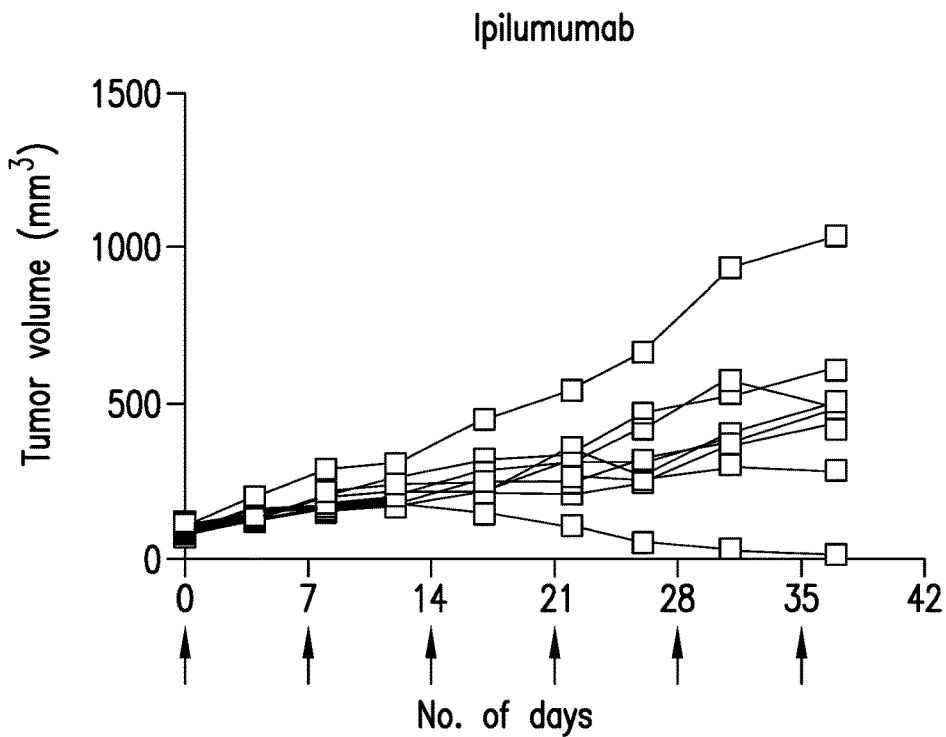
Figure 9F:
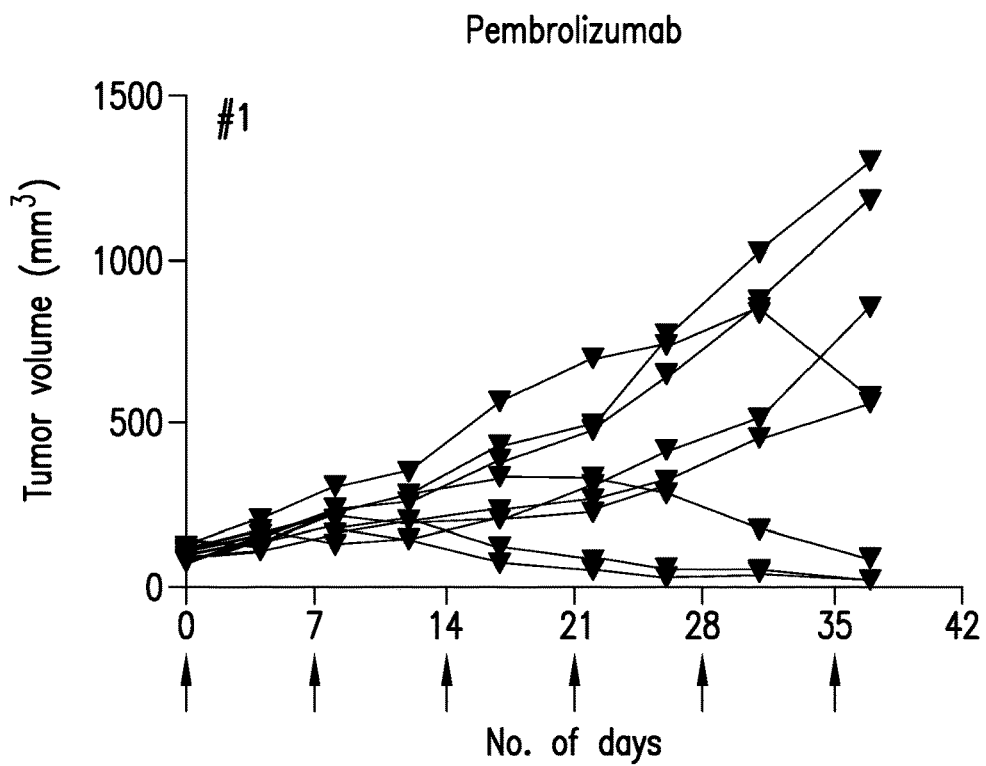
Figure 9G:
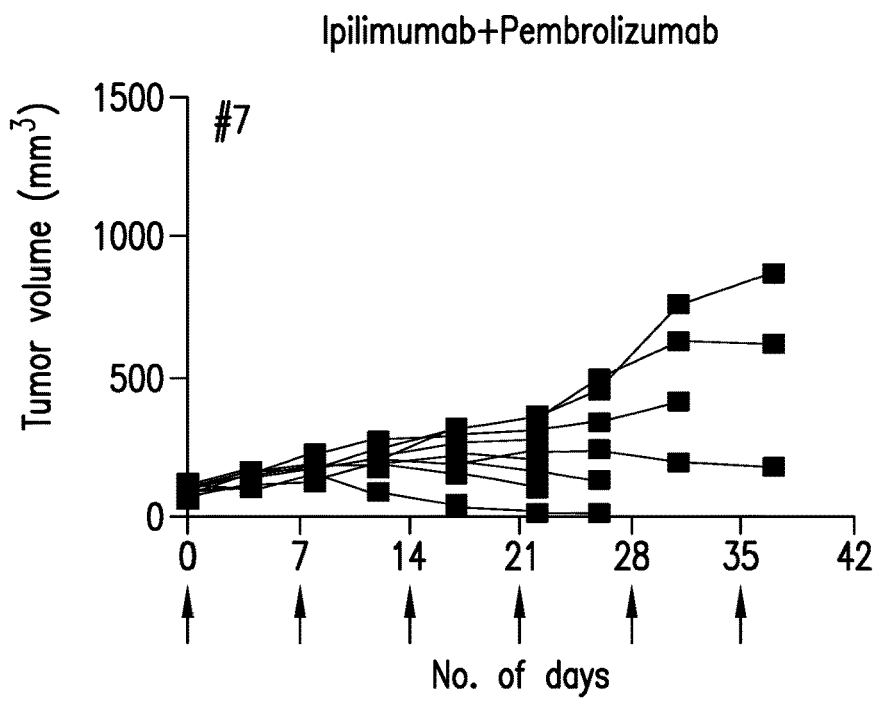
Figure 9H:
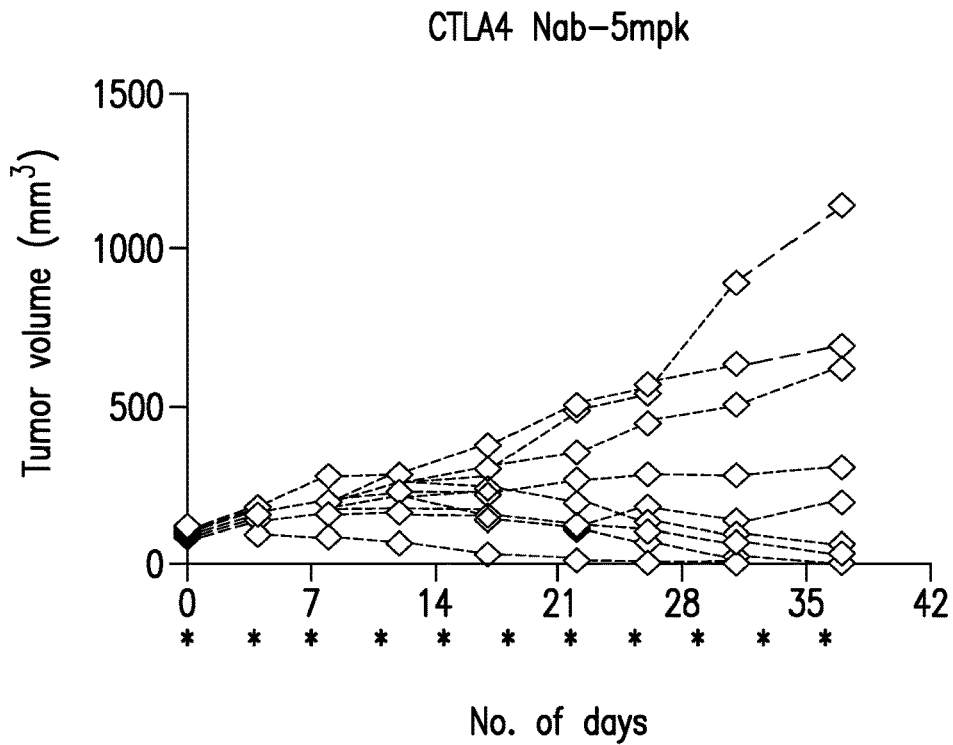
Figure 9I:
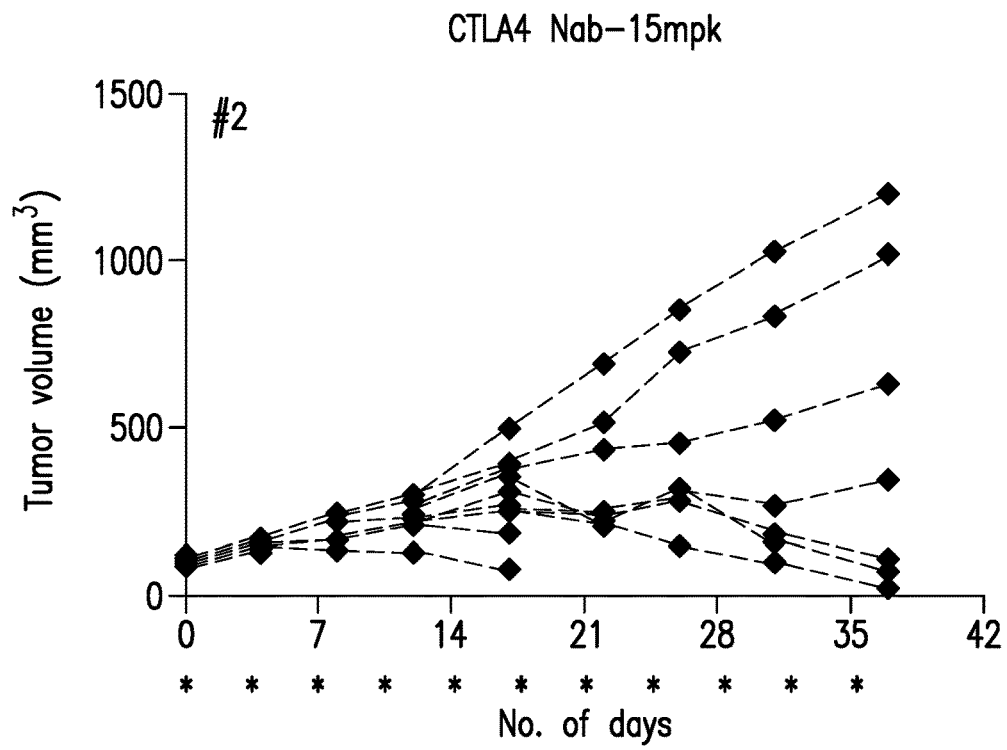
Figure 9J:
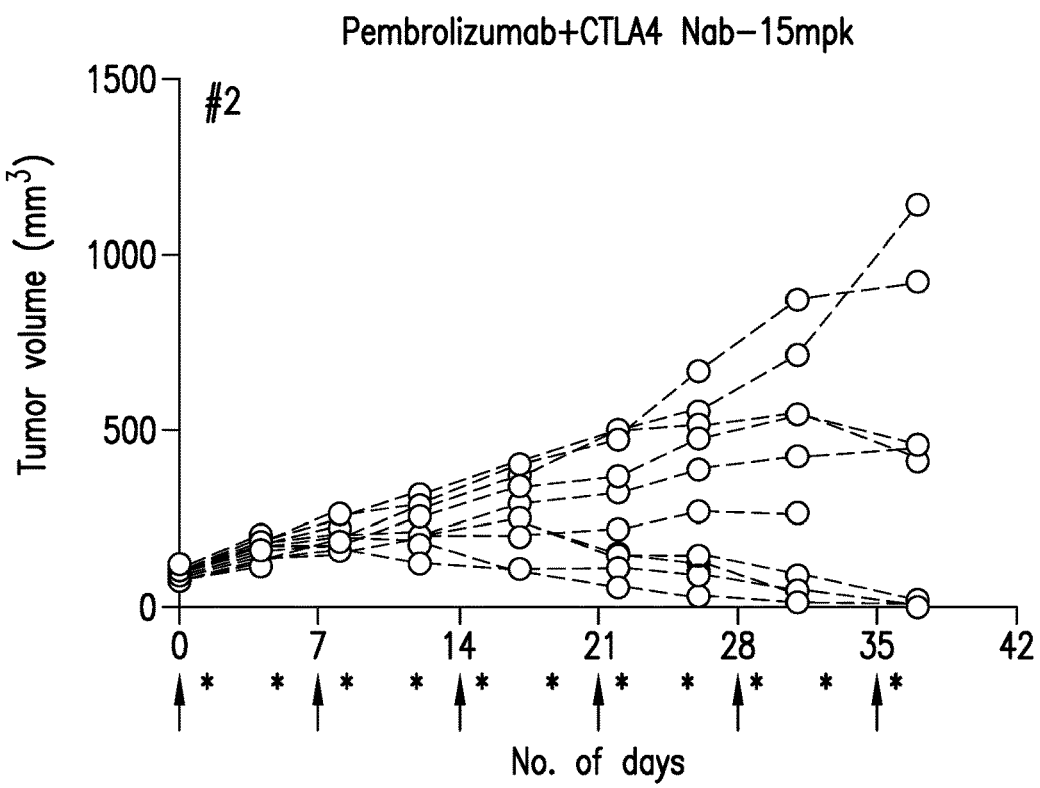
Figure 9K:
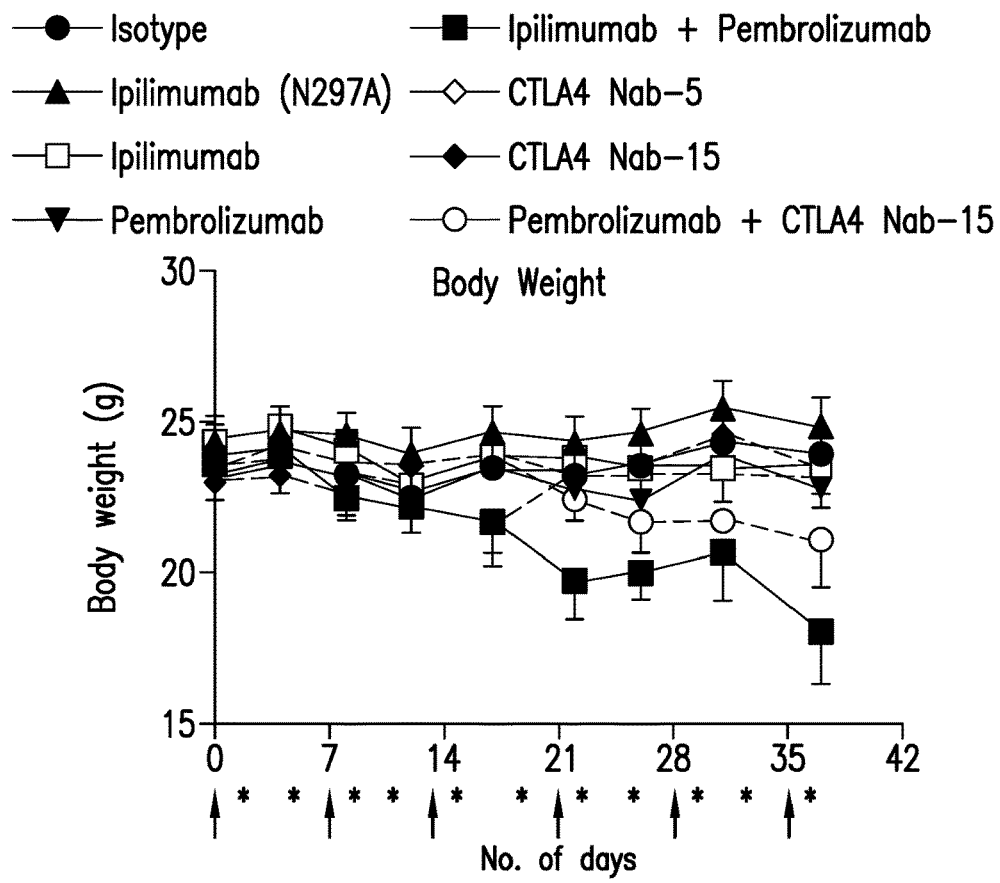
Figure 9L:
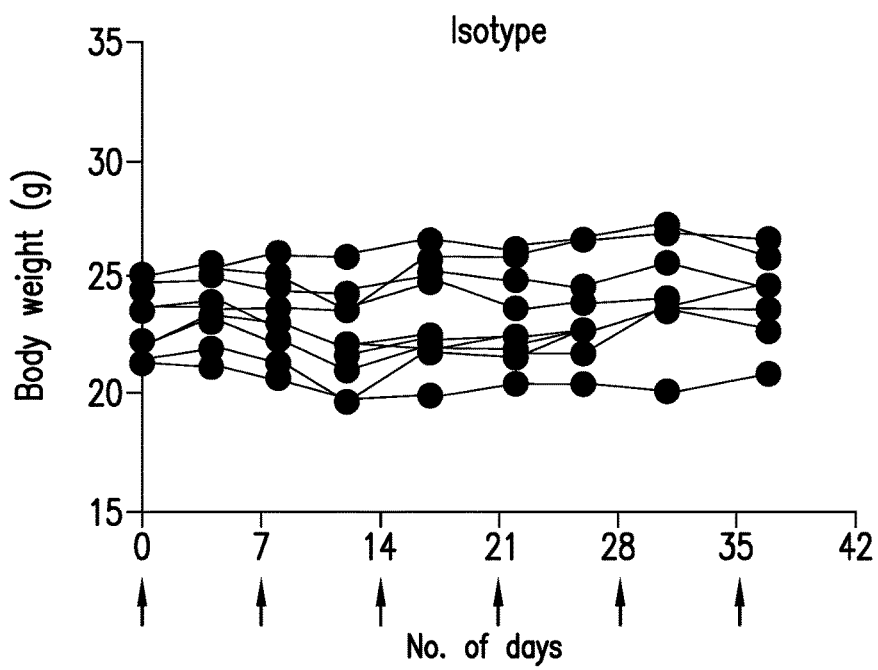
Figure 9M:
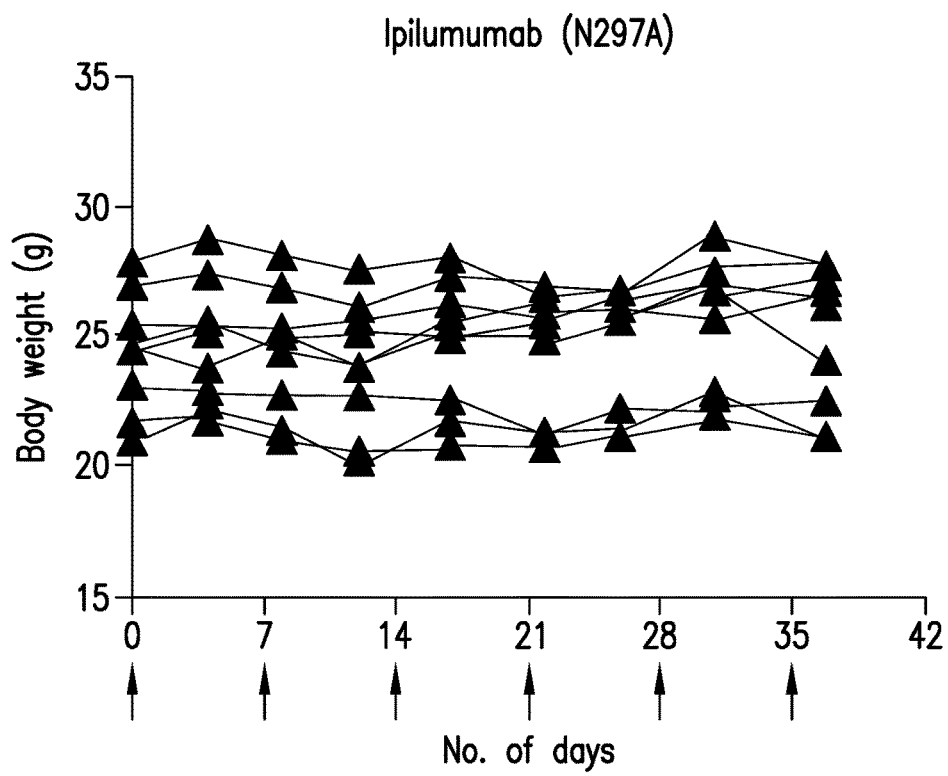
Figure 9N:
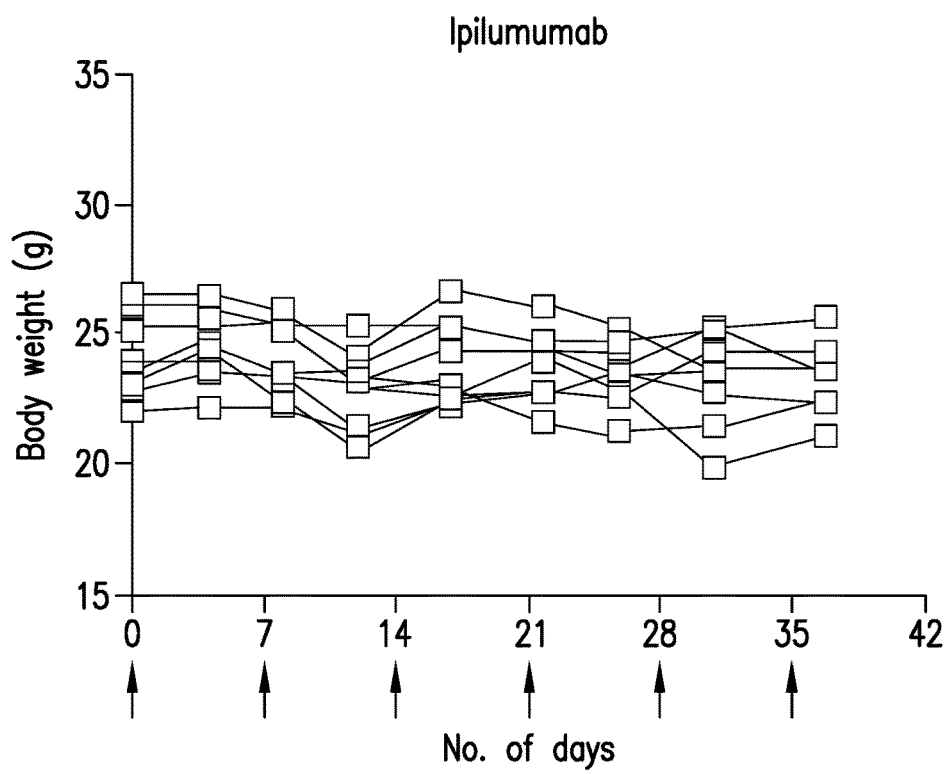
Figure 9O:
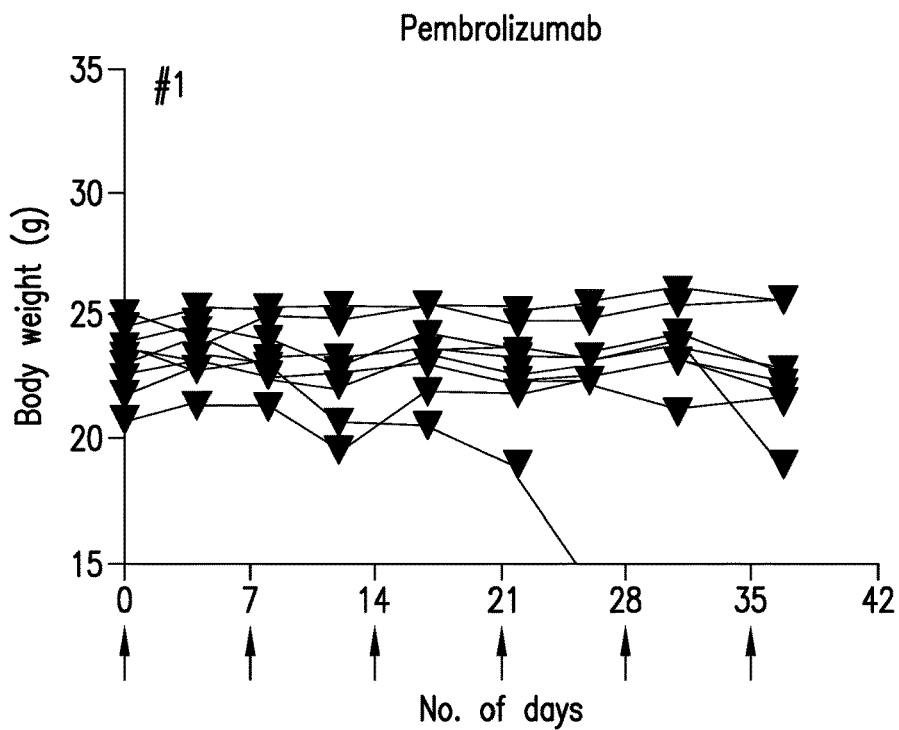
Figure 9P:
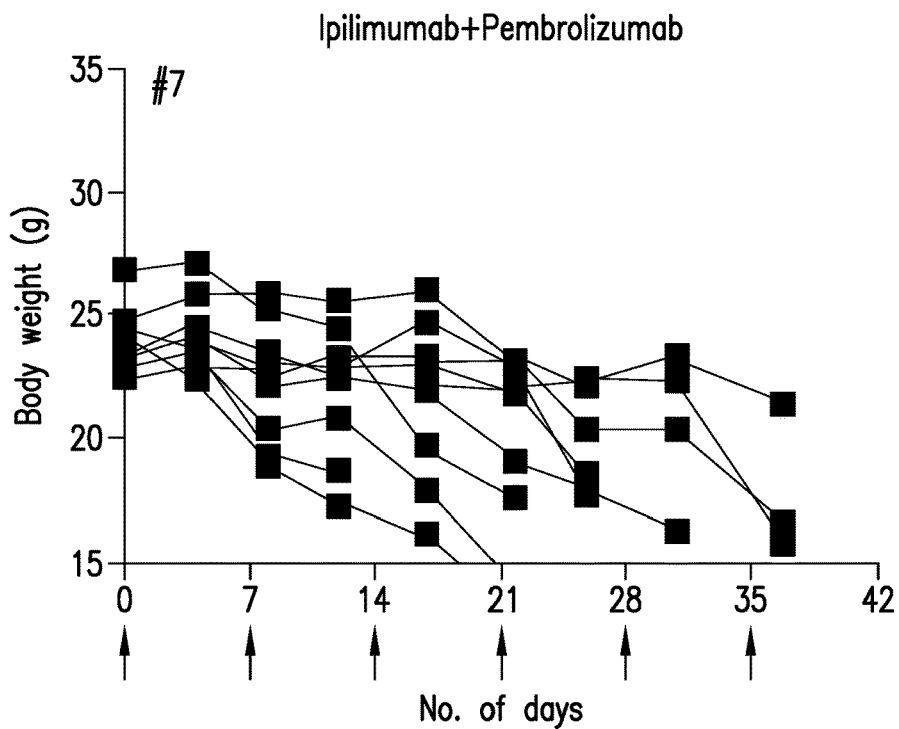
Figure 9Q:
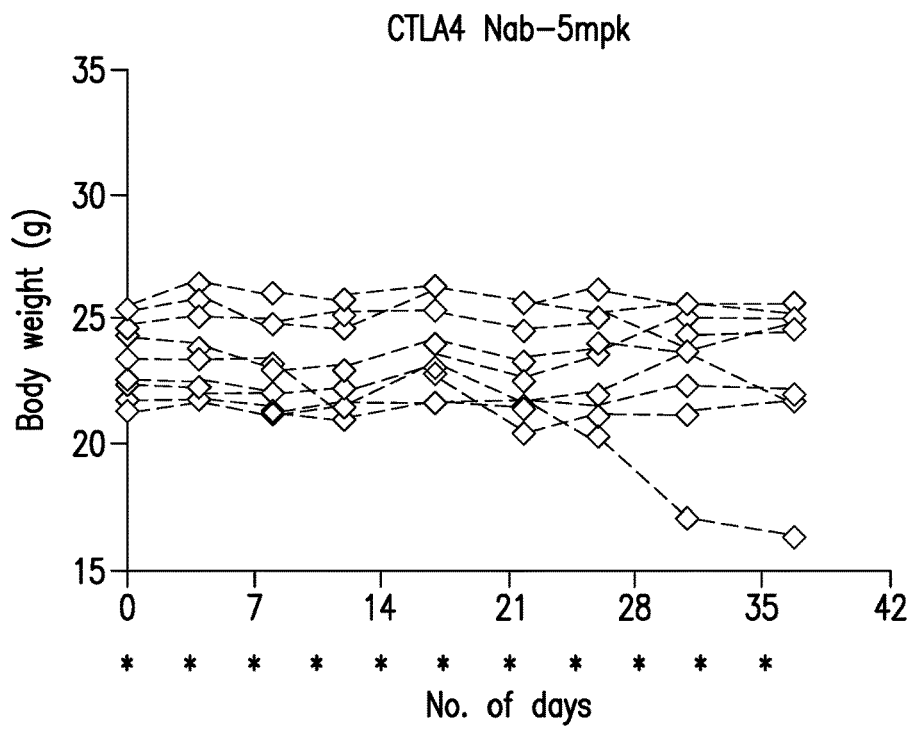
Figure 9R:
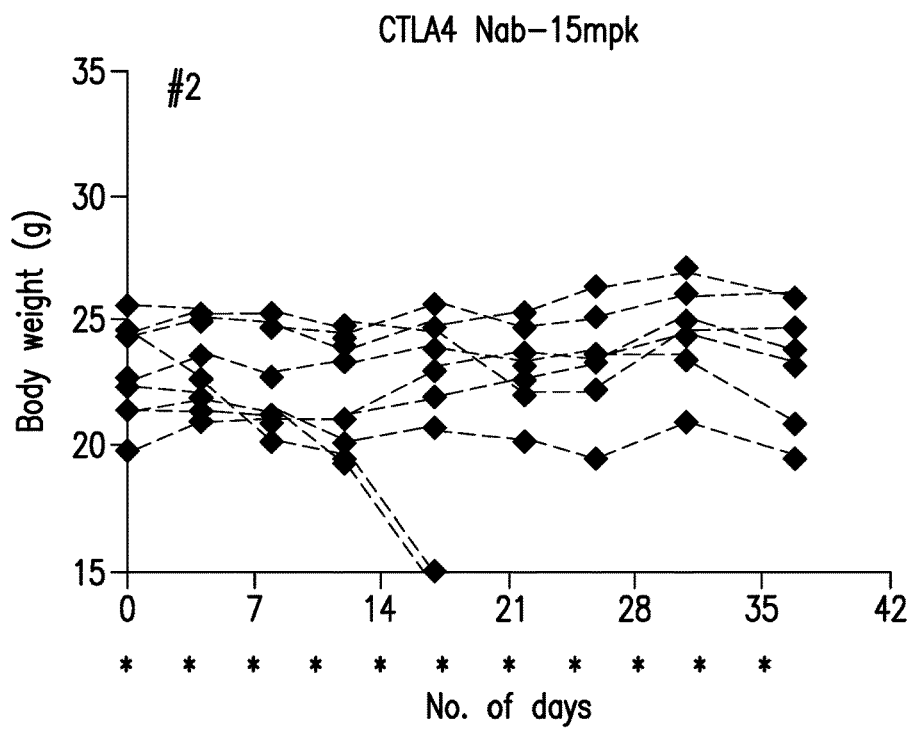
Figure 9S:
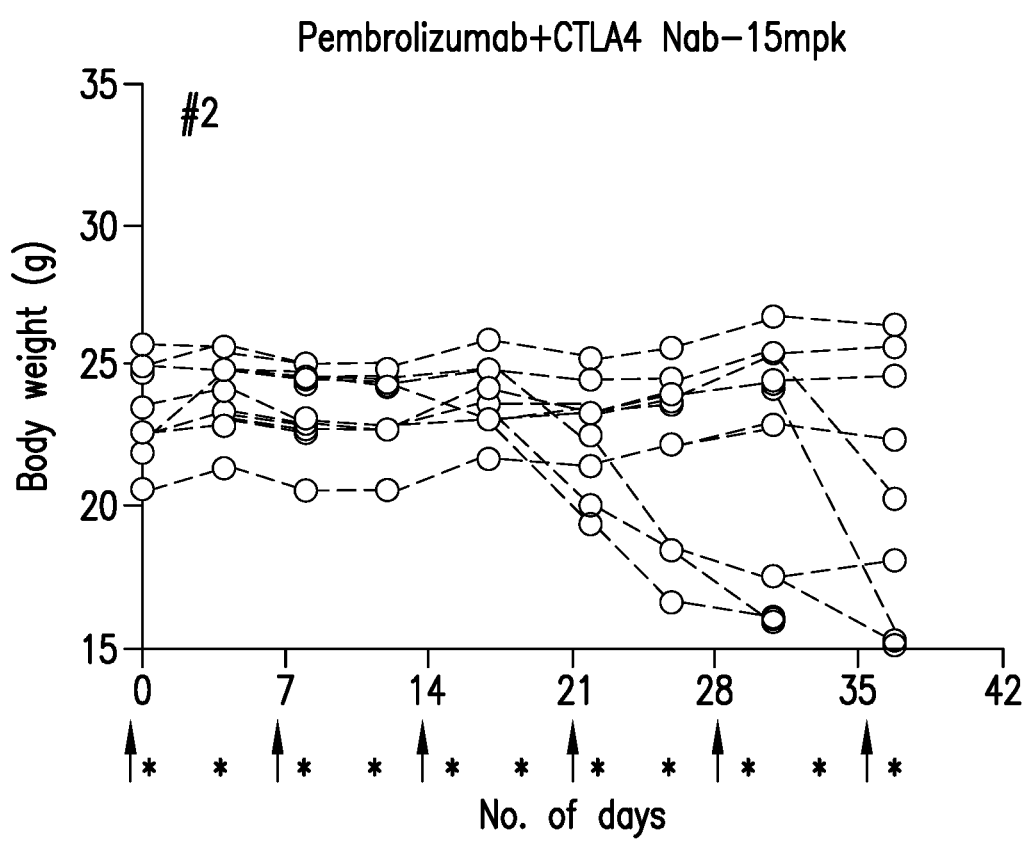

Variants F023701051 (11F01(L11V,A14P,Q45R,N73Q, A74S,K83R,V89L, M96P,Q108L)-FLAG3-HIS6), F023701054 (11F01(L11V,A14P,Q45R,N73T,A74S,K83R, V89L, M96P,Q108L)-FLAG3-HIS6), and F023701061 (11F01 (L11V,A14P,Q45R,N73Y, A74S,K83R,V89L,M96P,Q108L)-FLAG3-HIS6) were compared to F023700906 for their ability to block binding of (A) CD80 or (B) CD86 to CTLA-4 expressing CHO-K1 cells. All these variants were able to block binding of CD80 and CD84 to CTLA-4. Blocking of CTLA4 to CD80 and CD86 was determined for several of the variants. These blocking data are set forth in FIG. 8 (A-B). These results illustrate the feasibility of varying the amino acid in position N73 without major impact on the ability of the Nanobodies to block binding of CD80 or CD86 to CTLA-4. Such variants will allow for avoidance of deamidation at N73.

Example 7: F023700912 Eradicates Established Solid Tumors in Humanized Mice

Humanized mice (Jackson Laboratories) were implanted with Panc 08.13 tumor cells (human pancreatic adenocarcinoma). Mice with established tumors (~100 mm$^3$, n=9-10/group) were treated as follows: 1-Isotype controls (hIgG1-2 mg/kg and hIgG4-3 mg/kg); 2-Ipilimumab-N297A (3 mg/kg); 3-Ipilimumab (3 mg/kg); 4-Pembrolizumab (2 mg/kg); 5-Ipilimumab (3 mg/kg)+Pembrolizumab (2 mg/kg); 6-F023700912 (5 mg/kg; indicated as CTLA4-Nab 5), 7-F023700912 (15 mg/kg; indicated as CTLA4-Nab-15), and 8-F023700912 (15 mg/kg)+Pembrolizumab (2 mg/kg). All the antibodies were injected subcutaneously every 7 days for 6 doses. F023700912 was administered subcutaneously every 3.5 days for 11 doses. Tumor volume and body weight were measured every 4-5 days. Shown in FIG. 9 (A-B) are average tumor volumes ±SEM, individual tumor volumes on day-37, and tumor volumes in individual mice over the course of the experiment. The tumor volume for each treatment group is also shown in FIG. 9 (C-J). Average (mean±SEM) and individual body weight changes in each treatment group were also measured (FIG. 9 (k-s)). The number of mice that were found dead or humanely euthanized due to body weight loss was indicated as '#' indicated antibody and '*' indicated Nanobody dosing schedule. These data illustrated the ability of F023700912 to induce anti-human tumor reponse in vivo in animals that harbor human immune cells. These data support the potential of F023700912 in the treatment of human cancer.

Example 8: Binding of F023700912 and F023700925 to Pre-Existing Antibodies from Healthy Subjects and Cancer Patients Trivalent reference Nanobody, 013700112 (not modified for reducing the binding of pre-existing antibodies) demonstrates binding to several serum samples derived from (FIG. 10A) healthy subjects or (FIG. 10B) cancer patients. Sequence optimized trivalent Nanobody of similar size, F023700912, demonstrates a lower frequency of binding to the same serum samples. F023700925 comprises the same building blocks as F023700912. Despite the larger size, the pentavalent F023700925 Nanobody exhibits no more binding to pre-existing Abs than the reference Nanobody 013700112. Binding of pre-existing antibodies to Nanobodies captured on human serum albumin (HSA) was evaluated using the ProteOn XPR36 (Bio-Rad Laboratories, Inc.). PBS/Tween (phosphate buffered saline, pH7.4, 0.005% Tween20) was used as running buffer and the experiments were performed at 25° C. The ligand lanes of a ProteOn GLC Sensor Chip were activated with EDC/NHS (flow rate 30 µl/min) and HSA was injected at 10 µg/ml in ProteOn Acetate buffer pH4.5 (flow rate 100 µl/min) to render immobilization levels of approximately 3600 RU. After immobilization, surfaces were deactivated with ethanolamine HCl (flow rate 30 µl/min). Nanobodies were injected for 2 minutes at 45 µl/min over the HSA surface to render a Nanobody capture level of approximately 600 RU for trivalent F023700912 and approximately 1000 RU for pentavalent F023700925. The samples containing pre-existing antibodies were diluted 1:10 in PBS-Tween20 (0.005%) before being injected for 2 minutes at 45 µl/min followed by a subsequent 400 seconds dissociation step. After each cycle (i.e., before a new Nanobody capture and blood sample injection step) the HSA surfaces were regenerated with a 2 minute injection of HCl (100 mM) at 45 µl/min. Sensorgram processing and data analysis was performed with ProteOn Manager 3.1.0 (Bio-Rad Laboratories, Inc.). Sensorgrams showing pre-existing antibody binding were obtained after double referencing by subtracting 1) Nanobody-HSA dissociation and 2) non-specific binding to reference ligand lane containing HSA only. Binding levels of pre-existing antibodies were determined by setting report points at 125 seconds (5 seconds after end of association). As a reference, the samples containing pre-existing antibodies were also tested for binding to a trivalent Nanobody not modified for reducing the binding of these pre-existing antibodies (T013700112).

Example 9: Epitope Mapping of Anti-hCTLA4 Nanobody by Hydrogen Deuterium Exchange Mass Spectrometry Contact areas between anti-hCTLA4 nanobody, F023700912 were determined by use of hydrogen deuterium exchange mass spectrometry (HDX-MS) analysis. HDX-MS measures the incorporation of deuterium into the amide backbone of the protein and changes in this incorporation are influenced by the hydrogen's solvent exposure. A comparison of the deuterium exchange levels in antigen-alone samples and nanobody-bound samples was done to identify antigen regions that may be in contact with the nanobody.

The human CTLA4 residues most strongly protected from deuteration by the nanobody, F023700912 were VRVTVL (SEQ ID NO: 118; amino acids 33-38 of SEQ ID NO: 110), ADSQVTEVC (SEQ ID NO: 119; amino acids 41-49 of SEQ ID NO: 110) and CKVELMYPPPYYLG (SEQ ID NO:120; amino acids 93-106 of SEQ ID NO: 110). A heat map for demonstrating F023700912 binding to CTLA4 is set forth in FIG. 13.

TABLE F

| | Amino Acid Sequences (SEQ ID NO: 110) |
|---|---|
| Human CTLA4 | AMHVAQPAVVLASSRGIASFVCEYASPGKATEVRVTVLRQA DSQVTEVCAATYMMGNELTFLDDSICTGISSGNQVNLTIQG LRAMDTGLYICKVELMYPPPYYLGIGNGTQIYVIDPEPCPD SDFHHHHHHHHHGGQ |

We claim:

1. A CTLA4 binder comprising one or more immunoglobulin single variable domains (ISVDs) that bind to human CTLA4
wherein the one or more ISVDs independently comprises the amino acid sequence: XVQLVESGGGVVQPGGSLRLSCAASGGTFSFYGMG WFRQAPGKEREFVADIRTSAGRTYYADSVKGRFTISRDNSKNTVYLQMNSLRPEDTALYYCAAEPSGISGWDYWGQGTLVTVSS (SEQ ID NO: 60); and
optionally comprising a half-life extender and/or a C-terminal extender.

2. A CTLA4 binder comprising one or more immunoglobulin single variable domains (ISVDs) that bind to human CTLA4
wherein the one or more ISVDs independently comprises the amino acid sequence selected from SEQ ID NOs: 93-109; and
optionally lacking the signal sequence amino acids AAADYKDHDGDYKDHDIDYKDDDDKGAAHH-HHHH (amino acids 120-153 of each of SEQ ID Nos: 93-109) thereof.

3. The CTLA4 binder of claim 1, wherein the CTLA4 binder comprises a half-life extender.

4. The CTLA4 binder of claim 3, wherein the half-life extender is an ISVD that binds to human serum albumin.

5. The CTLA4 binder of claim 4 wherein the ISVD that binds to human serum albumin is ALB11002, which has the amino acid sequence set forth in SEQ ID NO: 66.

6. The CTLA4 binder of claim 1 comprising:
an ISVD that binds to human CTLA4 comprising the amino acid sequence set forth in SEQ ID NO: 60; a peptide linker; an ISVD that binds to human CTLA4 comprising the amino acid sequence set forth in SEQ ID NO: 60; a peptide linker; a half-life extender; and, optionally, a C-terminal extension alanine.

7. A CTLA4 binder of claim 1 comprising:
an ISVD that binds to human CTLA4 comprising the amino acid sequence set forth in SEQ ID NO: 60; a peptide linker; a half-life extender; and, optionally, a C-terminal extension alanine.

8. The CTLA4 binder of claim 6 wherein each peptide linker comprises the amino acid sequence GGGGSGGGGSGGGGSGGGGSGGGGSGGGGSGGGGS (SEQ ID NO: 65).

9. An injection device or vessel that comprises the CTLA4 binder of claim 1 and further comprising a therapeutic agent.

10. The CTLA4 binder of claim 1, wherein the CTLA4 binder comprises at least two ISVDs that bind human CTLA4.

11. A CTLA4 binder comprising one or more immunoglobulin single variable domains (ISVDs) that bind to human CTLA4 which comprises the amino acid sequence:

(SEQ ID NO: 62)
DVQLVESGGGVVQPGGSLRLSCAASGGTFSFYGMG

WFRQAPGKEREFVADIRTSAGRTYYADSVKGRFTISRDNSKNTVYLQMN

SLRPEDTALYYCAAEPSGISGWDYWGQGTLVTVSSGGGGSGGGGSGGGG

SGGGGSGGGGSGGGGSGGGGSEVQLVESGGGVVQPGGSLRLSCAASGGT

FSFYGMGWFRQAPGKEREFVADIRTSAGRTYYADSVKGRFTISRDNSKN

TVYLQMNSLRPEDTALYYCAAEPSGISGWDYWGQGTLVTVSSGGGGSGG

GGSGGGGSGGGGSGGGGSGGGGSEVQLVESGGGVVQPGNSLRLS

CAASGFTFSSFGMSWVRQAPGKGLEWVSSISGSGSDTLYADSVKGRFTI

SRDNAKTTLYLQMNSLRPEDTALYYCTIGGSLSRSSQGTLVTVSSA.

12. A pharmaceutical composition comprising the CTLA4 binder of claim 11 and a pharmaceutically acceptable carrier.

13. A pharmaceutical composition comprising the CTLA4 binder of claim 12 and a pharmaceutically acceptable carrier.

14. A CTLA4 binder consisting of SEQ ID NO: 62.

15. A CTLA4 binder comprising one or more immunoglobulin single variable domains (ISVDs) that bind to human which comprises
the amino acid sequence:

(SEQ ID NO: 64)
DVQLVESGGGVVQPGGSLRLSCAASGGTFSFYGMG

WERQAPGKEREEVADIRTSAGRTYYADSVKGRFTISRDNSKNTVYLQMN

SLRPEDTALYYCAAEPSGISGWDYWGQGTLVTVSSGGGGSGGGGSGGGG

SGGGGSGGGGSGGGGSGGGGSEVQLVESGGGVVQPGNSLRLSCAASGET

FSSFGMSWVRQAPGKGLEWVSSISGSGSDTLYADSVKGRFTISRDNAKT

TLYLQMNSLRPEDTALYYCTIGGSLSRSSQGTLVTVSSA.

* * * * *

SEQUENCE LISTING

<160> NUMBER OF SEQ ID NOS: 111

<210> SEQ ID NO 1
<211> LENGTH: 119
<212> TYPE: PRT
<213> ORGANISM: Artificial Sequence
<220> FEATURE:
<223> OTHER INFORMATION: Humanized lama

<400> SEQUENCE: 1

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Glu Met Ser Gly Ile Ser Gly Trp Asp Tyr Trp Gly Gln Gly
            100                 105                 110

Thr Gln Val Thr Val Ser Ser
        115
```

<210> SEQ ID NO 2
<211> LENGTH: 10
<212> TYPE: PRT
<213> ORGANISM: Lama

<400> SEQUENCE: 2

```
Gly Gly Thr Phe Ser Phe Tyr Gly Met Gly
1               5                   10
```

<210> SEQ ID NO 3
<211> LENGTH: 17
<212> TYPE: PRT
<213> ORGANISM: Lama

<400> SEQUENCE: 3

```
Asp Ile Arg Thr Ser Ala Gly Arg Thr Tyr Tyr Ala Asp Ser Val Lys
1               5                   10                  15

Gly
```

<210> SEQ ID NO 4
<211> LENGTH: 10
<212> TYPE: PRT
<213> ORGANISM: Lama
<220> FEATURE:
<221> NAME/KEY: MISC_FEATURE
<222> LOCATION: (2)..(2)
<223> OTHER INFORMATION: X is M or P

<400> SEQUENCE: 4

```
Glu Xaa Ser Gly Ile Ser Gly Trp Asp Tyr
1               5                   10
```

<210> SEQ ID NO 5
<211> LENGTH: 10
<212> TYPE: PRT

```
<213> ORGANISM: Lama

<400> SEQUENCE: 5

Gly Gly Thr Phe Ser Phe Tyr Gly Met Gly
1               5                   10

<210> SEQ ID NO 6
<211> LENGTH: 10
<212> TYPE: PRT
<213> ORGANISM: Lama

<400> SEQUENCE: 6

Asp Ile Arg Thr Ser Ala Gly Arg Thr Tyr
1               5                   10

<210> SEQ ID NO 7
<211> LENGTH: 10
<212> TYPE: PRT
<213> ORGANISM: Lama
<220> FEATURE:
<221> NAME/KEY: MISC_FEATURE
<222> LOCATION: (2)..(2)
<223> OTHER INFORMATION: X is M or P

<400> SEQUENCE: 7

Glu Xaa Ser Gly Ile Ser Gly Trp Asp Tyr
1               5                   10

<210> SEQ ID NO 8
<211> LENGTH: 119
<212> TYPE: PRT
<213> ORGANISM: Artificial Sequence
<220> FEATURE:
<223> OTHER INFORMATION: Humanized lama

<400> SEQUENCE: 8

Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Phe Ser Phe Tyr
                20                  25                  30

Gly Met Gly Trp Phe Arg Gln Ala Pro Gly Lys Glu Gln Glu Phe Val
            35                  40                  45

Ala Asp Ile Arg Thr Ser Ala Gly Arg Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Glu Met Ser Gly Ile Ser Gly Trp Asp Tyr Trp Gly Gln Gly
            100                 105                 110

Thr Gln Val Thr Val Ser Ser
        115

<210> SEQ ID NO 9
<211> LENGTH: 119
<212> TYPE: PRT
<213> ORGANISM: Artificial Sequence
<220> FEATURE:
<223> OTHER INFORMATION: Humanized lama

<400> SEQUENCE: 9

Glu Val Gln Leu Val Glu Ser Gly Gly Gly Val Val Gln Ala Gly Gly
1               5                   10                  15
```

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Glu Met Ser Gly Ile Ser Gly Trp Asp Tyr Trp Gly Gln Gly
            100                 105                 110

Thr Gln Val Lys Val Ser Ser
        115

<210> SEQ ID NO 10
<211> LENGTH: 119
<212> TYPE: PRT
<213> ORGANISM: Artificial Sequence
<220> FEATURE:
<223> OTHER INFORMATION: Humanized lama

<400> SEQUENCE: 10

Glu Val Gln Leu Val Glu Ser Gly Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Glu Met Ser Gly Ile Ser Gly Trp Asp Tyr Trp Gly Gln Gly
            100                 105                 110

Thr Gln Val Gln Val Ser Ser
        115

<210> SEQ ID NO 11
<211> LENGTH: 119
<212> TYPE: PRT
<213> ORGANISM: Artificial Sequence
<220> FEATURE:
<223> OTHER INFORMATION: Humanized lama

<400> SEQUENCE: 11

Glu Val Gln Leu Val Glu Ser Gly Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
50                  55                  60

Lys Gly Arg Phe Thr Ile Ser Arg Asp Asn Ala Lys Asn Thr Val Tyr

```
                65                  70                  75                  80
Leu Gln Met Asn Ser Leu Lys Pro Glu Asp Thr Ala Val Tyr Tyr Cys
                    85                  90                  95

Ala Ala Glu Met Ser Gly Ile Ser Gly Trp Asp Tyr Trp Gly Gln Gly
            100                 105                 110

Thr Gln Val Thr Val Lys Ser
        115

<210> SEQ ID NO 12
<211> LENGTH: 119
<212> TYPE: PRT
<213> ORGANISM: Artificial Sequence
<220> FEATURE:
<223> OTHER INFORMATION: Humanized lama

<400> SEQUENCE: 12

Glu Val Gln Leu Val Glu Ser Gly Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                    85                  90                  95

Ala Ala Glu Met Ser Gly Ile Ser Gly Trp Asp Tyr Trp Gly Gln Gly
            100                 105                 110

Thr Gln Val Thr Val Gln Ser
        115

<210> SEQ ID NO 13
<211> LENGTH: 119
<212> TYPE: PRT
<213> ORGANISM: Artificial Sequence
<220> FEATURE:
<223> OTHER INFORMATION: Humanized lama

<400> SEQUENCE: 13

Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                    85                  90                  95

Ala Ala Glu Met Ser Gly Ile Ser Gly Trp Asp Tyr Trp Gly Gln Gly
            100                 105                 110

Thr Gln Val Lys Val Ser Ser
        115
```

```
<210> SEQ ID NO 14
<211> LENGTH: 119
<212> TYPE: PRT
<213> ORGANISM: Artificial Sequence
<220> FEATURE:
<223> OTHER INFORMATION: Humanized lama

<400> SEQUENCE: 14

Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Gln Val Gln Val Ser Ser
        115

<210> SEQ ID NO 15
<211> LENGTH: 119
<212> TYPE: PRT
<213> ORGANISM: Artificial Sequence
<220> FEATURE:
<223> OTHER INFORMATION: Humanized lama

<400> SEQUENCE: 15

Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Gln Val Thr Val Lys Ser
        115

<210> SEQ ID NO 16
<211> LENGTH: 119
<212> TYPE: PRT
<213> ORGANISM: Artificial Sequence
<220> FEATURE:
<223> OTHER INFORMATION: Humanized lama

<400> SEQUENCE: 16

Glu Val Gln Leu Val Glu Ser Gly Gly Gly Leu Val Gln Ala Gly Gly
```

```
                1               5                   10                  15
            Ser Leu Arg Leu Ser Cys Ala Ala Ser Gly Gly Thr Phe Ser Phe Tyr
                        20                  25                  30

Gly Met Gly Trp Phe Arg Gln Ala Pro Gly Lys Glu Gln Glu Phe Val
                        35                  40                  45

Ala Asp Ile Arg Thr Ser Ala Gly Arg Thr Tyr Tyr Ala Asp Ser Val
                        50                  55                  60

Lys Gly Arg Phe Thr Ile Ser Arg Asp Asn Ala Lys Asn Thr Val Tyr
            65                      70                  75                  80

Leu Gln Met Asn Ser Leu Lys Pro Glu Asp Thr Ala Leu Tyr Tyr Cys
                        85                  90                  95

Ala Ala Glu Met Ser Gly Ile Ser Gly Trp Asp Tyr Trp Gly Gln Gly
                        100                 105                 110

Thr Gln Val Thr Val Gln Ser
                        115

<210> SEQ ID NO 17
<211> LENGTH: 119
<212> TYPE: PRT
<213> ORGANISM: Artificial Sequence
<220> FEATURE:
<223> OTHER INFORMATION: Humanized lama

<400> SEQUENCE: 17

Glu Val Gln Leu Val Glu Ser Gly Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
            35                  40                  45

Ala Asp Ile Arg Thr Ser Ala Gly Arg Thr Tyr Tyr Ala Asp Ser Val
            50                  55                  60

Lys Gly Arg Phe Thr Ile Ser Arg Asp Asn Ala Lys Asn Thr Val Tyr
65                      70                  75                  80

Leu Gln Met Asn Ser Leu Lys Pro Glu Asp Thr Ala Leu Tyr Tyr Cys
            85                  90                  95

Ala Ala Glu Met Ser Gly Ile Ser Gly Trp Asp Tyr Trp Gly Gln Gly
            100                 105                 110

Thr Gln Val Thr Val Ser Ser
            115

<210> SEQ ID NO 18
<211> LENGTH: 119
<212> TYPE: PRT
<213> ORGANISM: Artificial Sequence
<220> FEATURE:
<223> OTHER INFORMATION: Humanized lama

<400> SEQUENCE: 18

Glu Val Gln Leu Val Glu Ser Gly Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
            35                  40                  45

Ala Asp Ile Arg Thr Ser Ala Gly Arg Thr Tyr Tyr Ala Asp Ser Val
            50                  55                  60
```

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
            85                  90                  95

Ala Ala Glu Met Ser Gly Ile Ser Gly Trp Asp Tyr Trp Gly Gln Gly
            100                 105                 110

Thr Gln Val Lys Val Ser Ser
        115

<210> SEQ ID NO 19
<211> LENGTH: 119
<212> TYPE: PRT
<213> ORGANISM: Artificial Sequence
<220> FEATURE:
<223> OTHER INFORMATION: Humanized lama

<400> SEQUENCE: 19

Glu Val Gln Leu Val Glu Ser Gly Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
            85                  90                  95

Ala Ala Glu Met Ser Gly Ile Ser Gly Trp Asp Tyr Trp Gly Gln Gly
            100                 105                 110

Thr Gln Val Gln Val Ser Ser
        115

<210> SEQ ID NO 20
<211> LENGTH: 119
<212> TYPE: PRT
<213> ORGANISM: Artificial Sequence
<220> FEATURE:
<223> OTHER INFORMATION: Humanized lama

<400> SEQUENCE: 20

Glu Val Gln Leu Val Glu Ser Gly Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
            85                  90                  95

Ala Ala Glu Met Ser Gly Ile Ser Gly Trp Asp Tyr Trp Gly Gln Gly
            100                 105                 110

Thr Gln Val Thr Val Lys Ser
        115

<210> SEQ ID NO 21
<211> LENGTH: 119
<212> TYPE: PRT
<213> ORGANISM: Artificial Sequence
<220> FEATURE:
<223> OTHER INFORMATION: Humanized lama

<400> SEQUENCE: 21

Glu Val Gln Leu Val Glu Ser Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Gln Val Thr Val Gln Ser
        115

<210> SEQ ID NO 22
<211> LENGTH: 119
<212> TYPE: PRT
<213> ORGANISM: Artificial Sequence
<220> FEATURE:
<223> OTHER INFORMATION: Humanized lama

<400> SEQUENCE: 22

Glu Val Gln Leu Val Glu Ser Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Leu Val Thr Val Ser Ser
        115

<210> SEQ ID NO 23
<211> LENGTH: 119
<212> TYPE: PRT
<213> ORGANISM: Artificial Sequence
<220> FEATURE:
<223> OTHER INFORMATION: Humanized lama

<400> SEQUENCE: 23

```
Glu Val Gln Leu Val Glu Ser Gly Gly Gly Val Val Gln Pro Gly Gly
1               5                   10                  15

Ser Leu Arg Leu Ser Cys Ala Ala Ser Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Leu Val Thr Val Ser Ser
        115
```

<210> SEQ ID NO 24
<211> LENGTH: 119
<212> TYPE: PRT
<213> ORGANISM: Artificial Sequence
<220> FEATURE:
<223> OTHER INFORMATION: Humanized lama

<400> SEQUENCE: 24

```
Asp Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Leu Val Thr Val Ser Ser
        115
```

<210> SEQ ID NO 25
<211> LENGTH: 119
<212> TYPE: PRT
<213> ORGANISM: Artificial Sequence
<220> FEATURE:
<223> OTHER INFORMATION: Humanized lama

<400> SEQUENCE: 25

```
Asp Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60
```

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Leu Val Thr Val Ser Ser
        115

<210> SEQ ID NO 26
<211> LENGTH: 120
<212> TYPE: PRT
<213> ORGANISM: Artificial Sequence
<220> FEATURE:
<223> OTHER INFORMATION: Humanized lama

<400> SEQUENCE: 26

Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Thr Tyr Tyr Cys
                85                  90                  95

Ala Ala Glu Met Ser Gly Ile Ser Gly Trp Asp Tyr Trp Gly Gln Gly
            100                 105                 110

Thr Gln Val Thr Val Ser Ser Ala
        115                 120

<210> SEQ ID NO 27
<211> LENGTH: 120
<212> TYPE: PRT
<213> ORGANISM: Artificial Sequence
<220> FEATURE:
<223> OTHER INFORMATION: Humanized lama

<400> SEQUENCE: 27

Glu Val Gln Leu Val Glu Ser Gly Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Glu Met Ser Gly Ile Ser Gly Trp Asp Tyr Trp Gly Gln Gly
            100                 105                 110

Thr Gln Val Lys Val Ser Ser Ala

<210> SEQ ID NO 28
<211> LENGTH: 120
<212> TYPE: PRT
<213> ORGANISM: Artificial Sequence
<220> FEATURE:
<223> OTHER INFORMATION: Humanized lama

<400> SEQUENCE: 28

Glu Val Gln Leu Val Glu Ser Gly Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Glu Met Ser Gly Ile Ser Gly Trp Asp Tyr Trp Gly Gln Gly
            100                 105                 110

Thr Gln Val Gln Val Ser Ser Ala
            115                 120

<210> SEQ ID NO 29
<211> LENGTH: 120
<212> TYPE: PRT
<213> ORGANISM: Artificial Sequence
<220> FEATURE:
<223> OTHER INFORMATION: Humanized lama

<400> SEQUENCE: 29

Glu Val Gln Leu Val Glu Ser Gly Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Glu Met Ser Gly Ile Ser Gly Trp Asp Tyr Trp Gly Gln Gly
            100                 105                 110

Thr Gln Val Thr Val Lys Ser Ala
            115                 120

<210> SEQ ID NO 30
<211> LENGTH: 120
<212> TYPE: PRT
<213> ORGANISM: Artificial Sequence
<220> FEATURE:
<223> OTHER INFORMATION: Humanized lama

<400> SEQUENCE: 30

Glu Val Gln Leu Val Glu Ser Gly Gly Gly Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Glu Met Ser Gly Ile Ser Gly Trp Asp Tyr Trp Gly Gln Gly
                100                 105                 110

Thr Gln Val Thr Val Gln Ser Ala
        115                 120

<210> SEQ ID NO 31
<211> LENGTH: 120
<212> TYPE: PRT
<213> ORGANISM: Artificial Sequence
<220> FEATURE:
<223> OTHER INFORMATION: Humanized lama

<400> SEQUENCE: 31

Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Ala Glu Met Ser Gly Ile Ser Gly Trp Asp Tyr Trp Gly Gln Gly
                100                 105                 110

Thr Gln Val Lys Val Ser Ser Ala
        115                 120

<210> SEQ ID NO 32
<211> LENGTH: 120
<212> TYPE: PRT
<213> ORGANISM: Artificial Sequence
<220> FEATURE:
<223> OTHER INFORMATION: Humanized lama

<400> SEQUENCE: 32

Glu Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val

```
                50                  55                  60
Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Leu Tyr Tyr Cys
                 85                  90                  95

Ala Ala Glu Met Ser Gly Ile Ser Gly Trp Asp Tyr Trp Gly Gln Gly
                100                 105                 110

Thr Gln Val Gln Val Ser Ser Ala
            115                 120

<210> SEQ ID NO 33
<211> LENGTH: 120
<212> TYPE: PRT
<213> ORGANISM: Artificial Sequence
<220> FEATURE:
<223> OTHER INFORMATION: Humanized lama

<400> SEQUENCE: 33

Glu Val Gln Leu Val Glu Ser Gly Gly Gly Leu Val Gln Ala Gly Gly
  1               5                  10                  15

Ser Leu Arg Leu Ser Cys Ala Ala Ser Gly Gly Thr Phe Ser Phe Tyr
                 20                  25                  30

Gly Met Gly Trp Phe Arg Gln Ala Pro Gly Lys Glu Gln Glu Phe Val
             35                  40                  45

Ala Asp Ile Arg Thr Ser Ala Gly Arg Thr Tyr Tyr Ala Asp Ser Val
         50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Leu Tyr Tyr Cys
                 85                  90                  95

Ala Ala Glu Met Ser Gly Ile Ser Gly Trp Asp Tyr Trp Gly Gln Gly
                100                 105                 110

Thr Gln Val Thr Val Lys Ser Ala
            115                 120

<210> SEQ ID NO 34
<211> LENGTH: 120
<212> TYPE: PRT
<213> ORGANISM: Artificial Sequence
<220> FEATURE:
<223> OTHER INFORMATION: Humanized lama

<400> SEQUENCE: 34

Glu Val Gln Leu Val Glu Ser Gly Gly Gly Leu Val Gln Ala Gly Gly
  1               5                  10                  15

Ser Leu Arg Leu Ser Cys Ala Ala Ser Gly Gly Thr Phe Ser Phe Tyr
                 20                  25                  30

Gly Met Gly Trp Phe Arg Gln Ala Pro Gly Lys Glu Gln Glu Phe Val
             35                  40                  45

Ala Asp Ile Arg Thr Ser Ala Gly Arg Thr Tyr Tyr Ala Asp Ser Val
         50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Leu Tyr Tyr Cys
                 85                  90                  95

Ala Ala Glu Met Ser Gly Ile Ser Gly Trp Asp Tyr Trp Gly Gln Gly
                100                 105                 110
```

```
Thr Gln Val Thr Val Gln Ser Ala
        115                 120

<210> SEQ ID NO 35
<211> LENGTH: 120
<212> TYPE: PRT
<213> ORGANISM: Artificial Sequence
<220> FEATURE:
<223> OTHER INFORMATION: Humanized lama

<400> SEQUENCE: 35

Glu Val Gln Leu Val Glu Ser Gly Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Gln Val Thr Val Ser Ser Ala
        115                 120

<210> SEQ ID NO 36
<211> LENGTH: 120
<212> TYPE: PRT
<213> ORGANISM: Artificial Sequence
<220> FEATURE:
<223> OTHER INFORMATION: Humanized lama

<400> SEQUENCE: 36

Glu Val Gln Leu Val Glu Ser Gly Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Gln Val Lys Val Ser Ser Ala
        115                 120

<210> SEQ ID NO 37
<211> LENGTH: 120
<212> TYPE: PRT
<213> ORGANISM: Artificial Sequence
<220> FEATURE:
<223> OTHER INFORMATION: Humanized lama
```

-continued

<400> SEQUENCE: 37

Glu Val Gln Leu Val Glu Ser Gly Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Gln Val Gln Val Ser Ser Ala
        115                 120

<210> SEQ ID NO 38
<211> LENGTH: 120
<212> TYPE: PRT
<213> ORGANISM: Artificial Sequence
<220> FEATURE:
<223> OTHER INFORMATION: Humanized lama

<400> SEQUENCE: 38

Glu Val Gln Leu Val Glu Ser Gly Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Gln Val Thr Val Lys Ser Ala
        115                 120

<210> SEQ ID NO 39
<211> LENGTH: 120
<212> TYPE: PRT
<213> ORGANISM: Artificial Sequence
<220> FEATURE:
<223> OTHER INFORMATION: Humanized lama

<400> SEQUENCE: 39

Glu Val Gln Leu Val Glu Ser Gly Gly Gly Val Val Gln Ala Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

```
Ala Asp Ile Arg Thr Ser Ala Gly Arg Thr Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Leu Tyr Tyr Cys
                 85                  90                  95

Ala Ala Glu Met Ser Gly Ile Ser Gly Trp Asp Tyr Trp Gly Gln Gly
            100                 105                 110

Thr Gln Val Thr Val Gln Ser Ala
            115                 120

<210> SEQ ID NO 40
<211> LENGTH: 120
<212> TYPE: PRT
<213> ORGANISM: Artificial Sequence
<220> FEATURE:
<223> OTHER INFORMATION: Humanized lama

<400> SEQUENCE: 40

Glu Val Gln Leu Val Glu Ser Gly Gly Gly Val Val Gln Pro Gly Gly
 1               5                  10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Leu Tyr Tyr Cys
                 85                  90                  95

Ala Ala Glu Met Ser Gly Ile Ser Gly Trp Asp Tyr Trp Gly Gln Gly
            100                 105                 110

Thr Leu Val Thr Val Ser Ser Ala
            115                 120

<210> SEQ ID NO 41
<211> LENGTH: 120
<212> TYPE: PRT
<213> ORGANISM: Artificial Sequence
<220> FEATURE:
<223> OTHER INFORMATION: Humanized lama

<400> SEQUENCE: 41

Glu Val Gln Leu Val Glu Ser Gly Gly Gly Val Val Gln Pro Gly Gly
 1               5                  10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Leu Tyr Tyr Cys
                 85                  90                  95

Ala Ala Glu Met Ser Gly Ile Ser Gly Trp Asp Tyr Trp Gly Gln Gly
            100                 105                 110
```

```
Thr Leu Val Thr Val Ser Ser Ala
        115                 120

<210> SEQ ID NO 42
<211> LENGTH: 120
<212> TYPE: PRT
<213> ORGANISM: Artificial Sequence
<220> FEATURE:
<223> OTHER INFORMATION: Humanized lama

<400> SEQUENCE: 42

Asp Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Gln Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Leu Val Thr Val Ser Ser Ala
        115                 120

<210> SEQ ID NO 43
<211> LENGTH: 120
<212> TYPE: PRT
<213> ORGANISM: Artificial Sequence
<220> FEATURE:
<223> OTHER INFORMATION: Humanized lama

<400> SEQUENCE: 43

Asp Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Met Ser Gly Ile Ser Gly Trp Asp Tyr Trp Gly Gln Gly
            100                 105                 110

Thr Leu Val Thr Val Ser Ser Ala
        115                 120

<210> SEQ ID NO 44
<211> LENGTH: 34
<212> TYPE: PRT
<213> ORGANISM: Artificial Sequence
<220> FEATURE:
<223> OTHER INFORMATION: His6-FLAG3 Tag
```

```
<400> SEQUENCE: 44

His His His His His His Gly Ala Ala Asp Tyr Lys Asp His Asp Gly
1               5                   10                  15

Asp Tyr Lys Asp His Asp Ile Asp Tyr Lys Asp Asp Asp Lys Gly
            20                  25                  30

Ala Ala

<210> SEQ ID NO 45
<211> LENGTH: 5
<212> TYPE: PRT
<213> ORGANISM: Artificial Sequence
<220> FEATURE:
<223> OTHER INFORMATION: C-terminal extender

<400> SEQUENCE: 45

Val Thr Val Lys Ser
1               5

<210> SEQ ID NO 46
<211> LENGTH: 5
<212> TYPE: PRT
<213> ORGANISM: Artificial Sequence
<220> FEATURE:
<223> OTHER INFORMATION: C-terminal extender

<400> SEQUENCE: 46

Val Thr Val Gln Ser
1               5

<210> SEQ ID NO 47
<211> LENGTH: 5
<212> TYPE: PRT
<213> ORGANISM: Artificial Sequence
<220> FEATURE:
<223> OTHER INFORMATION: C-terminal extender

<400> SEQUENCE: 47

Val Lys Val Ser Ser
1               5

<210> SEQ ID NO 48
<211> LENGTH: 5
<212> TYPE: PRT
<213> ORGANISM: Artificial Sequence
<220> FEATURE:
<223> OTHER INFORMATION: C-terminal extender

<400> SEQUENCE: 48

Val Gln Val Ser Ser
1               5

<210> SEQ ID NO 49
<211> LENGTH: 6
<212> TYPE: PRT
<213> ORGANISM: Artificial Sequence
<220> FEATURE:
<223> OTHER INFORMATION: C-terminal extender
<220> FEATURE:
<221> NAME/KEY: MISC_FEATURE
<222> LOCATION: (6)..(6)
<223> OTHER INFORMATION: X is any sequence of 1-10 natural amino acids

<400> SEQUENCE: 49

Val Thr Val Lys Ser Xaa
1               5
```

```
<210> SEQ ID NO 50
<211> LENGTH: 6
<212> TYPE: PRT
<213> ORGANISM: Artificial Sequence
<220> FEATURE:
<223> OTHER INFORMATION: C-terminal extender
<220> FEATURE:
<221> NAME/KEY: MISC_FEATURE
<222> LOCATION: (6)..(6)
<223> OTHER INFORMATION: X is any sequence of 1-10 natural amino acids

<400> SEQUENCE: 50

Val Thr Val Gln Ser Xaa
1               5

<210> SEQ ID NO 51
<211> LENGTH: 6
<212> TYPE: PRT
<213> ORGANISM: Artificial Sequence
<220> FEATURE:
<223> OTHER INFORMATION: C-terminal extender
<220> FEATURE:
<221> NAME/KEY: MISC_FEATURE
<222> LOCATION: (6)..(6)
<223> OTHER INFORMATION: X is any sequence of 1-10 natural amino acids

<400> SEQUENCE: 51

Val Lys Val Ser Ser Xaa
1               5

<210> SEQ ID NO 52
<211> LENGTH: 6
<212> TYPE: PRT
<213> ORGANISM: Artificial Sequence
<220> FEATURE:
<223> OTHER INFORMATION: C-terminal extender
<220> FEATURE:
<221> NAME/KEY: MISC_FEATURE
<222> LOCATION: (6)..(6)
<223> OTHER INFORMATION: X is any sequence of 1-10 natural amino acids

<400> SEQUENCE: 52

Val Gln Val Ser Ser Xaa
1               5

<210> SEQ ID NO 53
<211> LENGTH: 6
<212> TYPE: PRT
<213> ORGANISM: Artificial Sequence
<220> FEATURE:
<223> OTHER INFORMATION: C-terminal extender

<400> SEQUENCE: 53

Val Thr Val Lys Ser Ala
1               5

<210> SEQ ID NO 54
<211> LENGTH: 6
<212> TYPE: PRT
<213> ORGANISM: Artificial Sequence
<220> FEATURE:
<223> OTHER INFORMATION: C-terminal extender

<400> SEQUENCE: 54

Val Thr Val Gln Ser Ala
1               5
```

```
<210> SEQ ID NO 55
<211> LENGTH: 6
<212> TYPE: PRT
<213> ORGANISM: Artificial Sequence
<220> FEATURE:
<223> OTHER INFORMATION: C-terminal extender

<400> SEQUENCE: 55

Val Lys Val Ser Ser Ala
1               5

<210> SEQ ID NO 56
<211> LENGTH: 6
<212> TYPE: PRT
<213> ORGANISM: Artificial Sequence
<220> FEATURE:
<223> OTHER INFORMATION: C-terminal extender

<400> SEQUENCE: 56

Val Gln Val Ser Ser Ala
1               5

<210> SEQ ID NO 57
<211> LENGTH: 5
<212> TYPE: PRT
<213> ORGANISM: Artificial Sequence
<220> FEATURE:
<223> OTHER INFORMATION: C-terminal extender

<400> SEQUENCE: 57

Val Thr Val Ser Ser
1               5

<210> SEQ ID NO 58
<211> LENGTH: 6
<212> TYPE: PRT
<213> ORGANISM: Artificial Sequence
<220> FEATURE:
<223> OTHER INFORMATION: C-terminal extender
<220> FEATURE:
<221> NAME/KEY: MISC_FEATURE
<222> LOCATION: (6)..(6)
<223> OTHER INFORMATION: X is any sequence of 1-10 natural amino acids

<400> SEQUENCE: 58

Val Thr Val Ser Ser Xaa
1               5

<210> SEQ ID NO 59
<211> LENGTH: 6
<212> TYPE: PRT
<213> ORGANISM: Artificial Sequence
<220> FEATURE:
<223> OTHER INFORMATION: C-terminal extender

<400> SEQUENCE: 59

Val Thr Val Ser Ser Ala
1               5

<210> SEQ ID NO 60
<211> LENGTH: 119
<212> TYPE: PRT
<213> ORGANISM: Artificial Sequence
<220> FEATURE:
<223> OTHER INFORMATION: Humanized lama
<220> FEATURE:
<221> NAME/KEY: MISC_FEATURE
<222> LOCATION: (1)..(1)
<223> OTHER INFORMATION: X is D or E
```

<400> SEQUENCE: 60

| | | | | | | | | | | | | | | |
|---|---|---|---|---|---|---|---|---|---|---|---|---|---|---|
| Xaa | Val | Gln | Leu | Val | Glu | Ser | Gly | Gly | Gly | Val | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Gly | Thr | Phe | Ser | Phe | Tyr |
| | | | 20 | | | | | 25 | | | | | 30 | | |
| Gly | Met | Gly | Trp | Phe | Arg | Gln | Ala | Pro | Gly | Lys | Glu | Arg | Glu | Phe | Val |
| | | 35 | | | | | 40 | | | | | 45 | | | |
| Ala | Asp | Ile | Arg | Thr | Ser | Ala | Gly | Arg | Thr | Tyr | Tyr | Ala | Asp | Ser | Val |
| | 50 | | | | | 55 | | | | | 60 | | | | |
| Lys | Gly | Arg | Phe | Thr | Ile | Ser | Arg | Asp | Asn | Ser | Lys | Asn | Thr | Val | Tyr |
| 65 | | | | | 70 | | | | | 75 | | | | | 80 |
| Leu | Gln | Met | Asn | Ser | Leu | Arg | Pro | Glu | Asp | Thr | Ala | Leu | Tyr | Tyr | Cys |
| | | | | 85 | | | | | 90 | | | | | 95 | |
| Ala | Ala | Glu | Pro | Ser | Gly | Ile | Ser | Gly | Trp | Asp | Tyr | Trp | Gly | Gln | Gly |
| | | | 100 | | | | | 105 | | | | | 110 | | |
| Thr | Leu | Val | Thr | Val | Ser | Ser | | | | | | | | | |
| | | | 115 | | | | | | | | | | | | |

<210> SEQ ID NO 61
<211> LENGTH: 1272
<212> TYPE: DNA
<213> ORGANISM: Artificial Sequence
<220> FEATURE:
<223> OTHER INFORMATION: Humanized lama

<400> SEQUENCE: 61

| | | | | | |
|---|---|---|---|---|---|
| gacgtgcaat | tggtggagtc | tgggggagga | gtggtgcagc | cggggggctc | tctgagactc | 60 |
| tcctgtgcag | cctctggtgg | caccttcagt | ttctatggca | tgggctggtt | ccgccaggct | 120 |
| ccagggaagg | agcgcgagtt | tgtagcagat | attagaacca | gtgctggtag | gacatactat | 180 |
| gcagactccg | tgaagggccg | attcaccatc | tccagagaca | acagcaagaa | cacggtgtat | 240 |
| ctgcaaatga | acagcctgcg | ccctgaggac | acggccctgt | attactgtgc | agcagagcca | 300 |
| agtggaataa | gtggttggga | ctactggggc | caggggaccc | tggtcacggt | ctcctccgga | 360 |
| ggcggtgggt | caggtggcgg | aggcagcggt | ggaggaggta | gtggcggtgg | cggtagtggg | 420 |
| ggtggaggca | gcggaggcgg | aggcagtggg | ggcggtggat | ccgaggtgca | gttggtggag | 480 |
| tctggggag | gagtggtgca | gccgggggc | tctctgagac | tctcctgtgc | agcctctggt | 540 |
| ggcaccttca | gtttctatgg | catgggctgg | ttccgccagg | ctccagggaa | ggagcgcgag | 600 |
| tttgtagcag | atattagaac | cagtgctggt | aggacatact | atgcagactc | cgtgaagggc | 660 |
| cgattcacca | tctccagaga | caacagcaag | aacacggtgt | atctgcaaat | gaacagcctg | 720 |
| cgccctgagg | acacggccct | gtattactgt | gcagcagagc | caagtggaat | aagtggttgg | 780 |
| gactactggg | gccaggggac | cctggtcacg | gtctcgagcg | gaggcggtgg | gtcaggtggc | 840 |
| ggaggcagcg | gtggaggagg | tagtggcggt | ggcggtagtg | ggggtggagg | cagcggaggc | 900 |
| ggaggcagtg | ggggcggtgg | ctcagaggta | caactagtgg | agtctggagg | tggcgttgtg | 960 |
| caaccgggta | acagtctgcg | ccttagctgc | gcagcgtctg | gctttacctt | cagctccttt | 1020 |
| ggcatgagct | gggttcgcca | ggctccggga | aaggactgg | aatgggtttc | gtctattagc | 1080 |
| ggcagtggta | gcgatacgct | ctacgcggac | tccgtgaagg | ccgtttcac | catctcccgc | 1140 |
| gataacgcca | aaactacact | gtatctgcaa | atgaatagcc | tgtcctga | agatacggcc | 1200 |
| ctgtattact | gtactattgg | tggctcgtta | agccgttctt | cacagggtac | cctggtcacc | 1260 |

-continued

```
gtctcctcag cg                                                         1272
```

<210> SEQ ID NO 62
<211> LENGTH: 424
<212> TYPE: PRT
<213> ORGANISM: Artificial Sequence
<220> FEATURE:
<223> OTHER INFORMATION: Humanized lama

<400> SEQUENCE: 62

```
Asp Val Gln Leu Val Glu Ser Gly Gly Gly Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Ser Gly Gly Gly Gly Ser Gly Gly Gly Gly Ser
    130                 135                 140

Gly Gly Gly Gly Ser Gly Gly Gly Ser Glu Val Gln Leu Val Glu
145                 150                 155                 160

Ser Gly Gly Val Val Gln Pro Gly Gly Ser Leu Arg Leu Ser Cys
                165                 170                 175

Ala Ala Ser Gly Gly Thr Phe Ser Phe Tyr Gly Met Gly Trp Phe Arg
            180                 185                 190

Gln Ala Pro Gly Lys Glu Arg Glu Phe Val Ala Asp Ile Arg Thr Ser
        195                 200                 205

Ala Gly Arg Thr Tyr Tyr Ala Asp Ser Val Lys Gly Arg Phe Thr Ile
    210                 215                 220

Ser Arg Asp Asn Ser Lys Asn Thr Val Tyr Leu Gln Met Asn Ser Leu
225                 230                 235                 240

Arg Pro Glu Asp Thr Ala Leu Tyr Tyr Cys Ala Ala Glu Pro Ser Gly
                245                 250                 255

Ile Ser Gly Trp Asp Tyr Trp Gly Gln Gly Thr Leu Val Thr Val Ser
            260                 265                 270

Ser Gly Gly Gly Gly Ser Gly Gly Gly Ser Gly Gly Gly Gly Ser
        275                 280                 285

Gly Gly Gly Gly Ser Gly Gly Gly Ser Gly Gly Gly Gly Ser Gly
    290                 295                 300

Gly Gly Ser Glu Val Gln Leu Val Glu Ser Gly Gly Val Val
305                 310                 315                 320

Gln Pro Gly Asn Ser Leu Arg Leu Ser Cys Ala Ala Ser Gly Phe Thr
                325                 330                 335

Phe Ser Ser Phe Gly Met Ser Trp Val Arg Gln Ala Pro Gly Lys Gly
            340                 345                 350

Leu Glu Trp Val Ser Ser Ile Ser Gly Ser Gly Ser Asp Thr Leu Tyr
```

```
                355                 360                 365
Ala Asp Ser Val Lys Gly Arg Phe Thr Ile Ser Arg Asp Asn Ala Lys
        370                 375                 380

Thr Thr Leu Tyr Leu Gln Met Asn Ser Leu Arg Pro Glu Asp Thr Ala
385                 390                 395                 400

Leu Tyr Tyr Cys Thr Ile Gly Gly Ser Leu Ser Arg Ser Gln Gly
                405                 410                 415

Thr Leu Val Thr Val Ser Ser Ala
            420

<210> SEQ ID NO 63
<211> LENGTH: 810
<212> TYPE: DNA
<213> ORGANISM: Artificial Sequence
<220> FEATURE:
<223> OTHER INFORMATION: Humanized lama

<400> SEQUENCE: 63
gacgtgcaat tggtggagtc tgggggagga gtggtgcagc cggggggctc tctgagactc      60
tcctgtgcag cctctggtgg caccttcagt ttctatggca tgggctggtt ccgccaggct     120
ccagggaagg agcgcgagtt tgtagcagat attagaacca gtgctggtag acatactat     180 gcagactccg tgaagggccg attcaccatc tccagagaca acagcaagaa cacggtgtat     240
ctgcaaatga acagcctgcg ccctgaggac acggccctgt attactgtgc agcagagcca     300
agtggaataa gtggttggga ctactggggc caggggaccc tggtcacggt ctcctccgga     360
ggcggtgggt caggtggcgg aggcagcggt ggaggaggta gtggcggtgg cggtagtggg     420
ggtggaggca gcggaggcgg aggcagtggg ggcggtggat ccgaggtgca gttggtggag     480 tctgaggtg cgttgtgca accgggtaac agtctgcgcc ttagctgcgc agcgtctggc     540
tttaccttca gctcctttgg catgagctgg gttcgccagg ctccgggaaa aggactggaa     600
tgggtttcgt ctattagcgg cagtggtagc gatacgctct acgcggactc cgtgaagggc     660
cgtttcacca tctcccgcga taacgccaaa actacactgt atctgcaaat gaatagcctg     720
cgtcctgaag atacggccct gtattactgt actattggtg gctcgttaag ccgttcttca     780
cagggtaccc tggtcaccgt ctcctcagcg                                      810

<210> SEQ ID NO 64
<211> LENGTH: 270
<212> TYPE: PRT
<213> ORGANISM: Artificial Sequence
<220> FEATURE:
<223> OTHER INFORMATION: Humanized lama

<400> SEQUENCE: 64

Asp Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95
```

```
Ala Ala Glu Pro Ser Gly Ile Ser Gly Trp Asp Tyr Trp Gly Gln Gly
            100                 105                 110

Thr Leu Val Thr Val Ser Ser Gly Gly Gly Ser Gly Gly Gly Gly Gly
        115                 120                 125

Ser Gly Gly Gly Ser Gly Gly Gly Gly Ser Gly Gly Gly Gly Gly Ser
    130                 135                 140

Gly Gly Gly Gly Ser Gly Gly Gly Ser Glu Val Gln Leu Val Glu
145                 150                 155                 160

Ser Gly Gly Gly Val Val Gln Pro Gly Asn Ser Leu Arg Leu Ser Cys
                165                 170                 175

Ala Ala Ser Gly Phe Thr Phe Ser Ser Phe Gly Met Ser Trp Val Arg
            180                 185                 190

Gln Ala Pro Gly Lys Gly Leu Glu Trp Val Ser Ser Ile Ser Gly Ser
        195                 200                 205

Gly Ser Asp Thr Leu Tyr Ala Asp Ser Val Lys Gly Arg Phe Thr Ile
    210                 215                 220

Ser Arg Asp Asn Ala Lys Thr Thr Leu Tyr Leu Gln Met Asn Ser Leu
225                 230                 235                 240

Arg Pro Glu Asp Thr Ala Leu Tyr Tyr Cys Thr Ile Gly Gly Ser Leu
                245                 250                 255

Ser Arg Ser Ser Gln Gly Thr Leu Val Thr Val Ser Ser Ala
            260                 265                 270

<210> SEQ ID NO 65
<211> LENGTH: 35
<212> TYPE: PRT
<213> ORGANISM: Artificial Sequence
<220> FEATURE:
<223> OTHER INFORMATION: Humanized lama

<400> SEQUENCE: 65

Gly Gly Gly Gly Ser Gly Gly Gly Gly Ser Gly Gly Gly Gly Ser Gly
1               5                   10                  15

Gly Gly Ser Gly Gly Gly Gly Ser Gly Gly Gly Gly Ser Gly Gly
            20                  25                  30

Gly Gly Ser
        35

<210> SEQ ID NO 66
<211> LENGTH: 116
<212> TYPE: PRT
<213> ORGANISM: Artificial Sequence
<220> FEATURE:
<223> OTHER INFORMATION: Humanized lama
<220> FEATURE:
<221> NAME/KEY: MISC_FEATURE
<222> LOCATION: (11)..(11)
<223> OTHER INFORMATION: X is L or V
<220> FEATURE:
<221> NAME/KEY: MISC_FEATURE
<222> LOCATION: (93)..(93)
<223> OTHER INFORMATION: X is L or V

<400> SEQUENCE: 66

Glu Val Gln Leu Val Glu Ser Gly Gly Gly Xaa Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45
```

```
Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Xaa Tyr Tyr Cys
                 85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 67
<211> LENGTH: 10
<212> TYPE: PRT
<213> ORGANISM: Lama

<400> SEQUENCE: 67

Gly Phe Thr Phe Ser Ser Phe Gly Met Ser
1               5                   10

<210> SEQ ID NO 68
<211> LENGTH: 17
<212> TYPE: PRT
<213> ORGANISM: Lama

<400> SEQUENCE: 68

Ser Ile Ser Gly Ser Gly Ser Asp Thr Leu Tyr Ala Asp Ser Val Lys
1               5                   10                  15

Gly

<210> SEQ ID NO 69
<211> LENGTH: 6
<212> TYPE: PRT
<213> ORGANISM: Lama

<400> SEQUENCE: 69

Gly Gly Ser Leu Ser Arg
1               5

<210> SEQ ID NO 70
<211> LENGTH: 85
<212> TYPE: PRT
<213> ORGANISM: Saccharomyces cerevisiae

<400> SEQUENCE: 70

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg
            85

<210> SEQ ID NO 71
```

```
<211> LENGTH: 11
<212> TYPE: PRT
<213> ORGANISM: Rattus

<400> SEQUENCE: 71

Lys Thr Ser Gln Asn Ile Phe Glu Asn Leu Ala
1               5                   10

<210> SEQ ID NO 72
<211> LENGTH: 7
<212> TYPE: PRT
<213> ORGANISM: Rattus

<400> SEQUENCE: 72

Asn Ala Ser Pro Leu Gln Ala
1               5

<210> SEQ ID NO 73
<211> LENGTH: 8
<212> TYPE: PRT
<213> ORGANISM: Rattus

<400> SEQUENCE: 73

His Gln Tyr Tyr Ser Gly Tyr Thr
1               5

<210> SEQ ID NO 74
<211> LENGTH: 10
<212> TYPE: PRT
<213> ORGANISM: Rattus

<400> SEQUENCE: 74

Gly Phe Thr Phe Ser Asp Tyr His Met Ala
1               5                   10

<210> SEQ ID NO 75
<211> LENGTH: 17
<212> TYPE: PRT
<213> ORGANISM: Rattus

<400> SEQUENCE: 75

Ser Ile Thr Leu Asp Ala Thr Tyr Thr Tyr Tyr Arg Asp Ser Val Arg
1               5                   10                  15

Gly

<210> SEQ ID NO 76
<211> LENGTH: 10
<212> TYPE: PRT
<213> ORGANISM: Rattus

<400> SEQUENCE: 76

His Arg Gly Phe Ser Val Trp Leu Asp Tyr
1               5                   10

<210> SEQ ID NO 77
<211> LENGTH: 10
<212> TYPE: PRT
<213> ORGANISM: Rattus

<400> SEQUENCE: 77

Gly Tyr Ile Phe Thr Asp Tyr Ala Met His
1               5                   10

<210> SEQ ID NO 78
```

```
<211> LENGTH: 16
<212> TYPE: PRT
<213> ORGANISM: Rattus

<400> SEQUENCE: 78

Thr Phe Ile Pro Leu Leu Asp Thr Ser Asp Tyr Asn Gln Asn Phe Lys
1               5                   10                  15

<210> SEQ ID NO 79
<211> LENGTH: 11
<212> TYPE: PRT
<213> ORGANISM: Rattus

<400> SEQUENCE: 79

Met Gly Val Thr His Ser Tyr Val Met Asp Ala
1               5                   10

<210> SEQ ID NO 80
<211> LENGTH: 11
<212> TYPE: PRT
<213> ORGANISM: Rattus

<400> SEQUENCE: 80

Arg Ala Ser Gln Pro Ile Ser Ile Ser Val His
1               5                   10

<210> SEQ ID NO 81
<211> LENGTH: 7
<212> TYPE: PRT
<213> ORGANISM: Rattus

<400> SEQUENCE: 81

Phe Ala Ser Gln Ser Ile Ser
1               5

<210> SEQ ID NO 82
<211> LENGTH: 9
<212> TYPE: PRT
<213> ORGANISM: Rattus

<400> SEQUENCE: 82

Gln Gln Thr Phe Ser Leu Pro Tyr Thr
1               5

<210> SEQ ID NO 83
<211> LENGTH: 10
<212> TYPE: PRT
<213> ORGANISM: Mus

<400> SEQUENCE: 83

Gly Phe Ile Ile Lys Ala Thr Tyr Met His
1               5                   10

<210> SEQ ID NO 84
<211> LENGTH: 17
<212> TYPE: PRT
<213> ORGANISM: Mus

<400> SEQUENCE: 84

Arg Ile Asp Pro Ala Asn Gly Glu Thr Lys Tyr Asp Pro Lys Phe Gln
1               5                   10                  15

Val

<210> SEQ ID NO 85
```

<211> LENGTH: 7
<212> TYPE: PRT
<213> ORGANISM: Mus

<400> SEQUENCE: 85

Tyr Ala Trp Tyr Phe Asp Val
1               5

<210> SEQ ID NO 86
<211> LENGTH: 11
<212> TYPE: PRT
<213> ORGANISM: Mus

<400> SEQUENCE: 86

Arg Ala Ser Glu Asn Ile Tyr Ser Phe Leu Ala
1               5                   10

<210> SEQ ID NO 87
<211> LENGTH: 7
<212> TYPE: PRT
<213> ORGANISM: Mus

<400> SEQUENCE: 87

His Ala Lys Thr Leu Ala Glu
1               5

<210> SEQ ID NO 88
<211> LENGTH: 9
<212> TYPE: PRT
<213> ORGANISM: Mus

<400> SEQUENCE: 88

Gln His Tyr Tyr Gly Ser Pro Leu Thr
1               5

<210> SEQ ID NO 89
<211> LENGTH: 447
<212> TYPE: PRT
<213> ORGANISM: Artificial Sequence
<220> FEATURE:
<223> OTHER INFORMATION: Humanized mouse

<400> SEQUENCE: 89

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
        50                  55                  60

Lys Asn Arg Val Thr Leu Thr Thr Asp Ser Ser Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Lys Thr Tyr Thr Cys Asn Val Asp His Lys
    195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 90
<211> LENGTH: 218
<212> TYPE: PRT
<213> ORGANISM: Artificial Sequence
<220> FEATURE:
<223> OTHER INFORMATION: Humanized mouse

<400> SEQUENCE: 90

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
50                  55                  60
```

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
            85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
210                 215

<210> SEQ ID NO 91
<211> LENGTH: 440
<212> TYPE: PRT
<213> ORGANISM: Homo sapiens

<400> SEQUENCE: 91

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
            85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
            165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
            275                 280                 285

Phe Asn Ser Thr Tyr Arg Val Val Ser Val Leu Thr Val Leu His Gln
        290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 92
<211> LENGTH: 214
<212> TYPE: PRT
<213> ORGANISM: Homo sapiens

<400> SEQUENCE: 92

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln

```
                145                 150                 155                 160
Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 93
<211> LENGTH: 153
<212> TYPE: PRT
<213> ORGANISM: Artificial Sequence
<220> FEATURE:
<223> OTHER INFORMATION: Humanized lama

<400> SEQUENCE: 93

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Ala Asp Tyr Lys Asp His Asp
        115                 120                 125

Gly Asp Tyr Lys Asp His Asp Ile Asp Tyr Lys Asp Asp Asp Asp Lys
    130                 135                 140

Gly Ala Ala His His His His His His
145                 150

<210> SEQ ID NO 94
<211> LENGTH: 153
<212> TYPE: PRT
<213> ORGANISM: Artificial Sequence
<220> FEATURE:
<223> OTHER INFORMATION: Humanized lama

<400> SEQUENCE: 94

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Ser Ser Lys Asn Thr Val Tyr
65                  70                  75                  80
```

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Ala Asp Tyr Lys Asp His Asp
        115                 120                 125

Gly Asp Tyr Lys Asp His Asp Ile Asp Tyr Lys Asp Asp Asp Asp Lys
    130                 135                 140

Gly Ala Ala His His His His His His
145                 150

<210> SEQ ID NO 95
<211> LENGTH: 153
<212> TYPE: PRT
<213> ORGANISM: Artificial Sequence
<220> FEATURE:
<223> OTHER INFORMATION: Humanized lama

<400> SEQUENCE: 95

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Val Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Ala Asp Tyr Lys Asp His Asp
        115                 120                 125

Gly Asp Tyr Lys Asp His Asp Ile Asp Tyr Lys Asp Asp Asp Asp Lys
    130                 135                 140

Gly Ala Ala His His His His His His
145                 150

<210> SEQ ID NO 96
<211> LENGTH: 153
<212> TYPE: PRT
<213> ORGANISM: Artificial Sequence
<220> FEATURE:
<223> OTHER INFORMATION: Humanized lama

<400> SEQUENCE: 96

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Gly Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Ala Asp Tyr Lys Asp His Asp
        115                 120                 125

Gly Asp Tyr Lys Asp His Asp Ile Asp Tyr Lys Asp Asp Asp Asp Lys
    130                 135                 140

Gly Ala Ala His His His His His His
145                 150

<210> SEQ ID NO 97
<211> LENGTH: 153
<212> TYPE: PRT
<213> ORGANISM: Artificial Sequence
<220> FEATURE:
<223> OTHER INFORMATION: Humanized lama

<400> SEQUENCE: 97

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Arg Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Ala Asp Tyr Lys Asp His Asp
        115                 120                 125

Gly Asp Tyr Lys Asp His Asp Ile Asp Tyr Lys Asp Asp Asp Asp Lys
    130                 135                 140

Gly Ala Ala His His His His His His
145                 150

<210> SEQ ID NO 98
<211> LENGTH: 153
<212> TYPE: PRT
<213> ORGANISM: Artificial Sequence
<220> FEATURE:
<223> OTHER INFORMATION: Humanized lama

<400> SEQUENCE: 98

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Gln Ser Lys Asn Thr Val Tyr

```
                65                  70                  75                  80
Leu Gln Met Asn Ser Leu Arg Pro Glu Asp Thr Ala Leu Tyr Tyr Cys
                    85                  90                  95

Ala Ala Glu Pro Ser Gly Ile Ser Gly Trp Asp Tyr Trp Gly Gln Gly
                100                 105                 110

Thr Leu Val Thr Val Ser Ser Ala Ala Ala Asp Tyr Lys Asp His Asp
                115                 120                 125

Gly Asp Tyr Lys Asp His Asp Ile Asp Tyr Lys Asp Asp Asp Asp Lys
            130                 135                 140

Gly Ala Ala His His His His His His
145                 150

<210> SEQ ID NO 99
<211> LENGTH: 153
<212> TYPE: PRT
<213> ORGANISM: Artificial Sequence
<220> FEATURE:
<223> OTHER INFORMATION: Humanized lama

<400> SEQUENCE: 99

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
                20                  25                  30

Gly Met Gly Trp Phe Arg Gln Ala Pro Gly Lys Glu Arg Glu Phe Val
            35                  40                  45

Ala Asp Ile Arg Thr Ser Ala Gly Arg Thr Tyr Tyr Ala Asp Ser Val
        50                  55                  60

Lys Gly Arg Phe Thr Ile Ser Arg Asp Met Ser Lys Asn Thr Val Tyr
65                  70                  75                  80

Leu Gln Met Asn Ser Leu Arg Pro Glu Asp Thr Ala Leu Tyr Tyr Cys
                    85                  90                  95

Ala Ala Glu Pro Ser Gly Ile Ser Gly Trp Asp Tyr Trp Gly Gln Gly
                100                 105                 110

Thr Leu Val Thr Val Ser Ser Ala Ala Ala Asp Tyr Lys Asp His Asp
                115                 120                 125

Gly Asp Tyr Lys Asp His Asp Ile Asp Tyr Lys Asp Asp Asp Asp Lys
            130                 135                 140

Gly Ala Ala His His His His His His
145                 150

<210> SEQ ID NO 100
<211> LENGTH: 153
<212> TYPE: PRT
<213> ORGANISM: Artificial Sequence
<220> FEATURE:
<223> OTHER INFORMATION: Humanized lama

<400> SEQUENCE: 100

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
                20                  25                  30

Gly Met Gly Trp Phe Arg Gln Ala Pro Gly Lys Glu Arg Glu Phe Val
            35                  40                  45

Ala Asp Ile Arg Thr Ser Ala Gly Arg Thr Tyr Tyr Ala Asp Ser Val
        50                  55                  60
```

```
Lys Gly Arg Phe Thr Ile Ser Arg Asp His Ser Lys Asn Thr Val Tyr
 65                  70                  75                  80

Leu Gln Met Asn Ser Leu Arg Pro Glu Asp Thr Ala Leu Tyr Tyr Cys
                 85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Ala Asp Tyr Lys Asp His Asp
        115                 120                 125

Gly Asp Tyr Lys Asp His Asp Ile Asp Tyr Lys Asp Asp Asp Asp Lys
    130                 135                 140

Gly Ala Ala His His His His His His
145                 150

<210> SEQ ID NO 101
<211> LENGTH: 153
<212> TYPE: PRT
<213> ORGANISM: Artificial Sequence
<220> FEATURE:
<223> OTHER INFORMATION: Humanized lama

<400> SEQUENCE: 101

Glu Val Gln Leu Val Glu Ser Gly Gly Gly Val Val Gln Pro Gly Gly
 1                5                  10                  15

Ser Leu Arg Leu Ser Cys Ala Ala Ser Gly Gly Thr Phe Ser Phe Tyr
                 20                  25                  30

Gly Met Gly Trp Phe Arg Gln Ala Pro Gly Lys Glu Arg Glu Phe Val
             35                  40                  45

Ala Asp Ile Arg Thr Ser Ala Gly Arg Thr Tyr Tyr Ala Asp Ser Val
 50                  55                  60

Lys Gly Arg Phe Thr Ile Ser Arg Asp Thr Ser Lys Asn Thr Val Tyr
 65                  70                  75                  80

Leu Gln Met Asn Ser Leu Arg Pro Glu Asp Thr Ala Leu Tyr Tyr Cys
                 85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Ala Asp Tyr Lys Asp His Asp
        115                 120                 125

Gly Asp Tyr Lys Asp His Asp Ile Asp Tyr Lys Asp Asp Asp Asp Lys
    130                 135                 140

Gly Ala Ala His His His His His His
145                 150

<210> SEQ ID NO 102
<211> LENGTH: 153
<212> TYPE: PRT
<213> ORGANISM: Artificial Sequence
<220> FEATURE:
<223> OTHER INFORMATION: Humanized lama

<400> SEQUENCE: 102

Glu Val Gln Leu Val Glu Ser Gly Gly Gly Val Val Gln Pro Gly Gly
 1                5                  10                  15

Ser Leu Arg Leu Ser Cys Ala Ala Ser Gly Gly Thr Phe Ser Phe Tyr
                 20                  25                  30

Gly Met Gly Trp Phe Arg Gln Ala Pro Gly Lys Glu Arg Glu Phe Val
             35                  40                  45

Ala Asp Ile Arg Thr Ser Ala Gly Arg Thr Tyr Tyr Ala Asp Ser Val
 50                  55                  60
```

-continued

Lys Gly Arg Phe Thr Ile Ser Arg Asp Asp Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Ala Asp Tyr Lys Asp His Asp
        115                 120                 125

Gly Asp Tyr Lys Asp His Asp Ile Asp Tyr Lys Asp Asp Asp Asp Lys
    130                 135                 140

Gly Ala Ala His His His His His His
145                 150

<210> SEQ ID NO 103
<211> LENGTH: 153
<212> TYPE: PRT
<213> ORGANISM: Artificial Sequence
<220> FEATURE:
<223> OTHER INFORMATION: Humanized lama

<400> SEQUENCE: 103

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
    50                  55                  60

Lys Gly Arg Phe Thr Ile Ser Arg Asp Glu Ser Lys Asn Thr Val Tyr
65                  70                  75                  80

Leu Gln Met Asn Ser Leu Arg Pro Glu Asp Thr Ala Leu Tyr Tyr Cys
                85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Ala Asp Tyr Lys Asp His Asp
        115                 120                 125

Gly Asp Tyr Lys Asp His Asp Ile Asp Tyr Lys Asp Asp Asp Asp Lys
    130                 135                 140

Gly Ala Ala His His His His His His
145                 150

<210> SEQ ID NO 104
<211> LENGTH: 153
<212> TYPE: PRT
<213> ORGANISM: Artificial Sequence
<220> FEATURE:
<223> OTHER INFORMATION: Humanized lama

<400> SEQUENCE: 104

Glu Val Gln Leu Val Glu Ser Gly Gly Gly Val Val Gln Pro Gly Gly
1               5                   10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val

```
                    50                  55                  60
Lys Gly Arg Phe Thr Ile Ser Arg Asp Trp Ser Lys Asn Thr Val Tyr
 65                  70                  75                  80

Leu Gln Met Asn Ser Leu Arg Pro Glu Asp Thr Ala Leu Tyr Tyr Cys
                 85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Ala Asp Tyr Lys Asp His Asp
        115                 120                 125

Gly Asp Tyr Lys Asp His Asp Ile Asp Tyr Lys Asp Asp Asp Asp Lys
    130                 135                 140

Gly Ala Ala His His His His His His
145                 150

<210> SEQ ID NO 105
<211> LENGTH: 153
<212> TYPE: PRT
<213> ORGANISM: Artificial Sequence
<220> FEATURE:
<223> OTHER INFORMATION: Humanized lama

<400> SEQUENCE: 105

Glu Val Gln Leu Val Glu Ser Gly Gly Gly Val Val Gln Pro Gly Gly
  1               5                  10                  15

Ser Leu Arg Leu Ser Cys Ala Ala Ser Gly Gly Thr Phe Ser Phe Tyr
                 20                  25                  30

Gly Met Gly Trp Phe Arg Gln Ala Pro Gly Lys Glu Arg Glu Phe Val
             35                  40                  45

Ala Asp Ile Arg Thr Ser Ala Gly Arg Thr Tyr Tyr Ala Asp Ser Val
         50                  55                  60

Lys Gly Arg Phe Thr Ile Ser Arg Asp Phe Ser Lys Asn Thr Val Tyr
 65                  70                  75                  80

Leu Gln Met Asn Ser Leu Arg Pro Glu Asp Thr Ala Leu Tyr Tyr Cys
                 85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Ala Asp Tyr Lys Asp His Asp
        115                 120                 125

Gly Asp Tyr Lys Asp His Asp Ile Asp Tyr Lys Asp Asp Asp Asp Lys
    130                 135                 140

Gly Ala Ala His His His His His His
145                 150

<210> SEQ ID NO 106
<211> LENGTH: 153
<212> TYPE: PRT
<213> ORGANISM: Artificial Sequence
<220> FEATURE:
<223> OTHER INFORMATION: Humanized lama

<400> SEQUENCE: 106

Glu Val Gln Leu Val Glu Ser Gly Gly Gly Val Val Gln Pro Gly Gly
  1               5                  10                  15

Ser Leu Arg Leu Ser Cys Ala Ala Ser Gly Gly Thr Phe Ser Phe Tyr
                 20                  25                  30

Gly Met Gly Trp Phe Arg Gln Ala Pro Gly Lys Glu Arg Glu Phe Val
             35                  40                  45
```

```
Ala Asp Ile Arg Thr Ser Ala Gly Arg Thr Tyr Tyr Ala Asp Ser Val
 50                  55                  60
Lys Gly Arg Phe Thr Ile Ser Arg Asp Lys Ser Lys Asn Thr Val Tyr
 65                  70                  75                  80
Leu Gln Met Asn Ser Leu Arg Pro Glu Asp Thr Ala Leu Tyr Tyr Cys
                 85                  90                  95
Ala Ala Glu Pro Ser Gly Ile Ser Gly Trp Asp Tyr Trp Gly Gln Gly
                100                 105                 110
Thr Leu Val Thr Val Ser Ser Ala Ala Ala Asp Tyr Lys Asp His Asp
                115                 120                 125
Gly Asp Tyr Lys Asp His Asp Ile Asp Tyr Lys Asp Asp Asp Asp Lys
            130                 135                 140
Gly Ala Ala His His His His His His
145                 150

<210> SEQ ID NO 107
<211> LENGTH: 153
<212> TYPE: PRT
<213> ORGANISM: Artificial Sequence
<220> FEATURE:
<223> OTHER INFORMATION: Humanized lama

<400> SEQUENCE: 107

Glu Val Gln Leu Val Glu Ser Gly Gly Gly Val Val Gln Pro Gly Gly
 1                   5                  10                  15
Ser Leu Arg Leu Ser Cys Ala Ala Ser Gly Gly Thr Phe Ser Phe Tyr
                 20                  25                  30
Gly Met Gly Trp Phe Arg Gln Ala Pro Gly Lys Glu Arg Glu Phe Val
                 35                  40                  45
Ala Asp Ile Arg Thr Ser Ala Gly Arg Thr Tyr Tyr Ala Asp Ser Val
 50                  55                  60
Lys Gly Arg Phe Thr Ile Ser Arg Asp Ala Ser Lys Asn Thr Val Tyr
 65                  70                  75                  80
Leu Gln Met Asn Ser Leu Arg Pro Glu Asp Thr Ala Leu Tyr Tyr Cys
                 85                  90                  95
Ala Ala Glu Pro Ser Gly Ile Ser Gly Trp Asp Tyr Trp Gly Gln Gly
                100                 105                 110
Thr Leu Val Thr Val Ser Ser Ala Ala Ala Asp Tyr Lys Asp His Asp
                115                 120                 125
Gly Asp Tyr Lys Asp His Asp Ile Asp Tyr Lys Asp Asp Asp Asp Lys
            130                 135                 140
Gly Ala Ala His His His His His His
145                 150

<210> SEQ ID NO 108
<211> LENGTH: 153
<212> TYPE: PRT
<213> ORGANISM: Artificial Sequence
<220> FEATURE:
<223> OTHER INFORMATION: Humanized lama

<400> SEQUENCE: 108

Glu Val Gln Leu Val Glu Ser Gly Gly Gly Val Val Gln Pro Gly Gly
 1                   5                  10                  15
Ser Leu Arg Leu Ser Cys Ala Ala Ser Gly Gly Thr Phe Ser Phe Tyr
                 20                  25                  30
Gly Met Gly Trp Phe Arg Gln Ala Pro Gly Lys Glu Arg Glu Phe Val
                 35                  40                  45
```

```
Ala Asp Ile Arg Thr Ser Ala Gly Arg Thr Tyr Tyr Ala Asp Ser Val
        50                  55                  60

Lys Gly Arg Phe Thr Ile Ser Arg Asp Tyr Ser Lys Asn Thr Val Tyr
 65                  70                  75                  80

Leu Gln Met Asn Ser Leu Arg Pro Glu Asp Thr Ala Leu Tyr Tyr Cys
                 85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Asp Tyr Lys Asp His Asp
                115                 120                 125

Gly Asp Tyr Lys Asp His Asp Ile Asp Tyr Lys Asp Asp Asp Asp Lys
        130                 135                 140

Gly Ala Ala His His His His His His
145                 150

<210> SEQ ID NO 109
<211> LENGTH: 153
<212> TYPE: PRT
<213> ORGANISM: Artificial Sequence
<220> FEATURE:
<223> OTHER INFORMATION: Humanized lama

<400> SEQUENCE: 109

Glu Val Gln Leu Val Glu Ser Gly Gly Gly Val Val Gln Pro Gly Gly
 1               5                  10                  15

Ser Leu Arg Leu Ser Cys Ala Ala Ser Gly Gly Thr Phe Ser Phe Tyr
            20                  25                  30

Gly Met Gly Trp Phe Arg Gln Ala Pro Gly Lys Glu Arg Glu Phe Val
        35                  40                  45

Ala Asp Ile Arg Thr Ser Ala Gly Arg Thr Tyr Tyr Ala Asp Ser Val
        50                  55                  60

Lys Gly Arg Phe Thr Ile Ser Arg Asp Pro Ser Lys Asn Thr Val Tyr
 65                  70                  75                  80

Leu Gln Met Asn Ser Leu Arg Pro Glu Asp Thr Ala Leu Tyr Tyr Cys
                 85                  90                  95

Ala Ala Glu Pro Ser Gly Ile Ser Gly Trp Asp Tyr Trp Gly Gln Gly
            100                 105                 110

Thr Leu Val Thr Val Ser Ser Ala Ala Asp Tyr Lys Asp His Asp
                115                 120                 125

Gly Asp Tyr Lys Asp His Asp Ile Asp Tyr Lys Asp Asp Asp Asp Lys
        130                 135                 140

Gly Ala Ala His His His His His His
145                 150

<210> SEQ ID NO 110
<211> LENGTH: 138
<212> TYPE: PRT
<213> ORGANISM: Homo sapiens

<400> SEQUENCE: 110

Ala Met His Val Ala Gln Pro Ala Val Val Leu Ala Ser Ser Arg Gly
 1               5                  10                  15

Ile Ala Ser Phe Val Cys Glu Tyr Ala Ser Pro Gly Lys Ala Thr Glu
            20                  25                  30

Val Arg Val Thr Val Leu Arg Gln Ala Asp Ser Gln Val Thr Glu Val
        35                  40                  45
```

```
Cys Ala Ala Thr Tyr Met Met Gly Asn Glu Leu Thr Phe Leu Asp Asp
     50                  55                  60

Ser Ile Cys Thr Gly Thr Ser Ser Gly Asn Gln Val Asn Leu Thr Ile
65                  70                  75                  80

Gln Gly Leu Arg Ala Met Asp Thr Gly Leu Tyr Ile Cys Lys Val Glu
                 85                  90                  95

Leu Met Tyr Pro Pro Pro Tyr Tyr Leu Gly Ile Gly Asn Gly Thr Gln
                100                 105                 110

Ile Tyr Val Ile Asp Pro Glu Pro Cys Pro Asp Ser Asp Phe His His
            115                 120                 125

His His His His His His Gly Gly Gln
    130                 135

<210> SEQ ID NO 111
<211> LENGTH: 223
<212> TYPE: PRT
<213> ORGANISM: Homo sapiens

<400> SEQUENCE: 111

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
                20                  25                  30

Val Phe Cys Lys Ala Met His Val Ala Gln Pro Ala Val Val Leu Ala
            35                  40                  45

Ser Ser Arg Gly Ile Ala Ser Phe Val Cys Glu Tyr Ala Ser Pro Gly
        50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
                100                 105                 110

Asn Leu Thr Ile Gln Gly Leu Arg Ala Met Asp Thr Gly Leu Tyr Ile
            115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
                180                 185                 190

Arg Ser Pro Leu Thr Thr Gly Val Tyr Val Lys Met Pro Pro Thr Glu
                195                 200                 205

Pro Glu Cys Glu Lys Gln Phe Gln Pro Tyr Phe Ile Pro Ile Asn
                210                 215                 220
```